United States Patent
Hashimoto et al.

(10) Patent No.: US 6,616,607 B2
(45) Date of Patent: Sep. 9, 2003

(54) STATE INFORMATION ACQUISITION SYSTEM, STATE INFORMATION ACQUISITION APPARATUS, ATTACHABLE TERMINAL APPARATUS, AND STATE INFORMATION ACQUISITION METHOD

(75) Inventors: Kazuhiko Hashimoto, Moriguchi (JP); Shinji Tanaka, Kadoma (JP); Shigeyuki Inoue, Katano (JP); Nobuyuki Yoshiike, Ikoma (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

(21) Appl. No.: 09/981,333

(22) Filed: Oct. 17, 2001

(65) Prior Publication Data

US 2002/0091326 A1 Jul. 11, 2002

(30) Foreign Application Priority Data

| Oct. 18, 2000 | (JP) | 2000-318515 |
| Oct. 19, 2000 | (JP) | 2000-319870 |
| Oct. 20, 2000 | (JP) | 2000-321631 |
| Nov. 14, 2000 | (JP) | 2000-347247 |

(51) Int. Cl.$^7$ ................................................ A61B 5/00
(52) U.S. Cl. ................ 600/300; 340/573.1; 340/573.4; 128/903
(58) Field of Search ............................. 600/300, 301, 600/587, 592, 595; 128/903, 904; 340/573.1, 573.4

(56) References Cited

U.S. PATENT DOCUMENTS

| 5,544,649 | A | | 8/1996 | David et al. |
| 5,629,678 | A | * | 5/1997 | Gargano et al. ......... 340/573.4 |
| 5,976,083 | A | * | 11/1999 | Richardson et al. ........ 600/300 |
| 6,025,782 | A | * | 2/2000 | Newham ................. 340/573.1 |
| 6,208,251 | B1 | * | 3/2001 | Cadet et al. ............. 340/573.1 |
| 6,512,456 | B1 | * | 1/2003 | Taylor .................... 340/573.1 |

* cited by examiner

Primary Examiner—Eric F. Winakur
Assistant Examiner—David J. McCrosky
(74) Attorney, Agent, or Firm—RatnerPrestia

(57) ABSTRACT

A state information acquisition system has
- a terminal which has physiological state detecting means of detecting the physiological state of a person or animal, posture/action detecting means of detecting the posture and/or action state of the person or animal, and detection signal transmitting means of transmitting detection signals based on the detection of (1) the physiological state and (2) the posture and/or action state, and is attachable to the person or animal; and
- signal receiving and processing means which receives and processes a signal transmitted from the terminal and is located in a predetermined region; and
- thereby obtaining state information indicating the state of the person or animal on the basis of the detection signal.

11 Claims, 31 Drawing Sheets

Abnormal action detection system

STATE INFORMATION ACQUISITION SYSTEM, STATE INFORMATION ACQUISITION APPARATUS, ATTACHABLE TERMINAL APPARATUS, AND STATE INFORMATION ACQUISITION METHOD

BACKGROUND OF THE INVENTION

1. Field of the Invention

The present invention relates to, for example, a state information acquisition system, a state information acquisition apparatus, an attachable terminal apparatus, a state information acquisition method, and a personal characteristics information acquisition system for measuring the motion, posture, action state, and physiological state of a person.

2. Related Art of the Invention

With the entrance into the stage of an aged society, public attention is focused on the nursing care of elderlies. In particular, the nursing care of elderlies of dementia or prowling tendency is considered to be important, and various technology has been proposed in this application. Means of tracking the action of such an elderly person and thereby notifying abnormal action, in case of occurrence, to the person or another person would be useful for the nursing care. Further, in addition to such an elderly person, when the action of a person is measured and analyzed to obtain a behavior pattern, this permits the comfortable control and safe operation of illumination and air conditioning. This is useful in daily life.

In addition to a person, it is useful to measure the action of an animal or a machine. For an animal, such technology can be used in the research on not yet-known mode of life. For a machine, the measurement of state and operation permits efficient and safe running. This is useful in production activities.

In order to understand the action of a human body, it is important to detect "who (or what)," "where," and "what" of an action. For the purpose of this, it is necessary to (1) identify a person, (2) detect the position in a room, and (3) detect the action and the posture.

For the first issue of identifying a person, available methods include a method using RF-ID and a method by image recognition of CCD image.

The RF-ID is a system in which the identification information of a tag (called also a transponder, elsewhere) attached to a moving body such as human body and article is recognized automatically when an antenna (called also a reader, elsewhere) connected to a computer receives a radio wave of specific frequency.

These systems are classified into two categories from the viewpoint of the tag reading distance. The first category is the short distance type using lower frequencies in which the reading distance between the tag and the antenna is approximately 50 cm or less. In such a system, for example, a tag is exposed closely to an antenna, a tag is sewn into the end of a trouser leg, or a tag is read by an antenna located in a floor. The second category is the long distance type using microwaves in which the reading distance between the tag and the antenna exceeds 1 m. In such a system, it is sufficient for a tag to be carried with a human body or article. The tag information is read out without any intentional action when the tag passes by an antenna.

In the method by image recognition of CCD image, a human body or article passing through an entrance is shot by a CCD camera. Then, characteristic quantities such as the face of the human body and the shape and a mark of the article are extracted by means of image recognition, and compared with proper characteristic quantities previously registered, whereby the person or article is identified.

For the second issue of specifying the position of a human body or article in a room, available methods include extraction from CCD image and extraction from temperature distribution information obtained by a two-dimensional infra-red sensor. In addition, in case of a very large building, a method using a PHS or the like is proposed in which approximate position is specified on the basis of the intensity of the radio waves from a plurality of base station.

For the third issue of detecting the action and the posture, proposed methods include an old-fashioned method using a pedometer, a mercury switch, or the like to determine a static state or an acting state. Proposed recently is a method of detecting the state of walking, the inclination of body, and the direction of walking using various acceleration sensors and gyrosensors (angular velocity sensors) of high performance.

Further, in order to detect the physiological state of a human body, a ring sensor for detecting the light transmitting through a finger and a necklace sensor for detecting the vibration of heartbeat have been developed recently. These sensors contact the human body and detect the transmission and the vibration, thereby detecting the pulse and the like of the human body.

Nevertheless, each of these previously proposed various methods of detecting "who (or what)," "where," and "what" of an action has only a single function as described above.

(A) Accordingly, there has been the problem that the action, posture, and action state of a person such as "who (or what)," "where," and "what" of the action do not provide, at least directly, any information on the physiological state of the person.

Further, there has been the problem that it is difficult to obtain detailed information on the state of a person from the information obtained by any above-mentioned single function without obtaining the physiological information of the person.

(B) The RF-ID permits the identification of a specific person or article entering a room. Nevertheless, when a plurality of persons or articles enter the room, it is not possible to determine "who (or what)" exists "where," even using a method of specifying the position of the human bodies or articles. Further, even when the posture or the like is detected using an acceleration sensor, this does not provide any information on the position of the person in the posture.

Among the RF-ID systems for identifying a specific person or article, in the short distance type, the communication distance between the tag and the antenna is short. This has caused the necessity of explicitly exposing the tag to the antenna. On the contrary, in the long distance type, the communication distance between the tag and the antenna is long. This has caused the problem that a person or article not passing through but passing by the entrance can be detected in error. Further, the method of identifying a specific person or article from a CCD image needs extraction of characteristic quantities from the image. This has caused the problem that when the face is unseen at night or due to an obstacle, the human body is not detected at all.

(C) Further, in the method of receiving the sensor signals from the ring sensor, the necklace sensor, or the like, there have been the problems of a higher noise level, the large amount of data, and the like.

(D) Further, in this system, the action state of "who," "where," and "what" is obtained accurately. Nevertheless, for example, in case that the home of the person of object of detection of action state is far from a hospital, the doctor in the hospital can not automatically obtain the action state of the person of object of detection. Accordingly, there has been the problem that even in case of the occurrence or the possible occurrence of abnormality in the person of object of detection, the doctor can not give any advice such as treatment information to the person of object of detection or the person's helper.

SUMMARY OF THE INVENTION

The present invention has been devised with considering these problems in the prior art. An object of the present invention is to provide a state information acquisition system, a state information acquisition apparatus, an attachable terminal apparatus, a state information acquisition method, a personal characteristics information acquisition system, a medium, and an informational set for directly obtaining the physiological state of a person. Further, considering the above-mentioned problems in the prior art, an object of the present invention is to provide a state information acquisition system, a state information acquisition apparatus, an attachable terminal apparatus, a state information acquisition method, a personal characteristics information acquisition system, a program, and a medium for obtaining more detailed information on the state of a person.

Further, considering the above-mentioned problems in the prior art, an object of the present invention is to provide a state information acquisition system, a state information acquisition apparatus, a state information acquisition method, an abnormal action detection system, a program, and a medium for integrally obtaining state information indicating the state of a person or an animal.

Further, the present invention has been devised with considering the prior art problem of largeness in the amount of data of: physiological information transmitted from transmitting means to a personal information terminal; physiological information transmitted from the personal information terminal to a base station; and information on all or part of posture, action, and motion state of a human body, transmitted from the personal information terminal to the base station. An object of the present invention is to provide a state information detection and transmission apparatus, a personal information terminal, transmitting means, an alarm notification system, a personal characteristics information acquisition system, a state information detection and transmission method, a physiological information processing method, a transmission method, a program, and a medium capable of reducing the amount of data of: physiological information transmitted from transmitting means to a personal information terminal; physiological information transmitted from the personal information terminal to a base station; and information on all or part of posture, action, and motion state of a human body, transmitted from the personal information terminal to the base station.

Further, considering the above-mentioned problems in the prior art, an object of the present invention is to provide an action detection system, an action detection method, a program, and a medium in which information on the action state of a person of object of detection is automatically transmitted via the Internet to a first Internet terminal of a predetermined manager (such as a doctor), and a second Internet terminal is used for performing interactive communications with the first Internet terminal via the Internet, whereby information exchange can be carried out between the person of object of detection or the person's helper and the manager.

The 1st invention of the present invention is a state information acquisition system comprising:

a terminal which has physiological state detecting means of detecting the physiological state of a person or animal, posture/action detecting means of detecting the posture and/or action state of said person or animal, and detection signal transmitting means of transmitting detection signals based on the detection of (1) said physiological state and (2) said posture and/or action state, and is attachable to said person or animal; and signal receiving and processing means which receives and processes a signal transmitted from said terminal and is located in a predetermined region; and thereby obtaining state information indicating the state of said person or animal on the basis of said detection signal.

The 2nd invention of the present invention is a state information acquisition method comprising the steps of:

detecting the physiological state of a person or animal;

detecting the posture and/or action state of said person or animal;

transmitting detection signals based on the detection of (1) said physiological state and (2) said posture and/or action state;

receiving and processing said transmitted signal; and obtaining state information indicating the state of said person or animal on the basis of said detection signal.

The 3rd invention of the present invention is a state information acquisition system according to 1st invention comprising:

radio wave transmitting means which is located in said predetermined region and transmits a radio wave; and movement direction detecting means which is located in an entrance of said predetermined region and detects the movement direction of said person or animal; wherein said terminal has radio wave receiving means of receiving said radio wave when the distance from said radio wave transmitting means is a predetermined value or less, and the transmission of said detection signals based on the detection of (1) said physiological state and (2) said posture and/or action state is carried out on the basis of the reception of said radio wave and the detection of said movement direction.

The 4th invention of the present invention is a state information acquisition system according to 1st invention comprising position detecting means which is located in said predetermined region and detects the position of said person or animal, wherein when said state information is obtained, said position of said person or animal detected by said position detecting means is considered.

The 5th invention of the present invention is a state information acquisition system according to 1st invention wherein said detection signal has a frequency specific to said person or animal, said state information acquisition system comprises identifying means of identifying said person or animal on the basis of said specific frequency, and when said state information is obtained, the result of identification carried out by said identifying means is considered.

The 6th invention of the present invention is a state information acquisition system according to 1st invention wherein said physiological state detecting means and said detection signal transmitting means are integrated in a common case.

The 7th invention of the present invention is a state information acquisition system according to 1st invention comprising:

storing means of storing, as structured data, said state information obtained on the basis of said detection signal and/or standard information previously prepared;

comparing and determining means of comparing said obtained state information with said stored structured data on the basis of a predetermined reference and thereby determining whether the state of said person or animal of object of detection is normal or abnormal; and notifying means of notifying abnormality when said state of said person or animal is determined to be abnormal.

The 8th invention of the present invention is a state information acquisition apparatus comprising signal receiving and processing means which receives and processes a detection signal of the physiological state of a person or animal and a detection signal of the posture and/or action state of a person or animal and is located in a predetermined region, wherein (1) the output from said signal receiving and processing means contains state information which is based on said detection signal and indicates the state of said person or animal, or (2) said processed signal is output for the preparation of state information.

The 9th invention of the present invention is a state information acquisition method comprising the step of receiving and processing a detection signal of the physiological state of a person or animal and a detection signal of the posture and/or action state of a person or animal, wherein (1) said processed signal contains state information which is based on said detection signal and indicates the state of said person or animal, or (2) said processed signal is output for the preparation of state information.

The 10th invention of the present invention is an attachable terminal apparatus comprising detection signal transmitting means of obtaining and transmitting detection signals based on the detection of (1) the physiological state of a person or animal and (2) the posture and/or action state of said person or animal, wherein said detection signal transmitting means is attachable to said person or animal.

The 11th invention of the present invention is a state information acquisition method comprising the step of obtaining and transmitting, in the state of being attached to a person or animal, detection signals based on the detection of (1) the physiological state of said person or animal and (2) the posture and/or action state of said person or animal.

The 12th invention of the present invention is a state information acquisition system comprising:

a terminal which has physiological state detecting means of detecting the physiological state of a person or animal and detection signal transmitting means of transmitting a detection signal based on said detection, and is attachable to said person or animal;

receiving means which receives a signal transmitted from said terminal and is located in a predetermined region; and signal processing and outputting means of processing said received signal and then outputting the result; and thereby obtaining state information indicating the state of said person or animal on the basis of said detection signal.

The 13th invention of the present invention is a state information acquisition method comprising the steps of:

detecting, in the state of being attached to a person or animal, the physiological state of said person or animal and thereby transmitting a detection signal based on said detection;

receiving said transmitted signal;

processing said received signal and then outputting the result; and obtaining state information indicating the state of said person or animal on the basis of said detection signal.

The 14th invention of the present invention is a state information acquisition system according to 12th invention comprising position detecting means of detecting the position of said person or animal, wherein when said state information is obtained, the result of detection carried out by said position detecting means is considered.

The 15th invention of the present invention is a state information acquisition system according to 12th invention comprising identifying means of identifying said person or animal, wherein when said state information is obtained, the result of identification carried out by said identifying means is considered.

The 16th invention of the present invention is a personal characteristics information acquisition system comprising:

radio wave transmitting means which is located at least at one position in a room and transmits a radio wave of specific frequency;

radio wave receiving means of receiving when the distance from said radio wave transmitting means is a predetermined value or less;

posture/action detecting means of detecting the posture, position, action, and motion state of a human body;

physiological state detecting means of detecting the physiological state such as pulse and heartbeat of said human body;

sensor signal transmitting means of transmitting a sensor signal obtained from said physiological state detecting means;

sensor signal receiving means of receiving a sensor signal obtained from said sensor signal transmitting means;

a wearable personal information terminal having said radio wave receiving means, said posture/action detecting means, said sensor signal receiving means, and sensor signal processing means of obtaining the personal characteristics information of said human body;

a master apparatus for successively transmitting and receiving the sensor signals from a plurality of said wearable personal information terminals by wireless; and signal processing means of integrally processing, by means of a network, the signals obtained from said sensor signals from said master apparatus and thereby obtaining the personal characteristics information of said human body.

The 17th invention of the present invention is a personal characteristics information acquisition system according to 16th invention comprising:

position detecting means which is located at least at one position in said room and detects the position of said human body by means of image processing;

movement direction detecting means which is located in an entrance of said room and detects the movement direction of said human body;

storing means of storing the action information of said human body obtained from said signal processing means, in an integrated form of structured data by means of a network;

action evaluating means of evaluating said action information of said human body obtained from said signal processing means by comparing it with said structured data stored in said storing means connected to said network;

state determining means of determining and predicting an abnormality in the action state of said human body obtained from said action evaluating means; and notifying means of notifying said determined abnormality in said action state of said human body to said personal information terminal and other terminals connected to said network; wherein the results of detection by said position detecting means and said movement direction detecting means are integrated into said action information by said signal processing means.

The 18th invention of the present invention is a state information acquisition system comprising:

position detecting means of detecting the position of a person or animal and thereby transmitting a position detection signal;

a terminal which has posture/action detecting means of detecting the posture and/or action state of said person or animal and detection signal transmitting means of transmitting a state detection signal based on the detection of said posture and/or action state, and is attachable to said person or animal; and signal receiving and processing means which receives and processes said position detection signal and said state detection signal, and is located in a predetermined region; and thereby obtaining state information indicating the state of said person or animal on the basis of the result of said processing.

The 19th invention of the present invention is a state information acquisition method comprising the steps of:

detecting the position of a person or animal and thereby transmitting a position detection signal;

detecting the posture and/or action state of said person or animal and thereby transmitting a state detection signal;

receiving and processing said position detection signal and said state detection signal; and obtaining state information indicating the state of said person or animal on the basis of the result of said processing.

The 20th invention of the present invention is a state information acquisition system according to 18th invention wherein:

the object of said detection is a person;

said state information acquisition system comprises lavatory state detecting means of detecting the state of said person in a lavatory; and when said state information is obtained, the result of detection carried out by said lavatory state detecting means is considered.

The 21st invention of the present invention is a state information acquisition system according to 18th invention wherein:

the object of said detection is a person;

said state information acquisition system comprises on-bed state detecting means of detecting the state of said person on a bed; and when said state information is obtained, the result of detection carried out by said on-bed state detecting means is considered.

The 22nd invention of the present invention is a state information acquisition system according to 18th invention comprising:

radio wave transmitting means which is located in said predetermined region and transmits a radio wave; and movement direction detecting means which is located in an entrance of said predetermined region and detects the movement direction of said person or animal; wherein said terminal has radio wave receiving means of receiving said radio wave when the distance from said radio wave transmitting means is a predetermined value or less, and the transmission of said state detection signal is carried out on the basis of the reception of said radio wave and the detection of said movement direction.

The 23rd invention of the present invention is a state information acquisition system according to 18th invention wherein said state detection signal has a frequency specific to said person or animal, said state information acquisition system comprises identifying means of identifying said person or animal on the basis of said specific frequency, and when said state information is obtained, the result of identification carried out by said identifying means is considered.

The 24th invention of the present invention is a state information acquisition system according to 18th invention comprising:

storing means of storing, as structured data, said state information obtained on the basis of the result of said processing and/or standard information previously prepared;

comparing and determining means of comparing said obtained state information with said stored structured data on the basis of a predetermined reference and thereby determining whether the state of said person or animal of object of detection is normal or abnormal; and notifying means of notifying abnormality when said state of said person or animal is determined to be abnormal.

The 25th invention of the present invention is a state information acquisition apparatus comprising signal receiving and processing means which receives and processes a position detection signal based on the detection of the position of a person or animal and a state detection signal based on the detection of the posture and/or action state of said person or animal and is located in a predetermined region, wherein (1) the output from said signal receiving and processing means contains state information which is based on the result of said processing and indicates the state of said person or animal, or (2) said processed signal is output for the preparation of state information.

The 26th invention of the present invention is a state information acquisition method comprising the step of receiving and processing a position detection signal based on the detection of the position of a person or animal and a state detection signal based on the detection of the posture and/or action state of said person or animal, wherein
(1) said processed signal contains state information which is based on the result of said processing and indicates the state of said person or animal, or (2) said processed signal is output for the preparation of state information.

The 27th invention of the present invention is a state information acquisition system comprising:
identifying means of identifying a person or animal;
position detecting means of detecting the position of said person or animal and thereby transmitting a position detection signal; and
signal processing and outputting means of receiving and processing said position detection signal with considering the result of said identification, and then outputting the result; and
thereby obtaining state signal indicating the state of said person or animal on the basis of the result of said processing.

The 28th invention of the present invention is a state information acquisition method comprising the steps of:
identifying a person or animal;
detecting the position of said person or animal and thereby transmitting a position detection signal;
receiving and processing said position detection signal with considering the result of said identification, and then outputting the result; and
obtaining state signal indicating the state of said person or animal on the basis of the result of said processing.

The 29th invention of the present invention is a state information acquisition system comprising:
identifying means of identifying a person or animal;
a terminal which has posture/action detecting means of detecting the posture and/or action state of said person or animal and detection signal transmitting means of transmitting a state detection signal based on the detection of said posture and/or action state, and is attachable to said person or animal; and
signal processing and outputting means of receiving and processing said state detection signal with considering the result of said identification, and then outputting the result; and
thereby obtaining state information indicating the state of said person or animal on the basis of the result of said processing.

The 30th invention of the present invention is a state information acquisition method comprising the steps of:
identifying a person or animal;
detecting, in the state of being attached to said person or animal, the posture and/or action state of said person or animal and transmitting a state detection signal based on the detection of said posture and/or action state;
receiving and processing said state detection signal with considering the result of said identification, and then outputting the result; and
obtaining state information indicating the state of said person or animal on the basis of the result of said processing.

The 31th invention of the present invention is an abnormal action detection system comprising:

position detecting means which is located at least at one position in a room and detects the position of a human body by means of image processing;
movement direction detecting means which is located in an entrance of said room and detects the movement direction of said human body;
transmitting means which is located at least at one position in said room and transmits a radio wave of specific frequency;
receiving means of receiving when the distance from said transmitting means is a predetermined value or less;
posture/action detecting means of detecting the posture, action, and motion state of said human body;
a wearable personal information terminal having said receiving means, said posture/action detecting means, and signal processing means of obtaining the action information of said human body;
a master apparatus for successively transmitting and receiving the sensor signals from a plurality of said wearable personal information terminals by wireless;
signal processing means of integrally processing said sensor signals from said master apparatus and the signals obtained from said position detecting means and said movement direction detecting means and thereby obtaining the action information of said human body;
storing means of storing the action information of said human body obtained from said signal processing means, in an integrated form of structured data by means of a network;
action evaluating means of evaluating said action information of said human body obtained from said signal processing means by comparing it with said structured data stored in said storing means connected to said network;
state determining means of determining and predicting an abnormality in the action state of said human body obtained from said action evaluating means; and
notifying means of notifying said determined abnormality in said action state of said human body to said personal information terminal and other terminals connected to said network.

The 32th invention of the present invention is an abnormal action detection system according to 31st invention comprising human body state detecting means of detecting an abnormal state of said human body in a lavatory, wherein
the result of detection by said human body state detecting means is integrated into said action information by said signal processing means.

The 33th invention of the present invention is an abnormal action detection system according to 31st invention comprising on-bed state detecting means of detecting the on-bed state of said human body on a bed, wherein
the result of detection by said on-bed state detecting means is integrated into said action information by said signal processing means.

The 34th invention of the present invention is a state information detection and transmission apparatus comprising:
physiological information detecting means of detecting the physiological information of a human body;
transmitting means of transmitting said physiological information detected by said physiological information detecting means; and a wearable personal information terminal having: receiving means of receiving said physiological information from said transmitting means; and sending means of sending said physiological information received by said receiving means or physiological information generated by signal processing of said physiological information, to a predetermined base station; wherein (1) said transmitting means transmits said physiological information detected by said physiological information detecting means to said personal information terminal in every predetermined time interval, or (2) said receiving means receives said physiological information from said transmitting means in every predetermined time interval, or (3) said sending means sends said physiological information to said base station in every predetermined time interval.

The 35th invention of the present invention is a state information detection and transmission method comprising the steps of:

detecting the physiological information of a human body;

transmitting said detected physiological information; and in a wearable personal information terminal: receiving said physiological information; and sending said received physiological information or physiological information generated by signal processing of said physiological information, to a predetermined base station; wherein (1) said detected physiological information is transmitted to said personal information terminal in every predetermined time interval, or (2) said physiological information is received in every predetermined time interval, or (3) said physiological information is sent to said base station in every predetermined time interval.

The 36th invention of the present invention is a wearable personal information terminal having: receiving means of receiving physiological information from transmitting means of transmitting physiological information detected by physiological information detecting means of detecting the physiological information of a human body; and sending means of sending said physiological information received by said receiving means or physiological information generated by signal processing of said physiological information, to a predetermined base station; wherein (1) said receiving means receives said physiological information from said transmitting means in every predetermined time interval, or (2) said sending means sends said physiological information to said base station in every predetermined time interval.

The 37th invention of the present invention is a personal information processing method comprising the steps of:

receiving detected and transmitted physiological information of a human body, by a predetermined personal information terminal; and sending said received physiological information or physiological information generated by signal processing of said physiological information, from said personal information terminal to a predetermined base station; wherein (1) said physiological information is received in every predetermined time interval, or (2) said physiological information is sent to said base station in every predetermined time interval.

The 38th invention of the present invention is transmitting means of transmitting physiological information detected by physiological information detecting means of detecting the physiological information of a human body, to a predetermined personal information terminal, wherein said transmitting means transmits said physiological information detected by said physiological information detecting means to said personal information terminal in every predetermined time interval.

The 39th invention of the present invention is a transmitting method comprising the step of transmitting detected physiological information of a human body to a predetermined personal information terminal, wherein said detected physiological information is transmitted to said personal information terminal in every predetermined time interval.

The 40th invention of the present invention is a state information detection and transmission apparatus comprising:

physiological information detecting means of detecting the physiological information of a human body;

transmitting means of transmitting said physiological information detected by said physiological information detecting means; and a wearable personal information terminal having: receiving means of receiving said physiological information from said transmitting means; and sending means of sending said physiological information received by said receiving means or physiological information generated by signal processing of said physiological information, to a predetermined base station; wherein (1) said transmitting means transmits said physiological information to said personal information terminal only when a substantial change occurs in the signal detected by said physiological information detecting means, or (2) said sending means sends said physiological information to said base station only when a substantial change occurs in said physiological information received by said receiving means.

The 41th invention of the present invention is a state information detection and transmission method comprising the steps of:

detecting the physiological information of a human body;

transmitting said detected physiological information; and in a wearable personal information terminal: receiving said physiological information; and sending said received physiological information or physiological information generated by signal processing of said physiological information, to a predetermined base station; wherein (1) said physiological information is transmitted to said personal information terminal only when a substantial change occurs in said physiological information, or (2) said physiological information is sent to said base station only when a substantial change occurs in said received physiological information.

The 42th invention of the present invention is a wearable personal information terminal having: receiving means of receiving physiological information from transmitting means of transmitting physiological information detected by physiological information detecting means of detecting the physiological information of a human body; and sending means of sending said physiological information received by said receiving means or physiological information generated by signal processing of said physiological information, to a predetermined base station; wherein said sending means sends said physiological information to said base station only when a substantial change occurs in said physiological information received by said receiving means.

The 43th invention of the present invention is a personal information processing method comprising the steps of:

receiving detected and transmitted physiological information of a human body, by a predetermined personal information terminal; and sending said received physiological information or physiological information generated by signal processing of said physiological information, from said personal information terminal to a predetermined base station; wherein said physiological information is sent to said base station only when a substantial change occurs in said received physiological information.

The 44th invention of the present invention is transmitting means of transmitting physiological information detected by physiological information detecting means of detecting the physiological information of a human body, to a predetermined personal information terminal, wherein said transmitting means transmits said physiological information to said personal information terminal only when a substantial change occurs in the signal detected by said physiological information detecting means.

The 45th invention of the present invention is a transmitting method comprising the step of transmitting detected physiological information of a human body to a predetermined personal information terminal, wherein said physiological information is transmitted to said personal information terminal only when a substantial change occurs in said physiological information.

The 46th invention of the present invention is a state information detection and transmission apparatus according to 34th or 40th inventions wherein said transmitting means is carried with said human body, said transmitting means further comprises uncarry detecting means of detecting that said transmitting means becomes uncarried with said human body, when said uncarry detecting means detects that said transmitting means becomes uncarried with said human body, said transmitting means transmits uncarry information indicating this situation to said personal information terminal, and said personal information terminal sends said uncarry information to said base station.

The 47th invention of the present invention is a state information detection and transmission apparatus according to 34th or 40th inventions wherein said personal information terminal further comprises uncarry detecting means of detecting that said personal information terminal becomes uncarried with said human body, and when said uncarry detecting means detects that said personal information terminal becomes uncarried with said human body, said sending means sends uncarry information indicating this situation to said base station.

The 48th invention of the present invention is a wearable personal information terminal having:

state detecting means of detecting all or part of the posture, action, and motion state of a human body; and sending means of sending state information detected by said state detecting means or state information generated by signal processing of said state information, to a predetermined base station; wherein said sending means sends said state information to said base station in every predetermined time interval.

The 49th invention of the present invention is a personal information processing method comprising the steps of:

detecting, as state information, all or part of the posture, action, and motion state of a human body; and sending said detected state information or state information generated by signal processing of said state information, from a predetermined personal information terminal to a predetermined base station; wherein said state information is sent to said base station in every predetermined time interval.

The 50th invention of the present invention is a wearable personal information terminal having:

state detecting means of detecting all or part of the posture, action, and motion state of a human body; and sending means of sending state information detected by said state detecting means or state information generated by signal processing of said state information, to a predetermined base station; wherein said sending means sends said state information to said base station only when a substantial change occurs in the signal detected by said state information detecting means.

The 51h invention of the present invention is a personal information processing method comprising the steps of:

detecting, as state information, all or part of the posture, action, and motion state of a human body; and sending said detected state information or state information generated by signal processing of said state information, from a predetermined personal information terminal to a predetermined base station; wherein said state information is sent to said base station only when a substantial change occurs in said detected signal.

The 52th invention of the present invention is a personal information terminal according to 50th invention wherein said personal information terminal further comprises uncarry detecting means of detecting that said personal information terminal becomes uncarried with said human body, and when said uncarry detecting means detects that said personal information terminal becomes uncarried with said human body, said sending means sends uncarry information indicating this situation to said base station.

The 53th invention of the present invention is a state information detection and transmission apparatus comprising:

physiological information detecting means of detecting the physiological information of a human body;

transmitting means of transmitting said physiological information detected by said physiological information detecting means; and a wearable personal information terminal having: receiving means of receiving said physiological information from said transmitting means; state detecting means of detecting all or part of the posture, action, and motion state of said human body; and sending means of sending all or part of state information composed of said physiological information received by said receiving means and the information detected by said state detecting means, or alternatively all or part of state information generated by signal processing of said state information, to a predetermined base station; wherein said sending means sends said state information to said base station only when a substantial change occurs in at least a part of said physiological information received by said receiving means and said information detected by said state detecting means.

The 54th invention of the present invention is a state information detection and transmission method comprising the steps of:

detecting the physiological information of a human body;

transmitting said detected physiological information; and in a wearable personal information terminal: receiving said physiological information; detecting all or part of the posture, action, and motion state of said human body; and sending all or part of state information composed of said received physiological information and said detected information, or alternatively all or part of state information generated by signal processing of said state information, to a predetermined base station; wherein said state information is sent to said base station only when a substantial change occurs in at least a part of said received physiological information and said detected information.

The 55th invention of the present invention is a state information detection and transmission apparatus comprising:

physiological information detecting means of detecting the physiological information of a human body;

transmitting means of transmitting said physiological information detected by said physiological information detecting means; and a wearable personal information terminal having: receiving means of receiving said physiological information from said transmitting means; state detecting means of detecting all or part of the posture, action, and motion state of said human body; and sending means of sending all or part of state information composed of said physiological information received by said receiving means and the information detected by said state detecting means, or alternatively all or part of state information generated by signal processing of said state information, to a predetermined base station; wherein said receiving means receives said physiological information from said transmitting means only when a substantial change occurs in the signal detected by said state detecting means.

The 56th invention of the present invention is a state information detection and transmission method comprising the steps of:

detecting the physiological information of a human body;

transmitting said detected physiological information; and in a wearable personal information terminal: receiving said physiological information; detecting all or part of the posture, action, and motion state of said human body; and sending all or part of state information composed of said received physiological information and said detected information, or alternatively all or part of state information generated by signal processing of said state information, to a predetermined base station; wherein said physiological information is received only when a substantial change occurs in said detected signal.

The 57th invention of the present invention is a state information detection and transmission apparatus according to 55th invention wherein said transmitting means is carried with said human body, further comprised is uncarry detecting means of detecting that said transmitting means becomes uncarried with said human body and/or that said personal information terminal becomes uncarried with said human body, when said uncarry detecting means detects that said transmitting means and/or said personal information terminal become uncarried with said human body, said transmitting means and/or said sending means transmits and/or sends uncarry information indicating these situations.

The 58th invention of the present invention is a wearable personal information terminal having:

receiving means of receiving physiological information from transmitting means of transmitting physiological information detected by physiological information detecting means of detecting the physiological information of a human body;

state detecting means of detecting all or part of the posture, action, and motion state of said human body; and sending means of sending all or part of state information composed of said physiological information received by said receiving means and the information detected by said state detecting means, or alternatively all or part of state information generated by signal processing of said state information, to a predetermined base station; wherein said receiving means receives said physiological information from said transmitting means only when a substantial change occurs in the information detected by said state detecting means.

The 59th invention of the present invention is a personal information processing method comprising the steps of:

receiving detected and transmitted physiological information of a human body, by a predetermined personal information terminal;

detecting all or part of the posture, action, and motion state of said human body; and sending all or part of state information composed of said received physiological information and said detected information, or alternatively all or part of state information generated by signal processing of said state information, from said personal information terminal to a predetermined base station; wherein said physiological information is received only when a substantial change occurs in said detected information.

The 60th invention of the present invention is a personal information terminal according to any one of 36th, 42th, 48th, 50th, 52th, and 58th inventions further comprising notifying means of notifying abnormality information by means of sound or color, when all or part of said detected physiological information or said detected state information falls within the range of predetermined abnormality information.

The 61st invention of the present invention is an alarm notifying system comprising at least: a personal information terminal according to any one of 36th, 42nd, 48th, 50th, 52nd, 58th, and 60th inventions; and a base station for receiving physiological information or state information from said personal information terminal by wireless; wherein said personal information terminal comprises an alarm button to be arbitrarily pushed by a human body in order to notify an abnormality, and said alarm notifying system further comprises notifying means of notifying, by means of sound or color, abnormality information indicating the abnormality when said alarm button is pushed.

The 62nd invention of the present invention is an alarm notifying system comprising at least: a personal information terminal according to any one of 36, 42nd, 48, 50, 52nd, 58, and 60 inventions; and a base station for receiving physiological information or state information from said personal information terminal by wireless; wherein said personal information terminal comprises an alarm button to be arbitrarily pushed by a human body in order to notify an abnormality, and when said alarm button is pushed, abnormality information indicating the abnormality is sent from said personal information terminal to said base station.

The 63rd invention of the present invention is a personal characteristics information acquisition system comprising: a personal information terminal according to any one of 36th, 42nd, 48th, 50th, 52nd, 58th, and 60th inventions; a base station for receiving physiological information or state information from said personal information terminal by wireless; and personal characteristics information calculating means of obtaining the personal characteristics information of a human body on the basis of said physiological information or said state information received by said base station.

The above-mentioned state information detection and transmission apparatus according to the invention may comprise radio wave transmitting means which is located at least at one position in a room and transmits a radio wave of specific frequency, while the above-mentioned personal information terminal according to the invention may comprise radio wave receiving means of receiving said radio wave from said radio wave transmitting means when the distance from said radio wave transmitting means is a predetermined value or less.

In the above-mentioned configuration according to the invention, the action and the personal characteristics information of a person, such as position, posture, action information, and physiological information, can be measured accurately and easily. Further, state determining means attached to the human body communicates with the base station by wireless, and the base station is connected to the network. This permits integrated management of the personal characteristics information of human bodies in a plurality of rooms or specified areas. Accordingly, the action of the human bodies in the whole building can be understood in real time. This permits various applications such as abnormality detection, air conditioning/illumination control, and security.

The term "wearable" in the present specification indicates portability.

The 64th invention of the present invention is an action detection system comprising:

a wearable personal information terminal for acquiring at least a part of the personal characteristic action information of a human body;

action information acquiring means which is uncarried with said human body and located in a predetermined fixed place, and acquires at least a part of the personal characteristic action information of said human body;

a base station for receiving said personal characteristic action information from said personal information terminal by wireless;

action state calculating means of integrally processing said personal characteristic action information received by said base station and said personal characteristic action information from said action information acquiring means and thereby obtaining the action state of said human body;

state determining means of comparing said action state obtained by said action state calculating means with predetermined reference information and thereby determining and predicting the presence or absence of abnormality in said action state of said human body;

a first Internet terminal for transmitting, via the Internet, the result of determination by said state determining means, or alternatively said result of determination and said action state information obtained by said action state calculating means; and a second Internet terminal for receiving said result of determination, or alternatively said result of determination and said action state information, from said first Internet terminal via the Internet; wherein said first Internet terminal and said second Internet terminal can perform interactive information communications with each other via the Internet.

The 65th invention of the present invention is an action detection method comprising the steps of:

acquiring, in the state of being carried with a human body, at least a part of the personal characteristic action information of said human body;

acquiring, in the state of being uncarried with said human body and located in a predetermined fixed place, at least a part of the personal characteristic action information of said human body;

receiving said personal characteristic action information by wireless;

integrally processing said received personal characteristic action information and said personal characteristic action information and thereby obtaining the action state of said human body;

comparing said obtained action state with predetermined reference information and thereby determining and predicting the presence or absence of abnormality in said action state of said human body;

transmitting the result of said determination, or alternatively said result of determination and said obtained action state information, from a first Internet terminal via the Internet; and receiving said result of determination, or alternatively said result of determination and said action state information, from said first Internet terminal via the Internet by a second Internet terminal; wherein said first Internet terminal and said second Internet terminal can perform interactive information communications with each other via the Internet.

The 66th invention of the present invention is an action detection system according to 64th invention wherein when said state determining means determines an abnormality, said first Internet terminal transmits said result of determination, or alternatively said result of determination and said action state information.

The 67th invention of the present invention is an action detection system according to 64th invention further comprising an apparatus which can be connected to said first Internet terminal and the operation of which is controlled on the basis of the instructions from said second Internet terminal.

The 68th invention of the present invention is an action detection system according to 64th invention wherein said action information acquiring means comprises: radio wave transmitting means which is located at least at one position in a room and transmits a radio wave of specific frequency; physiological state detecting means of detecting the physiological state of said human body; and physiological information transmitting means of transmitting the physiological information detected by said physiological state detecting means, to said personal information terminal;

said personal information terminal comprises: radio wave receiving means of receiving the radio wave from said radio wave transmitting means when the distance from said radio wave transmitting means is a predetermined value or less; state detecting means of detecting all or part of the posture, action, and motion state of said human body; physiological information receiving means of receiving said physiological information from said physiological information transmitting means; and sending means of sending, as personal characteristic action information, all or part of reception information indicating the reception of radio wave from said radio wave transmitting means, said state information detected by said state detecting means, and said physiological information received by said physiological information receiving means, to said base station.

According to the action detection system of the invention having the above-mentioned configuration, a human body entering a room can be identified. Further, the action and the state of the human body, such as in-room position, posture, action physiological information, can be measured accurately. This permits easy determination and prediction of abnormality. The result can be notified to another person via the Internet. Further, state determining means attached to the human body communicates with the base station by wireless, and the base station is connected to the network. This permits integrated management of the personal characteristics information of human bodies in a plurality of rooms or specified areas. Accordingly, the action of the human bodies in the whole building can be understood in real time. This permits various applications such as abnormality detection, air conditioning/illumination control, and security.

The term "wearable" in the present specification indicates portability.

The 69th invention of the present invention is a computer processable medium carrying a program to cause a computer to execute all or part of the state information acquisition method according to 2nd invention comprising the steps of: detecting the physiological state of a person or animal; detecting the posture and/or action state of said person or animal; transmitting detection signals based on the detection of (1) said physiological state and (2) said posture and/or action state; receiving and processing said transmitted signal; and obtaining state information indicating the state of said person or animal on the basis of said detection signal.

The 70th invention of the present invention is a computer processable medium carrying a program to cause a computer to execute all or part of the state information acquisition method according to 13th invention comprising the steps of: detecting, in the state of being attached to a person or animal, the physiological state of said person or animal and thereby transmitting a detection signal based on said detection; receiving said transmitted signal; processing said received signal and then outputting the result; and obtaining state information indicating the state of said person or animal on the basis of said detection signal.

The 71st invention of the present invention is a computer processable medium carrying a program to cause a computer to execute all or part of the state information acquisition method according to 19th invention comprising the steps of: detecting the position of a person or animal and thereby transmitting a position detection signal; detecting the posture and/or action state of said person or animal and thereby transmitting a state detection signal; receiving and processing said position detection signal and said state detection signal; and obtaining state information indicating the state of said person or animal on the basis of the result of said processing.

The 72nd invention of the present invention is a computer processable medium carrying a program to cause a computer to execute all or part of the state information acquisition method according to 28th invention comprising the steps of: identifying a person or animal; detecting the position of said person or animal and thereby transmitting a position detection signal; receiving and processing said position detection signal with considering the result of said identification, and then outputting the result; and obtaining state signal indicating the state of said person or animal on the basis of the result of said processing.

The 73rd invention of the present invention is a computer processable medium carrying a program to cause a computer to execute all or part of the state information acquisition method according to 30th invention comprising the steps of: identifying a person or animal; detecting, in the state of being attached to said person or animal, the posture and/or action state of said person or animal and transmitting a state detection signal based on the detection of said posture and/or action state; receiving and processing said state detection signal with considering the result of said identification, and then outputting the result; and obtaining state information indicating the state of said person or animal on the basis of the result of said processing.

The 74th invention of the present invention is a computer processable medium carrying a program to cause a computer to execute all or part of the state information detection and transmission method according to 35th invention comprising the steps of: detecting the physiological information of a human body; transmitting said detected physiological information; and in a wearable personal information terminal: receiving said physiological information; and sending said received physiological information or physiological information generated by signal processing of said physiological information, to a predetermined base station.

The 75th invention of the present invention is a computer processable medium carrying a program to cause a computer to execute all or part of the state information detection and transmission method according to 41th invention comprising the steps of: detecting the physiological information of a human body; transmitting said detected physiological information; and in a wearable personal information terminal: receiving said physiological information; and sending said received physiological information or physiological information generated by signal processing of said physiological information, to a predetermined base station.

The 76th invention of the present invention is a computer processable medium carrying a program to cause a computer to execute all or part of the state information detection and transmission method according to 54th invention comprising the steps of: detecting the physiological information of a human body; transmitting said detected physiological information; and in a wearable personal information terminal: receiving said physiological information; detecting all or part of the posture, action, and motion state of said human body; and sending all or part of state information composed of said received physiological information and said detected information, or alternatively all or part of state information generated by signal processing of said state information, to a predetermined base station.

The 77th invention of the present invention is a computer processable medium carrying a program to cause a computer to execute all or part of the state information detection and transmission method according to 56th invention comprising the steps of: detecting the physiological information of a human body; transmitting said detected physiological information; and in a wearable personal information terminal: receiving said physiological information; detecting all or part of the posture, action, and motion state of said human body; and sending all or part of state information composed of said received physiological information and said detected information, or alternatively all or part of state information generated by signal processing of said state information, to a predetermined base station.

The 78th invention of the present invention is a computer processable medium carrying a program to cause a computer to execute all or part of the action detection method according to 65th invention comprising the steps of: acquiring, in the state of being carried with a human body, at least a part of the personal characteristic action information of said human body; acquiring, in the state of being uncarried with said human body and located in a predetermined fixed place, at least a part of the personal characteristic action information of said human body; receiving said personal characteristic action information by wireless; integrally processing said received personal characteristic action information and said personal characteristic action information and thereby obtaining the action state of said human body; comparing said obtained action state with predetermined reference information and thereby determining and predicting the presence or absence of abnormality in said action state of said human body; transmitting the result of said determination, or alternatively said result of determination and said obtained action state information, from a first Internet terminal via the Internet; and receiving said result of determination, or alternatively said result of determination and said action state information, from said first Internet terminal via the Internet by a second Internet terminal.

The 79th invention of the present invention is a personal characteristics information acquisition method comprising the steps of:

Transmitting, by radio wave transmitting means which is located at least at one position in a room, a radio wave of specific frequency;

Receiving, by radio wave receiving means, when the distance from said radio wave transmitting means is a predetermined value or less;

Detecting, by posture/action detecting means, the posture, position, action, and motion state of a human body;

Detecting, by physiological state detecting means, the physiological state such as pulse and heartbeat of said human body;

Transmitting, by sensor signal transmitting means, a sensor signal obtained from said physiological state detecting means;

Receiving, by sensor signal receiving means, a sensor signal obtained from said sensor signal transmitting means;

Transmitting successively and receiving, by a master apparatus, the sensor signals by wireless from a plurality of wearable personal information terminals having said radio wave receiving means, said posture/action detecting means, said sensor signal receiving means, and sensor signal processing means of obtaining the personal characteristics information of said human body; and Processing integrally, by signal processing means, the signals obtained from said sensor signals from said master apparatus by means of a network and thereby obtaining the personal characteristics information of said human body.

The 80th invention of the present invention is a computer processable medium carrying a program to cause a computer to execute all or part of the personal characteristics information acquisition method according to 79th invention comprising the steps of: transmitting, by radio wave transmitting means which is located at least at one position in a room, a radio wave of specific frequency; receiving, by radio wave receiving means, when the distance from said radio wave transmitting means is a predetermined value or less; detecting, by posture/action detecting means, the posture, position, action, and motion state of a human body; detecting, by physiological state detecting means, the physiological state such as pulse and heartbeat of said human body; transmitting, by sensor signal transmitting means, a sensor signal obtained from said physiological state detecting means; receiving, by sensor signal receiving means, a sensor signal obtained from said sensor signal transmitting means; transmitting successively and receiving, by a master apparatus, the sensor signals by wireless from a plurality of wearable personal information terminals having said radio wave receiving means, said posture/action detecting means, said sensor signal receiving means, and sensor signal processing means of obtaining the personal characteristics information of said human body; and processing integrally, by signal processing means, the signals obtained from said sensor signals from said master apparatus by means of a network and thereby obtaining the personal characteristics information of said human body.

The 81st invention of the present invention is an abnormal action detection method comprising the steps of:

Detecting, by position detecting means which is located at least at one position in a room, the position of a human body by means of image processing;

Detecting, by movement direction detecting means which is located in an entrance of said room, the movement direction of said human body;

Transmitting, by transmitting means which is located at least at one position in said room, a radio wave of specific frequency;

Receiving, by receiving means, when the distance from said transmitting means is a predetermined value or less;

Detecting, by posture/action detecting means, the posture, action, and motion state of said human body;

Transmitting successively and receiving, by a master apparatus, the sensor signals by wireless from a plurality of wearable personal information terminals having said receiving means, said posture/action detecting means, and signal processing means of obtaining the action information of said human body;

Processing integrally, by signal processing means, said sensor signals from said master apparatus and the signals obtained from said position detecting means and said movement direction detecting means and thereby obtaining the action information of said human body;

Storing, by storing means, the action information of said human body obtained from said signal processing means, in an integrated form of structured data by means of a network;

Evaluating, by action evaluating means, said action information of said human body obtained from said signal processing means by comparing it with said structured data stored in said storing means connected to said network;

Determining and predicting, by state determining means, an abnormality in the action state of said human body obtained from said action evaluating means; and Notifying, by notifying means, said determined abnormality in said action state of said human body to said personal information terminal and other terminals connected to said network.

The 82nd invention of the present invention is a computer processable medium carrying a program to cause a computer to execute all or part of the abnormal action detection method according to 81st invention comprising the steps of: detecting, by position detecting means which is located at least at one position in a room, the position of a human body by means of image processing; detecting, by movement direction detecting means which is located in an entrance of said room, the movement direction of said human body; transmitting, by transmitting means which is located at least at one position in said room, a radio wave of specific frequency; receiving, by receiving means, when the distance from said transmitting means is a predetermined value or less; detecting, by posture/action detecting means, the posture, action, and motion state of said human body; transmitting successively and receiving, by a master apparatus, the sensor signals by wireless from a plurality of wearable personal information terminals having said receiving means, said posture/action detecting means, and signal processing means of obtaining the action information of said human body; processing integrally, by signal processing means, said sensor signals from said master apparatus and the signals obtained from said position detecting means and said movement direction detecting means and thereby obtaining the action information of said human body; storing, by storing means, the action information of said human body obtained from said signal processing means, in an integrated form of structured data by means of a network; evaluating, by action evaluating means, said action information of said human body obtained from said signal processing means by comparing it with said structured data stored in said storing means connected to said network; determining and predicting, by state determining means, an abnormality in the action state of said human body obtained from said action evaluating means; and notifying, by notifying means, said determined abnormality in said action state of said human body to said personal information terminal and other terminals connected to said network.

DESCRIPTION OF THE REFERENCE NUMERALS

Figure 1:
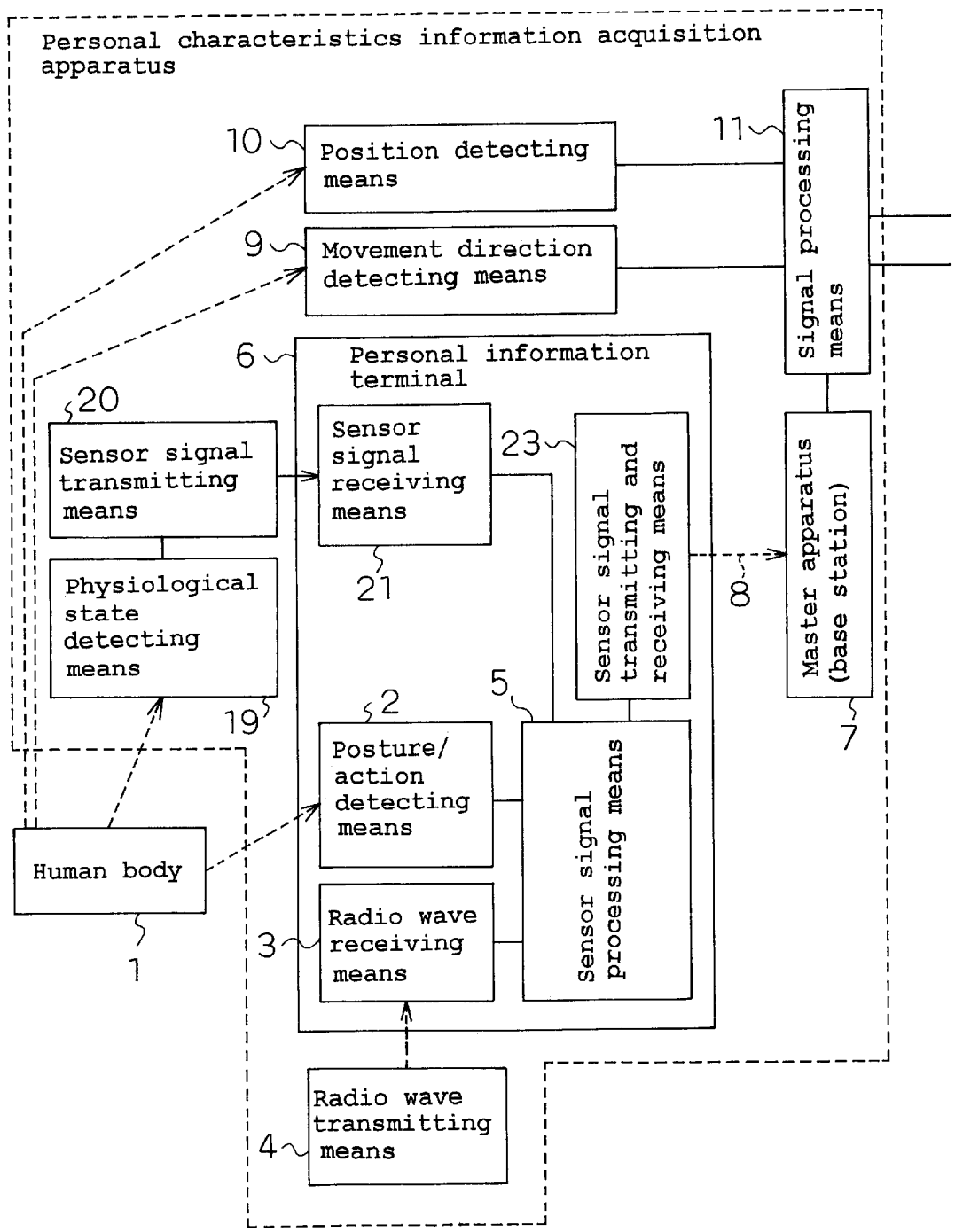
FIG. 1 is a schematic configuration diagram of a personal characteristics information acquisition apparatus according to Embodiment 1 of the invention.

1 Human body
2 Posture/action detecting means
3 Radio wave receiving means
4 Radio wave transmitting means
5 Sensor signal processing means
6 Personal information terminal
7 Master apparatus (base station)
8 Wireless communications
9 Movement direction detecting means
10 Position detecting means
11 Signal processing means
12 Network
13 Data storing means
14 Action evaluating means
15 State determining means
16 Notifying means
19 Physiological state detecting means
20 Sensor signal transmitting means
21 Sensor signal receiving means
23 Sensor signal transmitting and receiving means

PREFERRED EMBODIMENTS OF THE INVENTION

The embodiments of the invention are described below with reference to the drawings.

Embodiment 1

First, the configuration and the operation of a personal characteristics information acquisition apparatus according to Embodiment 1 using a state information acquisition apparatus according to the invention are described below with reference to FIG. 1. The figure is a schematic configuration diagram of the personal characteristics information acquisition apparatus according to the present embodiment. Here, in addition to the configuration and the operation of the personal characteristics information acquisition apparatus according to the present embodiment, described below is an embodiment of a state information acquisition method of the invention.

The personal characteristics information acquisition apparatus according to the present embodiment comprises a group of sensors composed of a personal information terminal 6, movement direction detecting means 9, position detecting means 10, and the like.

The personal information terminal 6 is attached to a human body 1 and comprises: posture/action detecting means 2 of detecting the posture, body motion, action, and motion state of the human body by means of an acceleration sensor, a gyrosensor, or the like; radio wave receiving means 3 of receiving a radio wave of specific frequency transmitted from radio wave transmitting means 4 when the distance from the radio wave transmitting means 4 is a predetermined value (for example, 1 m) or less; sensor signal receiving means 21 of receiving a sensor signal transmitted from sensor signal transmitting means 20 attached to physiological information detecting means 19 attached to the human body; sensor signal processing means 5 of processing the signals obtained from the sensors; and sensor signal transmitting and receiving means 23 of transmitting the sensor signals to a base station (referred to as a master apparatus) 7 by wireless communications 8.

The movement direction detecting means 9 provides a sensor output corresponding to the movement direction of the human body 1 by means of an infra-red sensor, a distance sensor, or the like. The sensor signal output from the movement direction detecting means 9 is processed by signal processing means 11, thereby permitting the determination of the movement direction of entering or exiting the room by the human body 1.

The position detecting means 10 is either (1) means of detecting and specifying the position of the human body 1 by means of image processing using a CCD camera, an infra-red sensor, or an infra-red camera, the latter two being capable of measuring the two-dimensional temperature distribution, or (2) means of specifying the position of the human body 1 by means of: a radio wave source attached to the human body 1; and one or more antennas which are located in the room and detect the intensity or the direction of the radio wave. The position detecting means 10 uses signal processing means 11 to process the signal obtained from the CCD camera, the infra-red sensor, or the antennas, thereby obtaining the two-dimensional coordinates on the floor of the room.

In the present embodiment, the human body 1 is identified substantially at the instance of entering the room, and the tracking of the identified human body 1 is continued.

For example, when one or more antennas located in the room are used, (a) the direction of the human body 1 viewed from each antenna is obtained from the direction of the radio wave received by the antenna, and (b) the distance of the human body 1 from each antenna is obtained from the intensity of the radio wave received by the antenna. This permits the specification of the two-dimensional position of the human body 1. In case of a plurality of antennas, the precision in such position specification is improved, and further the position of the human body 1 can be specified on the basis of the principles of trigonometrical measurement without using the radio wave intensity.

Further, in case of an infra-red sensor or the like, data acquisition is carried out approximately in every 1 sec. In case of the data acquisition with the repetition period of this order, since the human body 1 does not move very fast, two human bodies the movement distance of which within the repetition period are determined as an identical one. Further, the data is interpolated. In this approach, the movement path of the human body 1 can be sufficiently analyzed and tracked. Here, with the recent improvement of the performance of the infra-red sensor or the like, a plurality of human bodies can be sufficiently discriminated when the human bodies are separated from each other by approximately 10 cm or more.

As such, identification is carried out at the instance of entering the room, and tracking is continued after that. This approach permits the identification and the position detection of each human body even when a plurality of human bodies exist in a room.

The base station 7 receiving the sensor information of the personal information terminal 6 by wireless communications 8 is connected to the signal processing means 11 which is connected to both the movement direction detecting means 9 and the position detecting means 10. Accordingly, the information can be integrated. Here, in case without both the movement direction detecting means 9 and the position detecting means 10, the information corresponding to that obtained by these means may be detected as personal information by the personal information terminal 6, and then transmitted from the personal information terminal 6 to the base station 7.

Here, the detection signal transmitting means according to the invention corresponds to the means having the sensor signal transmitting and receiving means 23. The signal receiving and processing means according to the invention corresponds to the means having the base station (also referred to as a master apparatus) 7 and the signal processing means 11. The position detecting means according to the invention corresponds to the means having the position detecting means 10. The identifying means according to the invention corresponds to the means having the sensor signal processing means 5. The receiving means according to the invention corresponds to the means having the base station (also referred to as a master apparatus) 7. The signal processing and outputting means according to the invention corresponds to the means having the signal processing means 11. The state information according to the invention corresponds to the action information according to the present embodiment.

Embodiment 2

The configuration and the operation of a personal characteristics information acquisition system according to Embodiment 2 using a state information acquisition system according to the invention are described below with reference to FIG. 2. The figure is a schematic configuration diagram of the personal characteristics information acquisition system according to the present embodiment. Here, in addition to the configuration and the operation of the personal characteristics information acquisition system according to the present embodiment, described below is an embodiment of a state information acquisition method of the invention.

The personal characteristics information acquisition system according to the present embodiment comprises a network 12, data storing means 13, action evaluating means 14, state determining means 15, notifying means 16, and the above-mentioned personal characteristics information acquisition apparatus according to Embodiment 1.

The action information of human body integrated by the signal processing means 11 is transferred via the network 12 to the data storing means 13, and stored as structured data in the data storing means 13.

The action information of human body obtained from the signal processing means 11 undergoes comparison and evaluation in the action evaluating means 14 on the basis of the structured data having been accumulated in the data storing means 13 to date. When the action state of human body obtained from the action evaluating means 14 is determined to be abnormal or predicted to become abnormal as a possibility in the future by the state determining means 15, the notifying means 16 notifies it to the person.

As such, the signal processing means 11, together with other signal processing means (not shown) in other rooms, is connected to the network 12. Accordingly, the information in every room can be used in common, whereby the action state of the person in every room can be understood.

When a displaying apparatus such as monitor is provided as an auxiliary apparatus to the state determining means 15, the action state of the person in every room can be viewed at one time. This reduces substantially the load on helpers in an ordinary home as well as in an institution for the nursing care of elderlies. In the present embodiment, the kind of the network is not restricted, and the network may be a telephone network, the Internet, a dedicated in-home network, or the like.

The comparing and determining means according to the invention corresponds to the means having the action evaluating means 14 and the state determining means 15.

Figure 3:
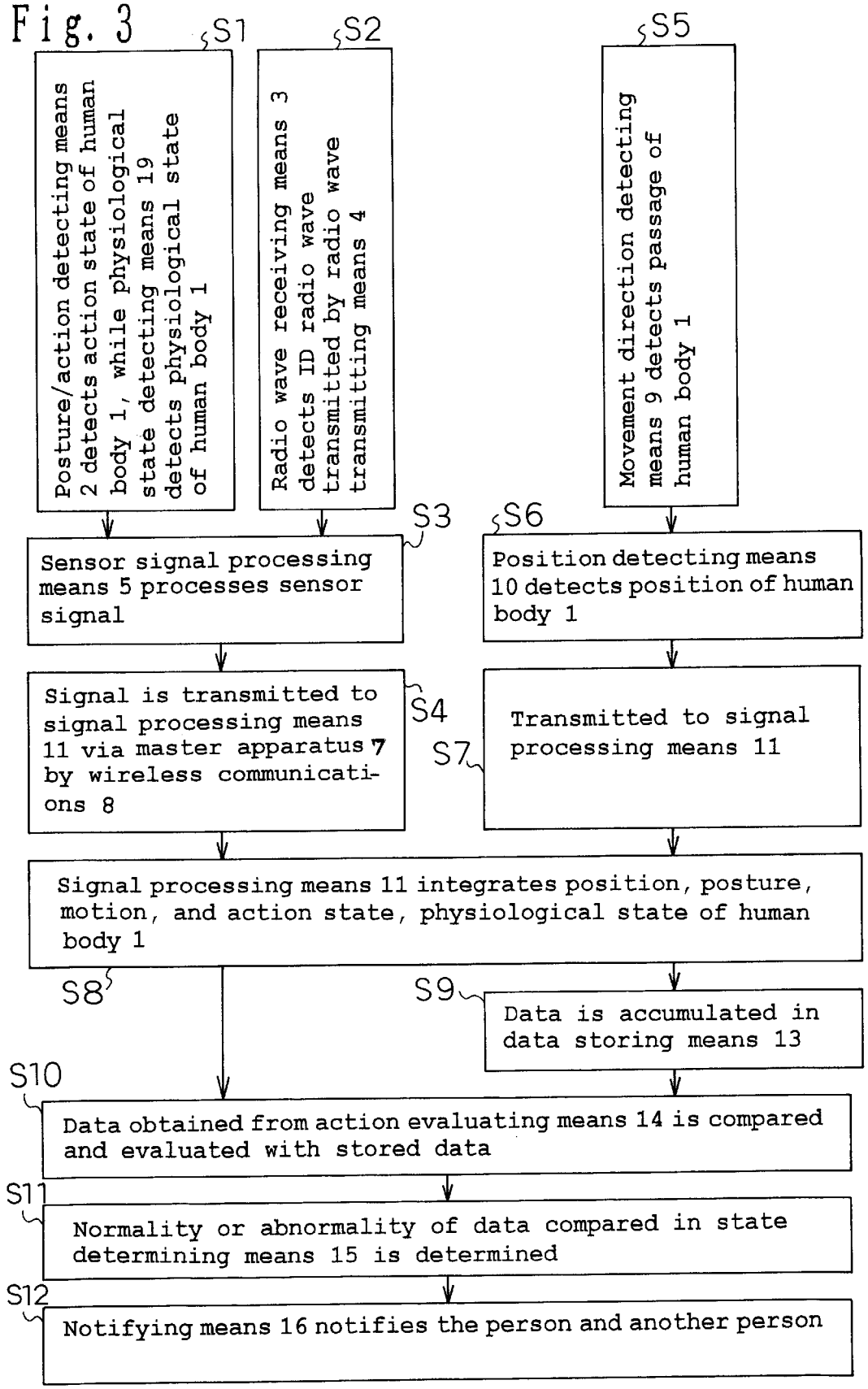
FIG. 3 is an operation diagram of a personal characteristics information acquisition system according to Embodiment 2 of the invention.

The operation of the personal characteristics information acquisition system according to the present embodiment is described below in detail with reference to FIG. 3. The figure is an illustrative diagram of the operation of the personal characteristics information acquisition system.

When the human body 1 carries the personal information terminal 6, the posture/action detecting means 2 composed of an acceleration sensor or the like continuously monitors the action state of the human body 1, while the physiological state detecting means 19 continuously monitors the physiological state (S1).

When the human body 1 begins to enter the room, the radio wave receiving means 3 in the personal information terminal 6 begins to receive the ID radio wave of specific frequency from the radio wave transmitting means 4. With the continuation of entering the room, the personal information terminal 6 goes into the reception region of the radio wave receiving means 3, whereby the ID radio wave is detected (S2). The sensor signal processing means 5 processes the sensor signals detected by the posture/action detecting means 2 and physiological state detecting means 19 (S3). These sensor signals are transmitted from the sensor signal transmitting and receiving means 23, through the master apparatus 7 of base station, and to the signal processing means 11 by wireless communications 8 (S4).

In the sensor signal processing means 5, the sensor signal transmitting and receiving means 23 transmits a radio wave of a frequency specific to each terminal, and the signal processing means 11 receives the radio wave via the master apparatus 7 (see FIG. 1), thereby recognizing the personal information terminal 6. As such, the human body 1 is identified.

On the other hand, when the human body 1 approaches the entrance of the room, the movement direction detecting means 9 composed of a pyroelectric one-dimensional array device having a plurality of light receiving sections detects the passage of the human body 1 (S5), and recognizes the start of the passage through the entrance. With the continuation of entering the room, the position detecting means 10 according to visible-light image processing using a CCD camera detects the position of the human body 1 (S6). The action information of the human bodies 1 is transmitted to the signal processing means 11 (S7).

The sensor information transmitted from the personal information terminal 6 to the base station 7 by wireless communications 8 is sent to the signal processing means 11 having the data of the movement direction detecting means 9 and the position detecting means 10, whereby the information is integrated by the signal processing means 11 (S8).

The action information of the human body 1 integrated by the signal processing means 11 is input to the data storing means 13 via the network 12, and stored as structured data (S9).

The action information of the human body 1 obtained from the sensor signal processing means 5 undergoes comparison and evaluation in the action evaluating means 14 on the basis of the structured data having been accumulated in the data storing means 13 to date (S10). When the action state of the human body 1 obtained from the action evaluating means 14 is determined to be abnormal or predicted to become abnormal as a possibility in the future by the state determining means 15 (S11), the notifying means 16 notifies it to the person or another person (S12).

Figure 6:
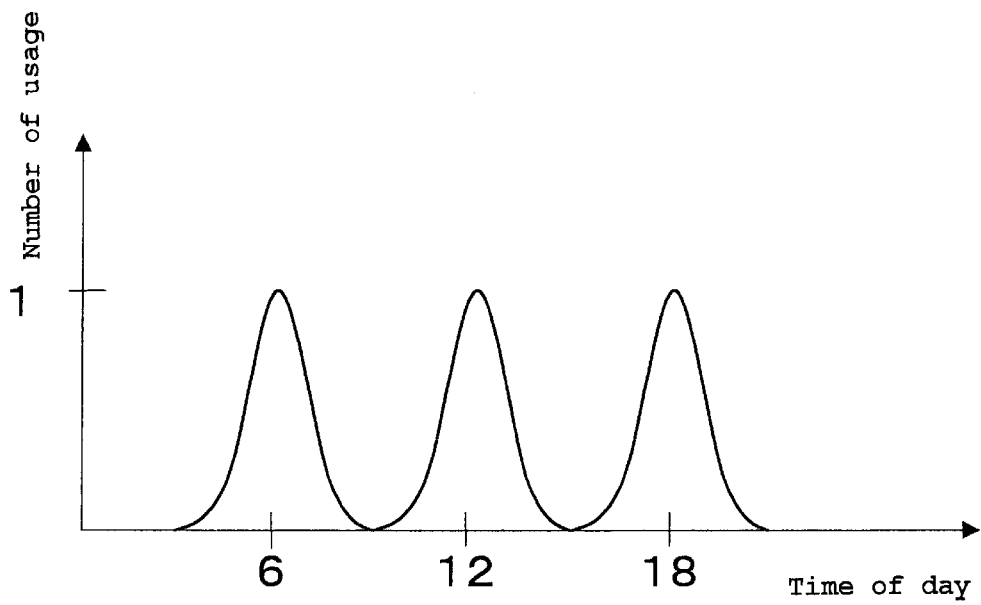
FIG. 6 is a diagram showing: the average relation between the time of day and the number of lavatory usage (FIG. 6(a)); and the average relation between the number of lavatory usage and the number of days (FIG. 6(b)); respectively, prepared from the analysis of the records in a month.
Figure 6:
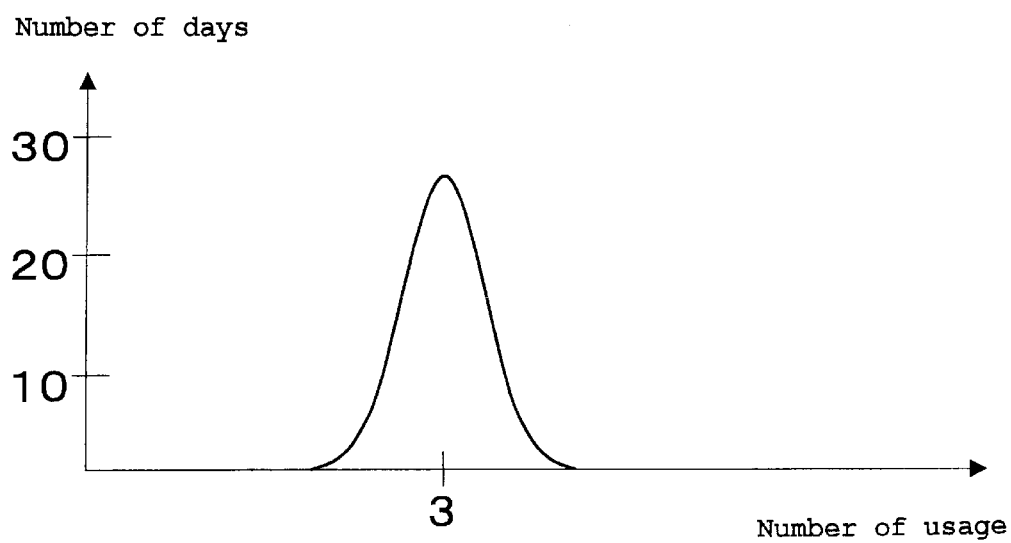

Described below are specific examples of the above-mentioned structured data, the comparison and evaluation by the action evaluating means 14, and the determination by the state determining means 15. For example, the movement direction detecting means 9 and the position detecting means 10 are located in a lavatory for an elderly. The data from these means is processed by the signal processing means 11, and then stored as a part of the above-mentioned structured data in the data storing means 13. FIGS. 6(a) and 6(b) are diagrams showing: the average relation between the time of day and the number of lavatory usage; and the average relation between the number of lavatory usage and the number of days; respectively, prepared as structured data from the analysis of the records in a month.

The action evaluating means 14 compares the obtained state information with the above-mentioned structured data, whereby the state determining means 15 determines that (1) the number of lavatory usage in a day has increased, (2) the time interval between lavatory usage has become short, or the like. As such, the life pattern of the elderly is understood. This information can be useful in various applications such as the early-stage detection and the treatment of diseases.

Embodiment 3

Figure 4:
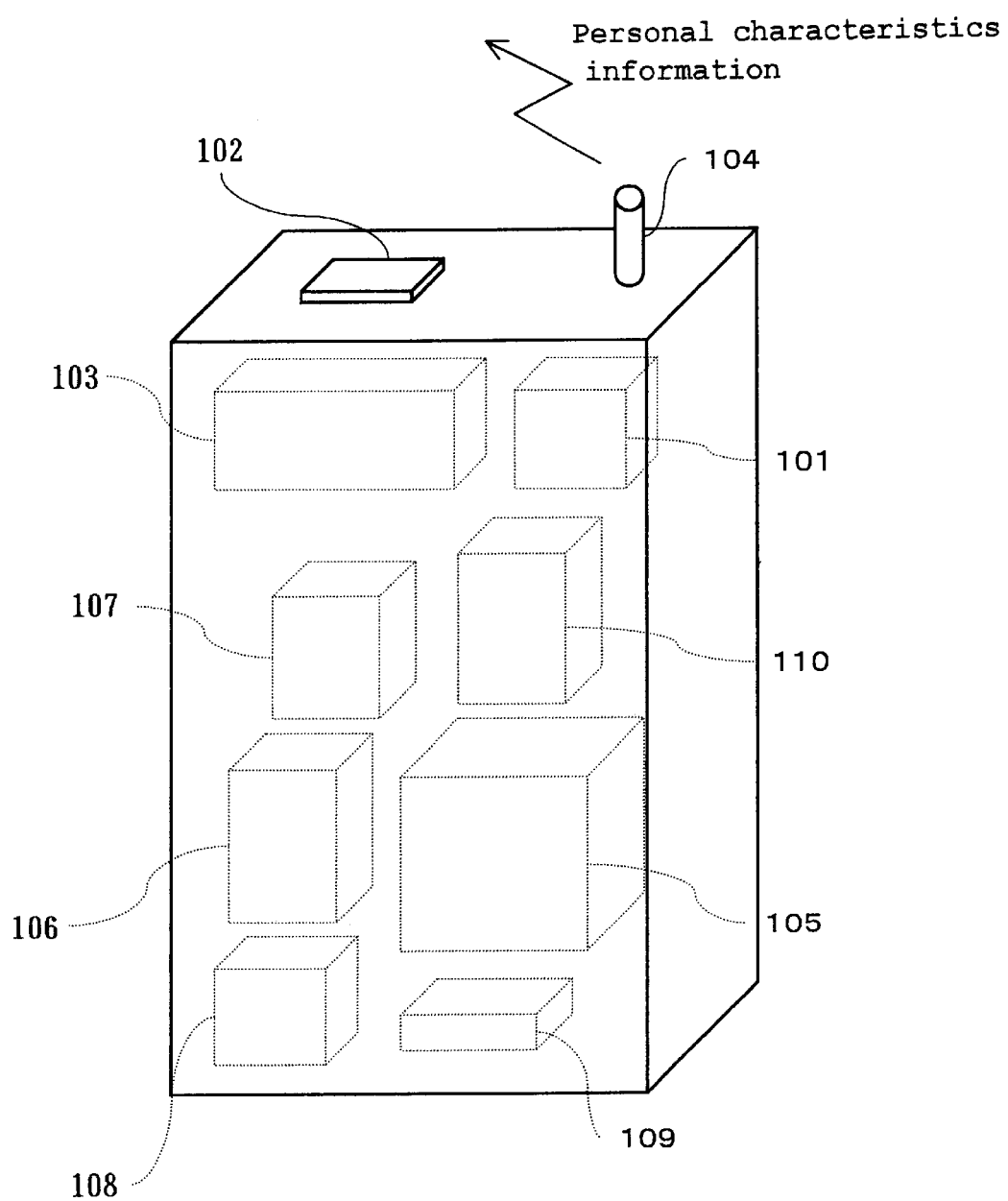
FIG. 4 is a schematic diagram of a personal information terminal according to Embodiment 3 of the invention.

The configuration and the operation of a personal information terminal according to Embodiment 3 using an attachable terminal apparatus according to the invention are described below with reference to FIG. 4. The figure is a schematic configuration diagram of the personal information terminal according to the present embodiment. Here in addition to the configuration and the operation of the personal information terminal according to the present embodiment, described below is an embodiment of a state information acquisition method of the invention.

The personal information terminal according to the present embodiment is attached to a part of a human body, for example, to the waist using a belt, thereby detecting the posture, the state of walking, the movement path, and the like using an acceleration sensor 103, a gyrosensor 110, and the like.

As for the posture, the inclination of the human body is obtained by measuring the force component of the gravity using the triaxial acceleration sensor 103. For the state of walking, the gravity direction output from the gyrosensor 110 is analyzed by a sensor signal processing circuit 105, whereby it is determined that the state is static or walking, and that the state of walking is upstairs or downstairs.

Figure 2:
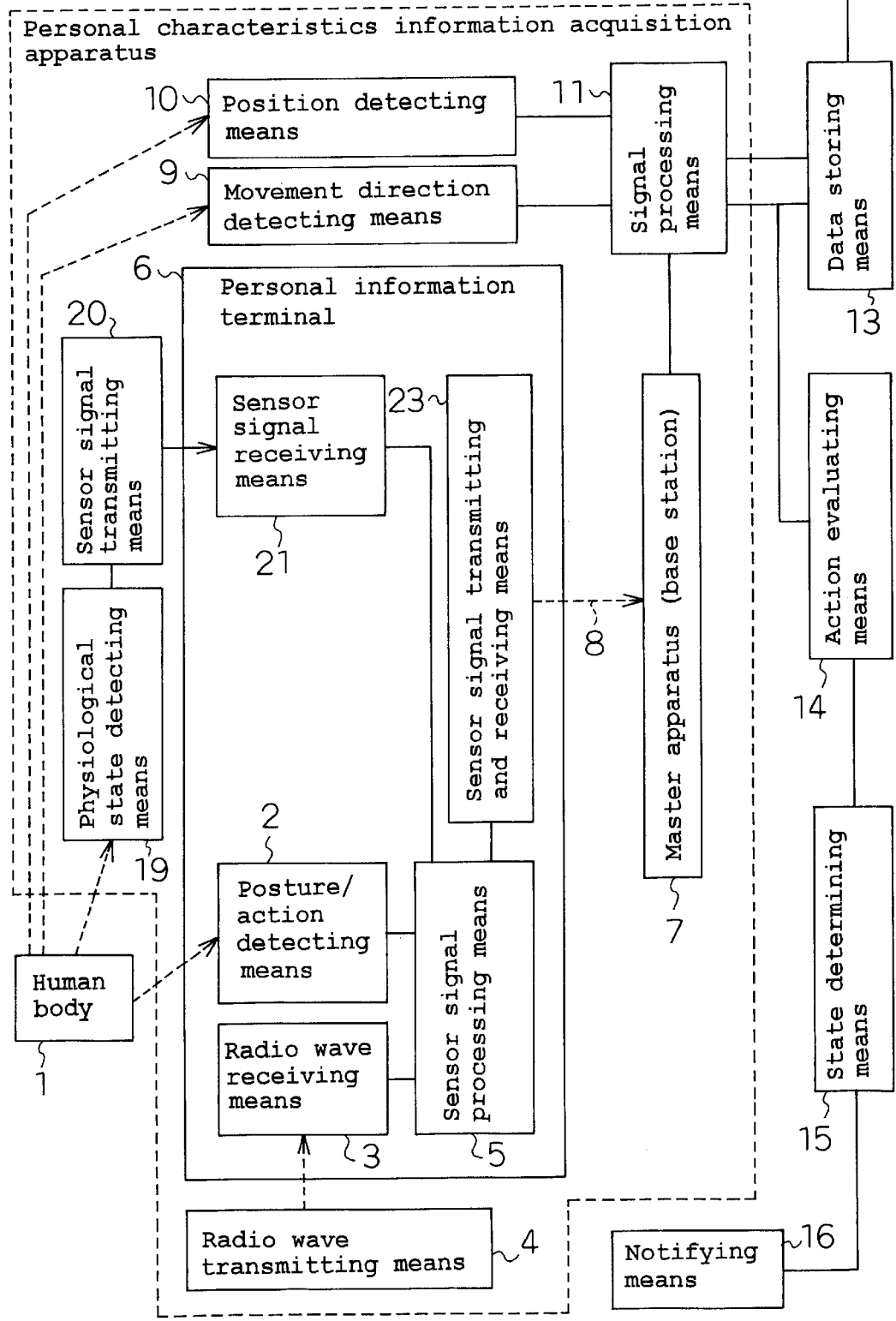
FIG. 2 is a schematic configuration diagram of a personal characteristics information acquisition system according to Embodiment 2 of the invention.

A coil 108 receives the radio wave transmitted from the radio wave transmitting means 4 (see FIG. 2). The signal is transformed into position information by the sensor signal processing circuit 105. A sensor signal receiving means 109 receives the physiological signal transmitted from the sensor signal transmitting means 20 (see FIG. 2) attached to physiological state detecting means 19. The signal is transformed into heartbeat rate and the like by the sensor signal processing circuit 105.

These signals are analyzed into various state information by the sensor signal processing circuit 105. The results are transmitted as personal characteristics information through a transmitting and receiving section 101, through an antenna 104, and to the base station 7 (see FIG. 2).

When there has been no human body movement for a long time, or when an abnormal state is detected, determined, or predicted, an alarm buzzer 107 calls the person carrying this apparatus. This alarm buzzer is invoked by a signal input through the antenna 104 and the transmitting and receiving section 101 by wireless. When there is no response, for example, by pushing a switch 102, to this call, an abnormal state signal is transmitted through the antenna 104. When the abnormal state signal is transmitted, a helper checks the situation of the person, and/or the situation is notified to the outside.

All the above-mentioned means are powered by an internal battery 106.

The present embodiment has been described for the case of an acceleration sensor. However, the invention is not restricted to this, and the posture information may be obtained by an inclination angle sensor.

Figure 5:
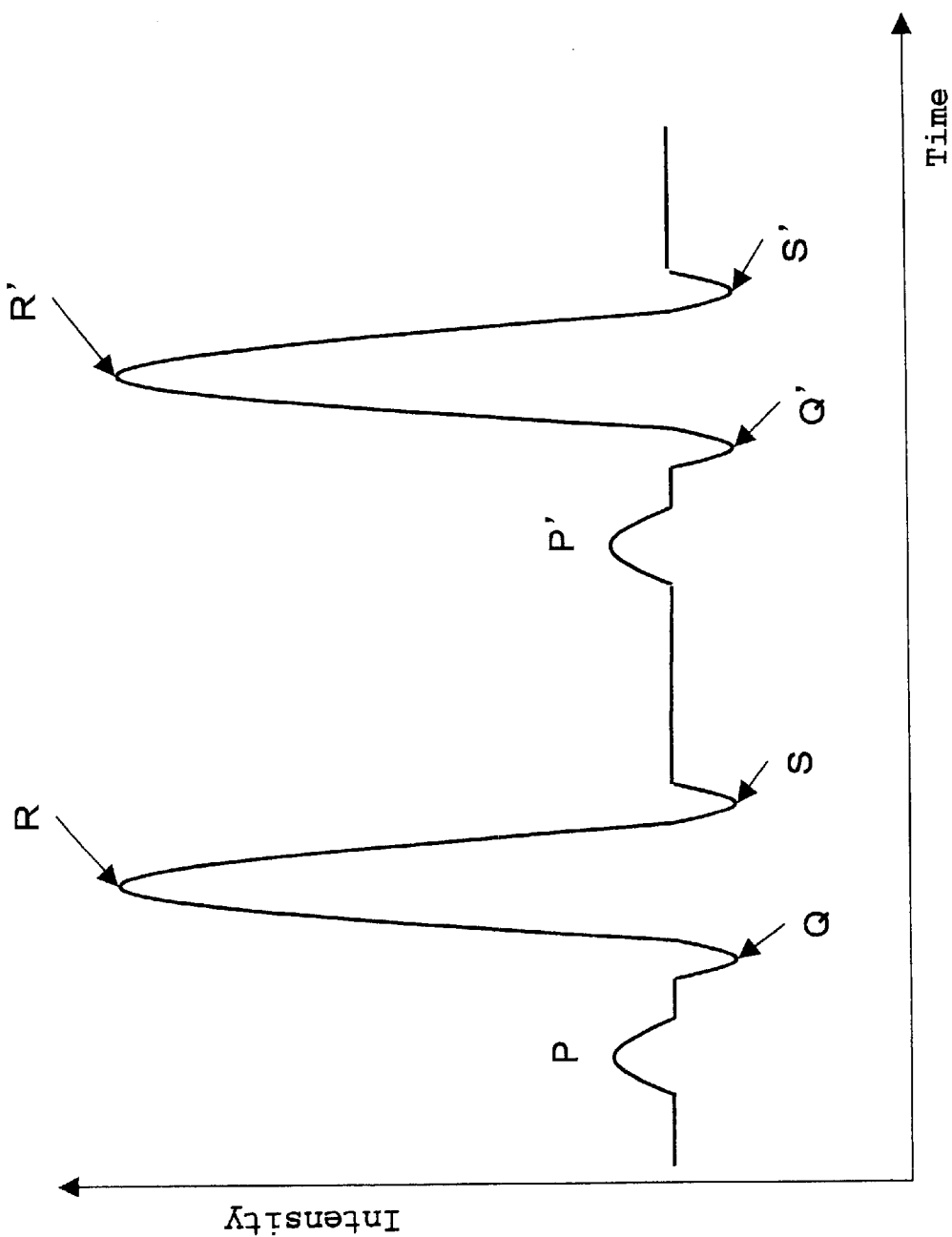
FIG. 5 is a diagram showing the time-dependent intensity change in heartbeat used in the description of Embodiment 3 of the invention.

The operation of the personal information terminal according to the present embodiment is described below with reference to FIG. 5. The figure is an illustrative diagram of the time change in heartbeat intensity.

The analogue signal such as the pulse obtained by the physiological state detecting means 19 (see FIG. 2) is transmitted from the sensor signal transmitting means 20 (see FIG. 2). The transmitted analogue physiological signal is received by the sensor signal receiving means 109 (see FIG. 4) built in the personal information terminal, thereby being transformed into the time change in the heartbeat intensity as shown in FIG. 5.

P and P' denote electric excitation processes indicating the contraction of the atriums, while QRS and Q'R'S' denote electric excitation processes indicating the contraction of the right and left ventricles. Time interval RR' is approximately 1 sec.

The signal undergoes amplification, noise elimination, and A/D conversion in the sensor signal processing circuit 105 (see FIG. 4), whereby accurate heartbeat and heartbeat rate are obtained as personal information. For example, the detection of the time interval between the heartbeats permits the detection of an abnormal state.

As described above, the present invention provides, for example, a personal characteristics information acquisition method comprising: radio wave transmitting means which is located at least at one position in a room and transmits a radio wave of specific frequency; radio wave receiving means of receiving when the distance from said radio wave transmitting means is a predetermined value or less; posture/action detecting means of detecting the posture, action, and motion state of a human body; physiological state detecting means of detecting the physiological state such as pulse and heartbeat of said human body; sensor signal transmitting means of transmitting a sensor signal obtained from said physiological state detecting means; sensor signal receiving means of receiving a sensor signal obtained from said sensor signal transmitting means; and a wearable personal information terminal having said radio wave receiving means, said posture/action detecting means, said sensor signal receiving means, and sensor signal processing means of obtaining the personal characteristics information of said human body.

Further, the present invention provides, for example, a personal characteristics information acquisition apparatus comprising: radio wave transmitting means which is located at least at one position in a room and transmits a radio wave of specific frequency; radio wave receiving means of receiving when the distance from said radio wave transmitting means is a predetermined value or less; posture/action detecting means of detecting the posture, action, and motion state of a human body; physiological state detecting means of detecting the physiological state such as pulse and heartbeat of said human body; sensor signal transmitting means of transmitting a sensor signal obtained from said physiological state detecting means; sensor signal receiving means of receiving a sensor signal obtained from said sensor signal transmitting means; a wearable personal information terminal having said radio wave receiving means, said posture/action detecting means, said sensor signal receiving means, and sensor signal processing means of obtaining the personal characteristics information of said human body; a master apparatus for successively transmitting and receiving the sensor signals from a plurality of said wearable personal information terminals by wireless; and signal processing means of integrally processing the signals obtained from said sensor signals from said master apparatus and thereby obtaining the personal characteristics information of said human body.

Furthermore, the present invention provides, for example, a personal characteristics information acquisition system comprising: radio wave transmitting means which is located at least at one position in a room and transmits a radio wave of specific frequency; radio wave receiving means of receiving when the distance from said radio wave transmitting means is a predetermined value or less; posture/action detecting means of detecting the posture, position, action, and motion state of a human body; physiological state detecting means of detecting the physiological state such as pulse and heartbeat of said human body; sensor signal transmitting means of transmitting a sensor signal obtained from said physiological state detecting means; sensor signal receiving means of receiving a sensor signal obtained from said sensor signal transmitting means; a wearable personal information terminal having said radio wave receiving means, said posture/action detecting means, said sensor signal receiving means, and sensor signal processing means of obtaining the personal characteristics information of said human body; a master apparatus for successively transmitting and receiving the sensor signals from a plurality of said wearable personal information terminals by wireless; and signal processing means of integrally processing, by means of a network, the signals obtained from said sensor signals from said master apparatus and thereby obtaining the personal characteristics information of said human body.

Further, the present invention may be, for example, a personal characteristics information acquisition system further comprising the above-mentioned signal processing means of integrally processing, by means of a network, the signals obtained from: position detecting means which is located at least at one position in a room and detects and specifies the position of the human body by means of image processing; and movement direction detecting means which is located in the entrance of the room and detects the movement direction of the human body.

Further, the present invention may be, for example, a personal characteristics information acquisition system wherein said physiological state detecting means and said sensor signal transmitting means are integrated into one piece and contact the human body thereby to detect and transmit said physiological state, whereby the information is integrated by means of a network and then processed by said signal processing means, and whereby the personal characteristics information of the human body is obtained.

Furthermore, the present invention provides, for example, a personal characteristics information acquisition system comprising: position detecting means which is located at least at one position in a room and detects the position of a human body by means of image processing; movement direction detecting means which is located in an entrance of said room and detects the movement direction of said human body; radio wave transmitting means which is located at least at one position in said room and transmits a radio wave of specific frequency; radio wave receiving means of receiving when the distance from said radio wave transmitting means is a predetermined value or less; posture/action detecting means of detecting the posture, position, action, and motion state of a human body; physiological state detecting means of detecting the physiological state such as pulse and heartbeat of said human body; sensor signal transmitting means of transmitting a sensor signal obtained from said physiological state detecting means; sensor signal receiving means of receiving a sensor signal obtained from said sensor signal transmitting means; a wearable personal information terminal having said radio wave receiving means, said posture/action detecting means, said sensor signal receiving means, and sensor signal processing means of obtaining the personal characteristics information of said human body; a master apparatus for successively transmitting and receiving the sensor signals from a plurality of said wearable personal information terminals by wireless; signal processing means of integrally processing the signals obtained from said sensor signals from said master apparatus and the signals obtained from said position detecting means and said movement direction detecting means, and thereby obtaining the personal characteristics information of said human body; storing means of storing the action information of said human body obtained from said signal processing means, in an integrated form of structured data by means of a network; action evaluating means of evaluating said action information of said human body obtained from said signal processing means by comparing it with said structured data stored in said storing means connected to said network; state determining means of determining and predicting an abnormality in the action state of said human body obtained from said action evaluating means; and notifying means of notifying said determined abnormality in said action state of said human body to said personal information terminal and other terminals connected to said network.

According to the personal characteristics information acquisition apparatus of the invention having the above-mentioned configuration, a human body entering a room can be identified. Further, the action and the personal characteristics information of the human body, such as in-room position, posture, action information, and physiological information, can be measured accurately. Further, state determining means attached to the human body communicates with the base station by wireless, and the base station is connected to the network. This permits integrated management of the personal characteristics information of human bodies in a plurality of rooms or specified areas. Accordingly, the action of the human bodies in the whole building can be understood in real time. This permits various applications such as abnormality detection, air conditioning/illumination control, and security.

In the present embodiment, the detection of physiological state and the detection of posture and/or action state according to the invention have been applied to the human body 1 (that is, a person). However, the invention is not restricted to this, and may be applied to an animal.

Further, in the present embodiment, the physiological state in the invention has been pulse, heartbeat, or the like. However, the physiological state in the invention is not restricted to this, and may be blood pressure, body temperature, oxygen concentration in blood, or sweating state.

Furthermore, in the present embodiment, the detection of physiological state according to the invention has been carried out at the same time as the detection of posture and/or action state. However, the invention is not restricted to this, and the detection of physiological state according to the invention (1) may be carried out together with, for example, the detection of the position of the person or animal and/or the identification of the person or animal, and (2) may be carried out solely.

Further, in the present embodiment, the physiological state detecting means according to the invention has been provided separately from the personal information terminal 6. However, the invention is not restricted to this, and the physiological state detecting means according to the invention may be built in the attachable terminal apparatus according to the invention. Alternatively, the physiological state detecting means according to the invention may be integrated in a common case together with the detection signal transmitting means according to the invention.

Further, in the present embodiment, the posture/action detecting means according to the invention has been built in the personal information terminal 6. However, the invention is not restricted to this, and the posture/action detecting means according to the invention may be provided separately from the attachable terminal apparatus.

Further, in the present embodiment, the transmission of the detection signals based on the detection of (1) the physiological state and (2) the posture and/or action state has been carried out on the basis of the fact that the radio wave transmitted by the radio wave transmitting means 4 is received by the radio wave receiving means 3 when the distance from the radio wave transmitting means 4 is a predetermined value or less. However, the invention is not restricted to this, and the transmission of these detection signals may be carried out always, or alternatively, periodically on the basis of predetermined rules. However, obviously, in case that the transmission and reception of the detection signals is carried out when the distance from the radio wave transmitting means 4 is a predetermined value or less, as in the present embodiment, the state information of the human body 1 during the stay in the room is acquired efficiently.

Further, in the present embodiment, when the state information is obtained according to the invention, having been considered are: the position of the person or animal obtained by the position detecting means 10 of detecting the position of the person or animal; and the movement direction detected by the movement direction detecting means 9 of detecting the movement direction of the person or animal. However, the invention is not restricted to this, and it may be omitted to consider the position and/or the movement direction of the person or animal in obtaining the state information according to the invention. In this case, the position detecting means and/or the movement direction detecting means according to the invention are unnecessary.

Further, in the present embodiment, the predetermined region in the invention has been a room in which the base station (also referred to as a master apparatus) 7, the signal processing means 11, and the like have been located. However, the invention is not restricted to this, and the predetermined region in the invention may be a region in a garden or an elevator. In this case, obviously, when the radio wave transmitting means 4, the base station (also referred to as a master apparatus) 7, the signal processing means 11, and the like are located in each region, the state information is acquired more efficiently.

Further, in the present embodiment, the state information acquisition system according to the invention has comprised: data storing means 13 of storing the structured data; action evaluating means 14 of evaluating the obtained action information by comparing it with the structured data; state determining means 15 of determining the normality or abnormality in the person on the basis of the result of the evaluation; and notifying means 16 of notifying the abnormality, when so determined. However, the invention is not restricted to this, and the state information acquisition system according to the invention may be configured without these means. In this case, for example, the acquired state information may be displayed always on a monitor, and the notification of the abnormality may be processed by manual operation by a person watching the monitor.

Further, in the present embodiment, the storing means according to the invention has stored the structured data generated by accumulating the action information of the human body 1. However, the invention is not restricted to this, and the storing means according to the invention may store the state information obtained from the result of processing and/or standard information having been prepared previously. Further, the storing means according to the invention may store more detailed structured data corresponding to each human body generated by correcting the previously input information of a standard human body with the state information continuously accumulated for each human body of object of detection. In this case, (1) when the accumulation of the state information is not yet sufficient; the data mainly based on the previously input information is used, while (2) when the accumulation of the state information is sufficient, the above-mentioned detailed and corrected structured data is used. Then, the state information is compared with the predetermined reference. This approach permits more appropriate determination of the normality or abnormality in the person or animal of object of detection.

Further, in the present embodiment, the processing of detected signals according to the invention has been carried out by: the sensor signal processing means 5 on the transmission side (that is, on the side of the terminal); and the signal processing means 11 on the reception side (that is, on the side opposite to the terminal). However, the invention is not restricted to this, and the processing of detected signals according to the invention may be carried out, for example, (1) substantially only on the reception side, (2) substantially only on the transmission side when no position detection is carried out on the side opposite to the terminal, or (3) substantially by a dedicated information processing apparatus provided on the side of the data storing means according to the invention. In this case, the timing of the processing affects slightly the timing of obtaining the state information according to the present invention.

Further, in the present embodiment, the state information acquisition system according to the invention has comprised movement direction detecting means 9. However, the invention is not restricted to this, and the state information acquisition system according to the invention may be configured without movement direction detecting means.

Further, in the present embodiment, the identification of the person or animal according to the invention has been carried out by: the sensor signal transmitting and receiving means 23 transmitting a radio wave of a frequency specific to the personal information terminal 6 carried with the human body 1; and the signal processing means 11 receiving the radio wave and thereby recognizing the personal information terminal 6. However, the invention is not restricted to this, and the identification of the person or animal according to the invention may be carried out by extracting characteristic quantities such as the face from a CCD image shot by a CCD camera.

Further, in the present embodiment, the identification of the person or animal according to the invention has been applied to a single human body 1. Further, in the present embodiment, even in case of a plurality of persons or animals, the identification of the person or animal according to the invention (1) can be applied to the plurality of persons or animals by performing the above-mentioned identification process to each person or animal, or (2) is unnecessary when each attachable terminal apparatus according to the invention is carried with a single person or animal.

Furthermore, the present invention provides a personal characteristics information acquisition apparatus comprising: radio wave transmitting means of transmitting a radio wave of specific frequency; radio wave receiving means; posture/action detecting means; physiological state detecting means; sensor signal transmitting means; sensor signal receiving means; a wearable personal information terminal having said radio wave receiving means, said posture/action detecting means, said sensor signal receiving means, and sensor signal processing means of obtaining the personal characteristics information of the human body; a master apparatus for successively transmitting and receiving the sensor signals from a plurality of said wearable personal information terminals by wireless; and signal processing means of integrally processing, by means of a network, the signals obtained from said sensor signals from said master apparatus and thereby obtaining the personal characteristics information of said human body. According to this configuration, a human body entering a room can be identified. Further, the action and the personal characteristics information of the human body, such as in-room position, posture, action information, and physiological information, can be measured accurately. In particular, because the action state and the physiological state of the human body are integrated, more detailed personal characteristics information is obtained. Further, state determining means attached to the human body communicates with the base station by wireless, and the base station is connected to the network. This permits integrated management of the personal characteristics information of human bodies in a plurality of rooms or specified areas. Accordingly, the action of the human bodies in the whole building can be understood in real time. This permits various applications such as abnormality detection, air conditioning/illumination control, and security.

As such, the human body is identified, and the position of the human body is specified. Further, the posture, action, motion state, and physiological state of the human body are specified. Furthermore, the personal characteristics information of a plurality of human bodies can be integrated by a network. Accordingly, a personal characteristics information acquisition method according to the invention, and an apparatus and a system using the same permit easy, accurate, reliable, and inexpensive personal characteristics information acquisition, thereby substantially contributing to the expansion of home information infrastructure business.

As described above, according to the invention, the state of a person can be obtained with considering the physiological information of the person. This is useful information for the above-mentioned application. For example, in the prior art permitting the detection of only the posture and the motion state of the person, when the person is on bed, the person has been considered to be normal, regardless of the real situation. However, in the invention permitting the detection of also the physiological state of the person, for example, when a rise in the heartbeat rate is detected, the person on bed can be determined to be abnormal.

Embodiment 4

Figure 7:
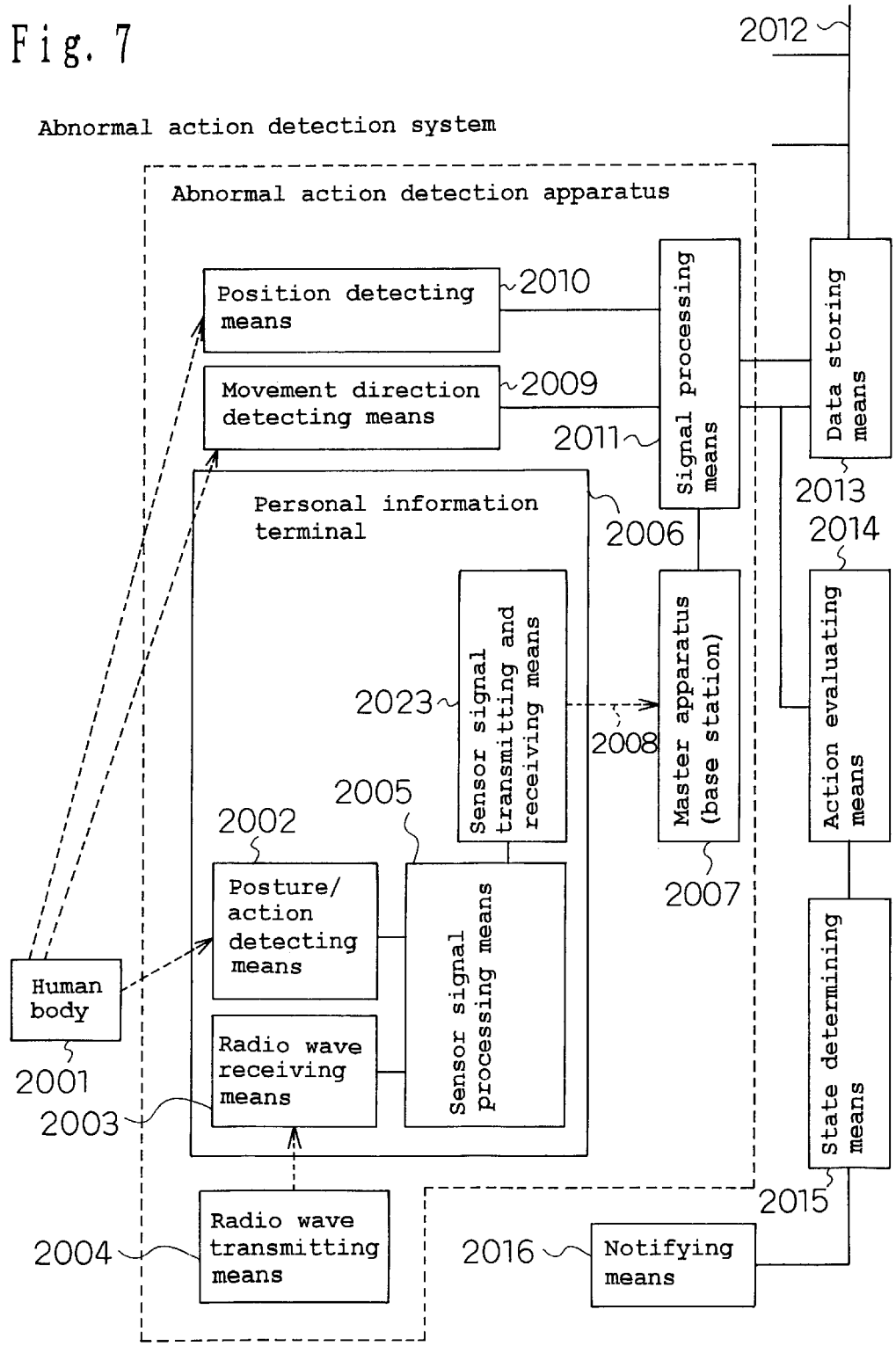
FIG. 7 is a schematic configuration diagram of an abnormal action detection system according to Embodiment 4 of the invention.

First, the configuration and the operation of an abnormal action detection system according to Embodiment 4 using a state information acquisition system according to the invention are described below with reference to FIG. 7. The figure is a schematic configuration diagram of the abnormal action detection system according to the present embodiment. Here, in addition to the configuration and the operation of the abnormal action detection system according to the present embodiment, described below is an embodiment of a state information acquisition method of the invention.

The abnormal action detection system according to the present embodiment comprises a network 2012, data storing means 2013, action evaluating means 2014, state determining means 2015, notifying means 2016, and an abnormal action detection apparatus.

The abnormal action detection apparatus according to the present embodiment comprises a group of sensors composed of a personal information terminal 2006, movement direction detecting means 2009, position detecting means 2010, and the like.

The personal information terminal 2006 is attached to a human body 2001 and comprises: posture/action detecting means 2002 of detecting the posture, body motion, action, and motion state of the human body by means of an acceleration sensor, a gyrosensor, or the like; radio wave receiving means 2003 of receiving a radio wave of specific frequency transmitted from radio wave transmitting means 2004 when the distance from the radio wave transmitting means 2004 is a predetermined value (for example, 1 m) or less; sensor signal processing means 2005 of processing the signals obtained from the sensors; and sensor signal transmitting and receiving means 2023 of transmitting these sensor signals to a base station 2007 by wireless.

The movement direction detecting means 2009 provides a sensor output corresponding to the movement direction of the human body or article by means of an infra-red sensor, a distance sensor, or the like. The sensor signal output from the movement direction detecting means 2009 is processed by signal processing means 2011, thereby permitting the determination of the movement direction of entering or exiting the room by the human body or article.

The position detecting means 2010 is either means of detecting and specifying the position of the human body by means of image processing using a CCD camera, an infra-red sensor, or an infra-red camera, the latter two being capable of measuring the two-dimensional temperature distribution, or means of specifying the position of the human body or article by means of: a radio wave source attached to the human body or article; and one or more antennas which are located in the room and detect the intensity or the direction of the radio wave. The signal processing means 2011 processes the signal obtained from the CCD camera, the infra-red sensor, or the antennas, thereby calculating the two-dimensional coordinates on the floor of the room.

In the present embodiment, the human body 2001 is identified substantially at the instance of entering the room, and the tracking of the identified human body 2001 is continued.

For example, when one or more antennas located in the room are used, (a) the direction of the human body 2001 viewed from each antenna is obtained from the direction of the radio wave received by the antenna, and (b) the distance of the human body 2001 from each antenna is obtained from the intensity of the radio wave received by the antenna. This permits the specification of the two-dimensional position of the human body 2001. In case of a plurality of antennas, the precision in such position specification is improved, and further the position of the human body 2001 can be specified on the basis of the principles of trigonometrical measurement without using the radio wave intensity.

Further, in case of an infra-red sensor or the like, data acquisition is carried out approximately in every 1 sec. In case of the data acquisition with the repetition period of this order, since the human body 2001 does not move very fast, two human bodies the movement distance of which within the repetition period are determined as an identical one. Further, the data is interpolated. In this approach, the movement path of the human body 2001 can be sufficiently analyzed and tracked. Here, with the recent improvement of the performance of the infra-red sensor or the like, a plurality of human bodies can be sufficiently discriminated when the human bodies are separated from each other by approximately 10 cm or more.

As such, identification is carried out at the instance of entering the room, and tracking is continued after that. This approach permits the identification and the position detection of each human body even when a plurality of human bodies exist in a room.

The sensor information of the personal information terminal 2006 transmitted to the base station 2007 by wireless communications 2008 is connected to the signal processing means 2011 which is connected to both the movement direction detecting means 2009 and the position detecting means 2010. Accordingly, the information is integrated. The action information of the human body integrated by the signal processing means 2011 is transferred via the network 2012 to the data storing means 2013, and stored as structured data in the data storing means 2013.

The action information of human body obtained from the signal processing means 2011 undergoes comparison and evaluation in the action evaluating means 2014 on the basis of the structured data having been accumulated in the data storing means 2013. When the action state of human body obtained from the action evaluating means 2014 is determined to be abnormal or predicted to become abnormal as a possibility in the future by the state determining means 2015, the notifying means 2016 notifies it to the person.

As such, the signal processing means 2011, together with other signal processing means (not shown) in other rooms, is connected to the network 2012. Accordingly, the information in every room can be used in common, whereby the action state of the person in every room can be understood.

When a displaying apparatus such as monitor is provided as an auxiliary apparatus to the state determining means 2015, the action state of the person in every room can be viewed at one time. This reduces substantially the load on helpers in an ordinary home as well as in an institution for the nursing care of elderlies. In the present embodiment, the kind of the network is not restricted, and the network may be a telephone network, the Internet, a dedicated in-home network, or the like.

Here, the detection signal transmitting means according to the invention corresponds to the means having the sensor signal transmitting and receiving means 2023. The signal receiving and processing means according to the invention corresponds to the means having the base station (also referred to as a master apparatus) 2007 and the signal processing means 2011. The position detecting means according to the invention corresponds to the means having the position detecting means 2010. The identifying means according to the invention corresponds to the means having the sensor signal processing means 2005. The comparing and determining means according to the invention corresponds to the means having the action evaluating means 2014 and the state determining means 2015. The state information acquisition apparatus according to the invention corresponds to the abnormal action detection apparatus according to the present embodiment. Further, the state information in the invention corresponds to the action information in the present embodiment.

Figure 14:
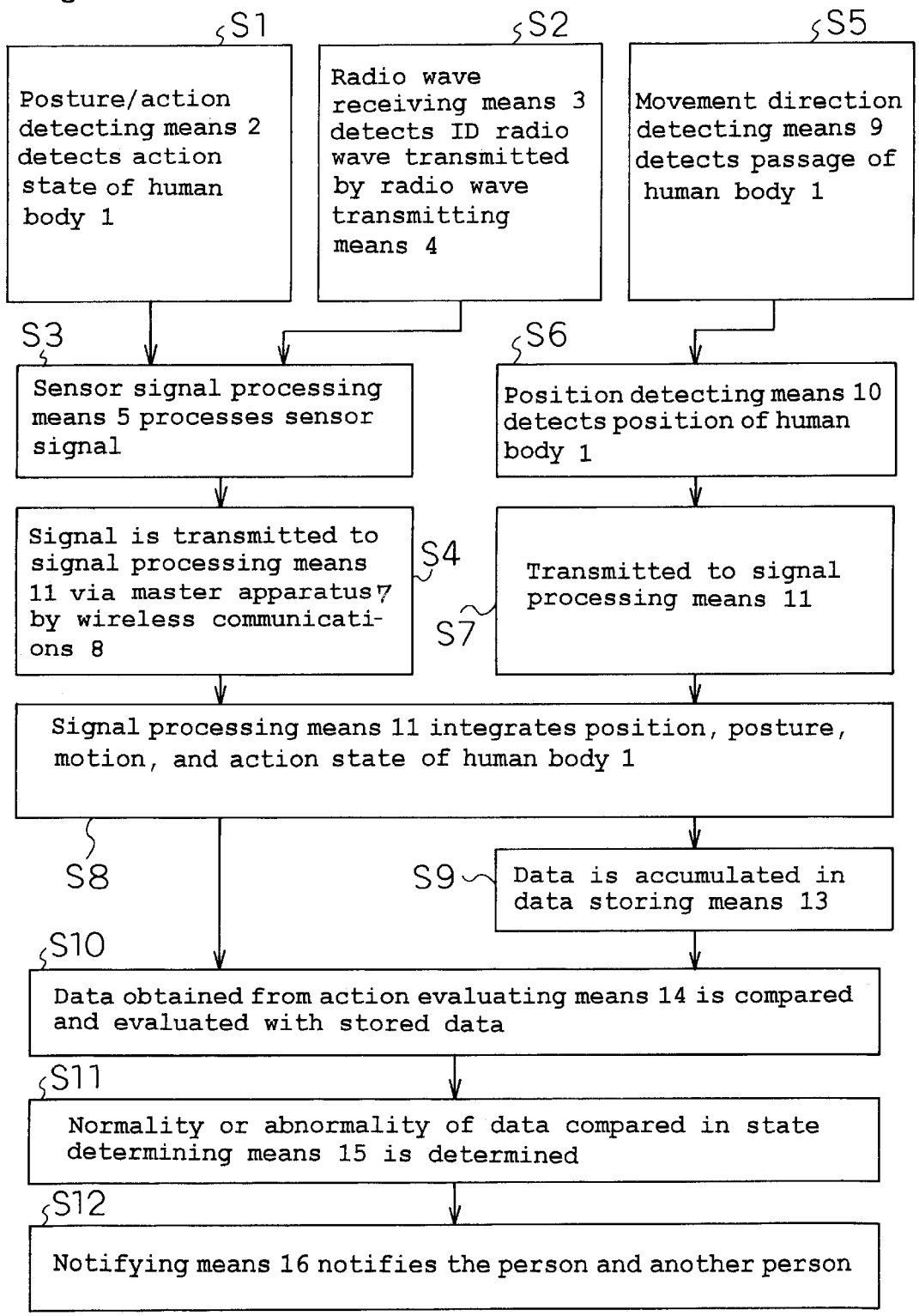
FIG. 14 is an operation diagram of an abnormal action detection system according to Embodiment 4 of the invention.

The operation of the abnormal action detection system according to the present embodiment is described below in detail with reference to FIG. 14. The figure is an illustrative diagram of the operation of the abnormal action detection system.

When the human body 2001 carries the personal information terminal 2006, the posture/action detecting means 2002 composed of an acceleration sensor or the like continuously monitors the action state of the human body 2001 (S1).

When the human body 2001 begins to enter the room, the radio wave receiving means 2003 in the personal information terminal 2006 begins to receive the ID radio wave of specific frequency from the radio wave transmitting means 2004. With the continuation of entering the room, the personal information terminal 2006 goes into the reception region of the radio wave receiving means 2003, whereby the ID radio wave is detected (S2) The sensor signal processing means 2005 processes the sensor signals detected by the posture/action detecting means 2002 (S3) These sensor signals are transmitted from the sensor signal transmitting and receiving means 2023, through the master apparatus 2007 of base station, and to the signal processing means 2011 by wireless communications 2008 (S4).

On the other hand, when the human body 2001 approaches the entrance of the room, the movement direction detecting means 2009 composed of a pyroelectric one-dimensional array device having a plurality of light receiving sections detects the passage of the human body 2001 (S5), and recognizes the start of the passage through the entrance. With the continuation of entering the room, the position detecting means 2010 according to visible-light image processing using a CCD camera detects the position of the human body 2001 (S6). The action information of the human bodies 2001 is transmitted to the signal processing means 2011 (S7).

The sensor information transmitted from the personal information terminal 2006 to the base station 2007 by wireless communications 2008 is sent to the signal processing means 2011 having the data of the movement direction detecting means 2009 and the position detecting means 2010, whereby the information is integrated by the signal processing means 2011 (S8).

The action information of the human body 2001 integrated by the signal processing means 2011 is input to the data storing means 2013 via the network 2012, and stored as structured data (S9).

The action information of the human body 2001 obtained from the sensor signal processing means 2005 undergoes comparison and evaluation in the action evaluating means 2014 on the basis of the structured data having been accumulated in the data storing means 2013 to date (S10). When the action state of the human body 2001 obtained from the action evaluating means 2014 is determined to be abnormal or predicted to become abnormal as a possibility in the future by the state determining means 2015 (S11), the notifying means 2016 notifies it to the person or another person (S12).

Embodiment 5

The configuration and the operation of an abnormal action detection system according to Embodiment 5 using a state information acquisition system according to the invention are described below with reference to FIG. 8. The figure is a schematic configuration diagram of the abnormal action detection system according to the present embodiment. Here, in addition to the configuration and the operation of the abnormal action detection system according to the present embodiment, described below is an embodiment of a state information acquisition method of the invention.

The abnormal action detection system according to the present embodiment has a configuration similar to that of the abnormal action detection system according to Embodiment 4. The difference is that the personal information terminal 2006' in the abnormal action detection apparatus according to the present embodiment comprises alarm means 2022 of generating an alarm in case of abnormality.

Similarly to the above-mentioned embodiments, when the action state of the human body obtained from the action evaluating means 2014 is determined to be abnormal or predicted to become abnormal as a possibility in the future by the state determining means 2015, the notifying means 2016 notifies it to the alarm means 2022 in the personal information terminal 2006 carried with the person by wireless.

Embodiment 6

Figure 9:
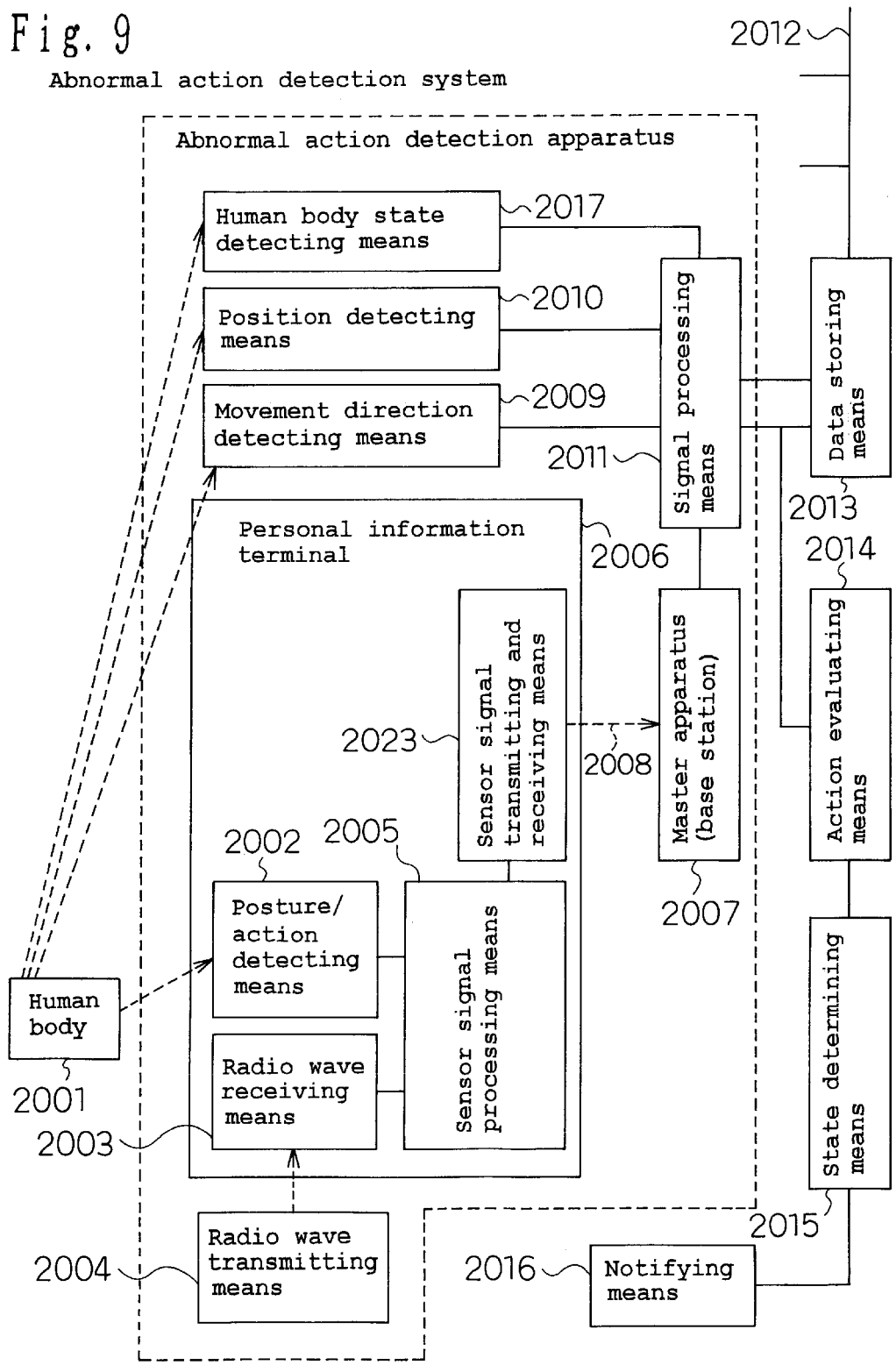
FIG. 9 is a schematic configuration diagram of an abnormal action detection system according to Embodiment 6 of the invention.

The configuration and the operation of an abnormal action detection system according to Embodiment 6 using a state information acquisition system according to the invention are described below with reference to FIG. 9. The figure is a schematic configuration diagram of the abnormal action detection system according to the present embodiment. Here, in addition to the configuration and the operation of the abnormal action detection system according to the present embodiment, described below is an embodiment of a state information acquisition method of the invention.

The abnormal action detection system according to the present embodiment has a configuration similar to that of the abnormal action detection system according to Embodiment 4. The difference is that the abnormal action detection system according to the present embodiment further comprises human body state detecting means 2017. Here, the lavatory state detecting means according to the invention corresponds to the means having the human body state detecting means 2017.

The human body state detecting means 2017 detects an abnormal state of a human body in a lavatory, and provides a sensor output corresponding to the posture of the human body by means of an infra-red sensor, a distance sensor, or the like. The sensor signal output from the human body state detecting means 2017 is processed by signal processing means 2011, and then used in the determination of entering or exiting the room by the human body as well as the determination of the posture and an abnormal state of the human body.

Figure 17:
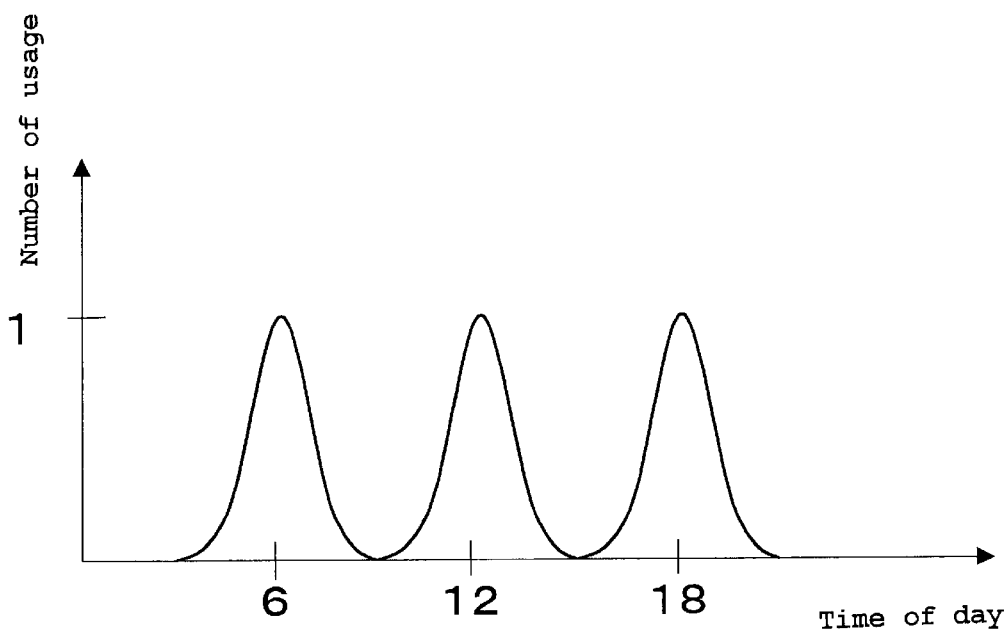
FIG. 17 is a diagram showing: the average relation between the time of day and the number of lavatory usage (FIG. 17(a)); and the average relation between the number of lavatory usage and the number of days (FIG. 17(b)); respectively, prepared from the analysis of the records in a month.
Figure 17:
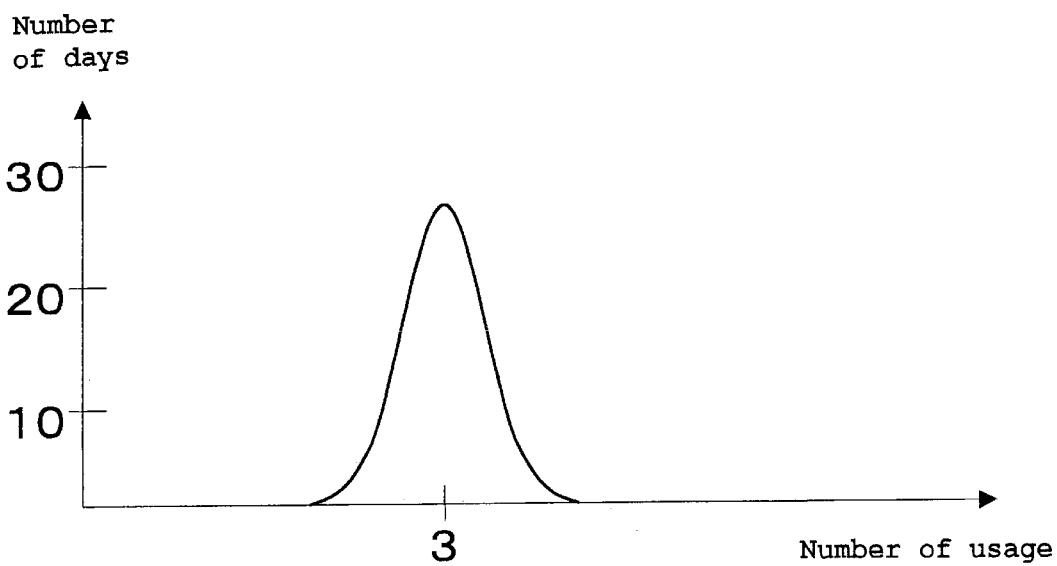

The sensor signal output from the human body state detecting means 2017 is processed by the signal processing means 2011, and then stored as a part of the above-mentioned structured data in the data storing means 2013. FIGS. 17(*a*) and 17(*b*) are diagrams showing: the average relation between the time of day and the number of lavatory usage; and the average relation between the number of lavatory usage and the number of days; respectively, prepared as structured data from the analysis of the records in a month.

The action evaluating means 2014 compares the obtained state information with the above-mentioned structured data, whereby the state determining means 2015 determines that (1) the number of lavatory usage in a day has increased, (2) the number of lavatory usage at night has increased, (3) the time interval between lavatory usage has become short, or the like. As such, the life pattern of the elderly is understood. This information can be useful in various applications of early-stage detection and treatment of diseases such as diabetes.

Embodiment 7

Figure 10:
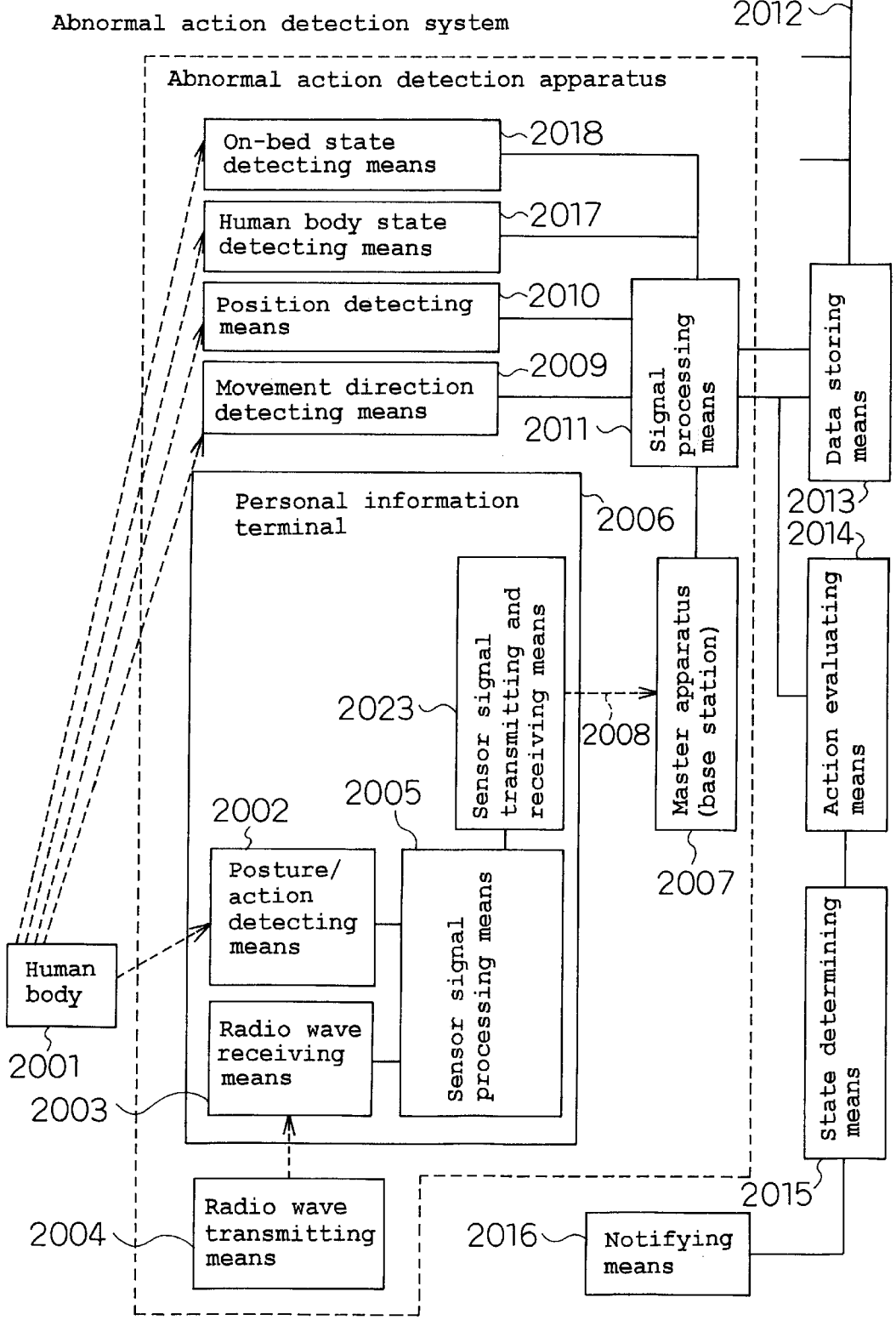
FIG. 10 is a schematic configuration diagram of an abnormal action detection system according to Embodiment 7 of the invention.

The configuration and the operation of an abnormal action detection system according to Embodiment 7 using a state information acquisition system according to the invention are described below with reference to FIG. 10. The figure is a schematic configuration diagram of the abnormal action detection system according to the present embodiment. Here, in addition to the configuration and the operation of the abnormal action detection system according to the present embodiment, described below is an embodiment of a state information acquisition method of the invention.

The abnormal action detection system according to the present embodiment has a configuration similar to that of the abnormal action detection system according to Embodiment 6. The difference is that the abnormal action detection system according to the present embodiment further comprises on-bed state detecting means 2018.

The on-bed state detecting means 2018 detects an abnormal state of a human body on a bed, and provides a sensor output corresponding to the posture of the human body by means of an infra-red sensor, a pressure sensor, or the like. The sensor signal output from the on-bed state detecting means 2018 is processed by signal processing means 2011, and then used in the determination of the presence or absence, the posture, and an abnormal state of the human body.

Figure 15:
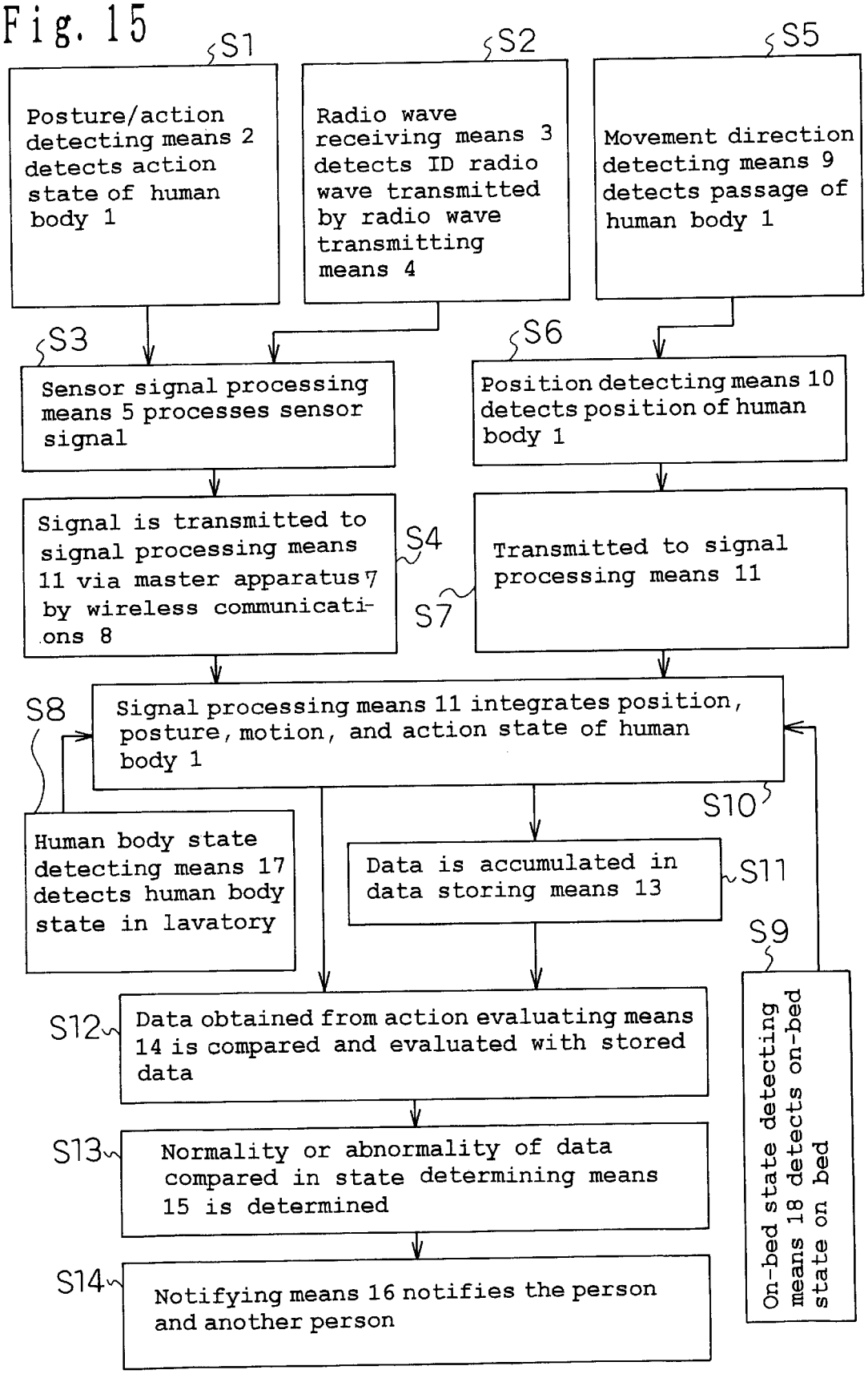
FIG. 15 is an operation diagram of an abnormal action detection system according to Embodiment 7 of the invention.

The operation of the abnormal action detection system according to the present embodiment is described below in detail with reference to FIG. 15. The figure is an illustrative diagram of the operation of the abnormal action detection system.

When the human body 2001 carries the personal information terminal 2006, the posture/action detecting means 2002 composed of an acceleration sensor or the like continuously monitors the action state of the human body 2001 (S1).

When the human body 2001 begins to enter the room, the radio wave receiving means 2003 in the personal information terminal 2006 begins to receive the radio wave of specific frequency from the radio wave transmitting means 2004. With the continuation of entering the room, the personal information terminal 2006 goes into the reception region of the radio wave receiving means 2003, whereby the ID radio wave is detected (S2). The sensor signal processing means 2005 processes the sensor signals detected by the posture/action detecting means 2002 (S3). These sensor signals are transmitted from the sensor signal transmitting and receiving means 2023, through the master apparatus 2007 of base station, and to the signal processing means 2011 by wireless communications 2008 (S4).

On the other hand, when the human body 2001 approaches the entrance of the room, the movement direction detecting means 2009 composed of a pyroelectric one-dimensional array device having a plurality of light receiving sections detects the passage of the human body 2001 (S5), and recognizes the start of the passage through the entrance. With the continuation of entering the room, the position detecting means 2010 according to visible-light image processing using a CCD camera detects the position of the human body 2001 (S6). The action information of the human bodies 2001 is transmitted to the signal processing means 2011 (S7).

Both of the human body state of the human body 2001 in the lavatory detected by the human body state detecting means 2017 and the on-bed state of the human body 2001 on the bed detected by the on-bed state detecting means 2018 are transmitted of the signal processing means 2011 (S8 and S9).

The sensor information transmitted from the personal information terminal 2006 to the base station 2007 by wireless communications 2008 is sent to the signal processing means 2011. This is carried out together with the data of the movement direction detecting means 2009, the position detecting means 2010, the human body state detecting means 2017, and the on-bed state detecting means 2018. Then, the information is integrated by the signal processing means 2011 (S10).

The action information of the human body 2001 integrated by the signal processing means 2011 is input to the data storing means 2013 via the network 2012, and stored as structured data (S11).

The action information of the human body 2001 obtained from the sensor signal processing means 2005 undergoes comparison and evaluation in the action evaluating means 2014 on the basis of the structured data having been accumulated in the data storing means 2013 to date (S12). When the action state of the human body 2001 obtained from the action evaluating means 2014 is determined to be abnormal or predicted to become abnormal as a possibility in the future by the state determining means 2015 (S13), the notifying means 2016 notifies it to the person or another person (S14).

Embodiment 8

The configuration and the operation of an abnormal action detection system according to Embodiment 8 using a state information acquisition system according to the invention are described below with reference to FIGS. 11–13. Here, in addition to the configuration and the operation of the abnormal action detection system according to the present embodiment, described below is an embodiment of a state information acquisition method of the invention.

The abnormal action detection system according to the present embodiment has a configuration similar to that of the abnormal action detection system according to Embodiment 4. Thus, described below in detail is the operation of the abnormal action detection system in the case of ID identification when a human body 2001 enters a room 2030 from a corridor. FIG. 11 is a schematic perspective view of the abnormal action detection system when the human body 2001 begins to enter the room. FIG. 12 is a schematic perspective view of the abnormal action detection system when the human body 2001 continues to enter the room. FIG. 13 is a schematic perspective view of the abnormal action detection system when the human body 2001 has entered the room.

Figure 11:
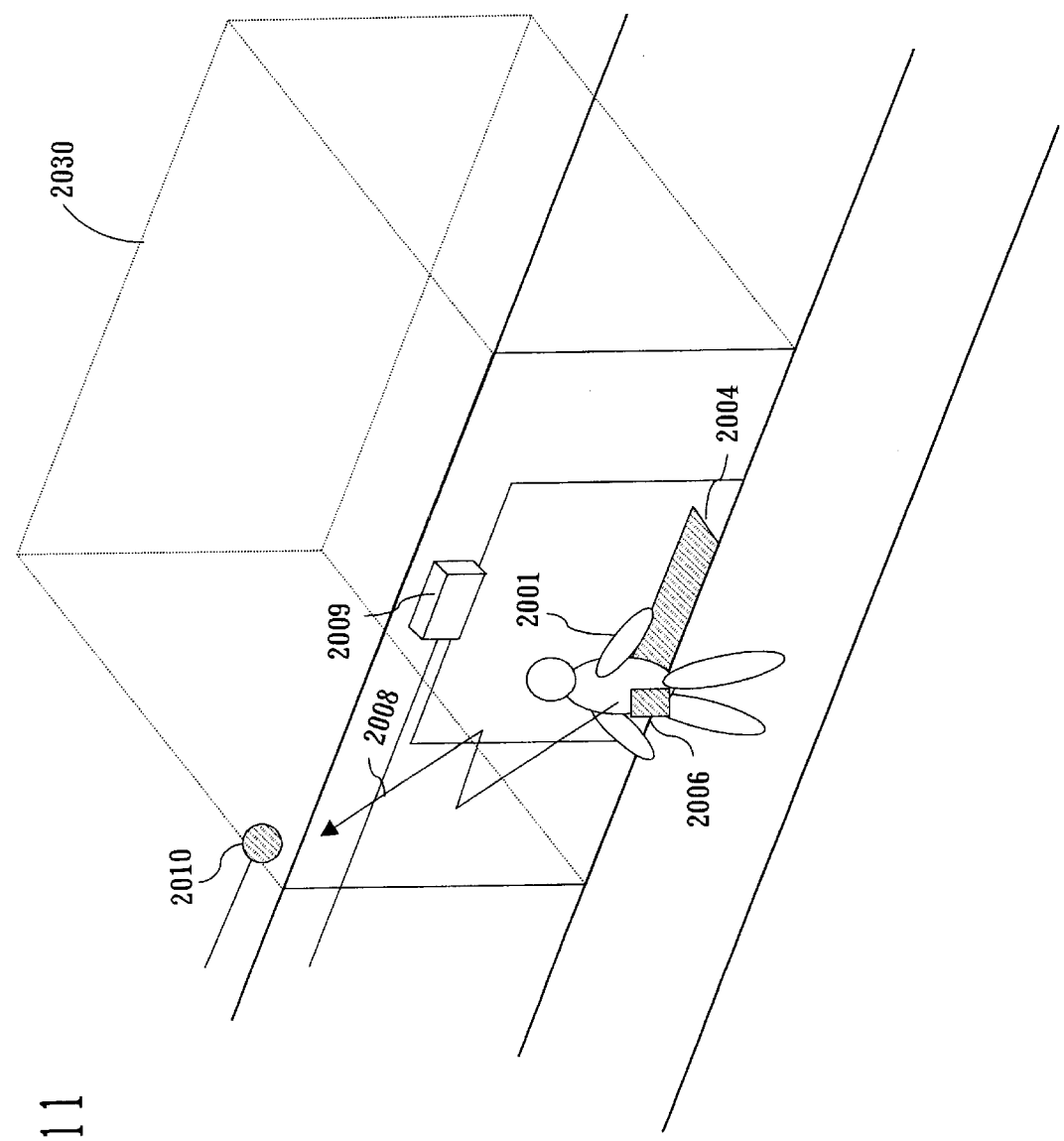
FIG. 11 is a schematic perspective view of an abnormal action detection system according to Embodiment 8 of the invention when the human body 2001 begins to enter the room.
Figure 12:
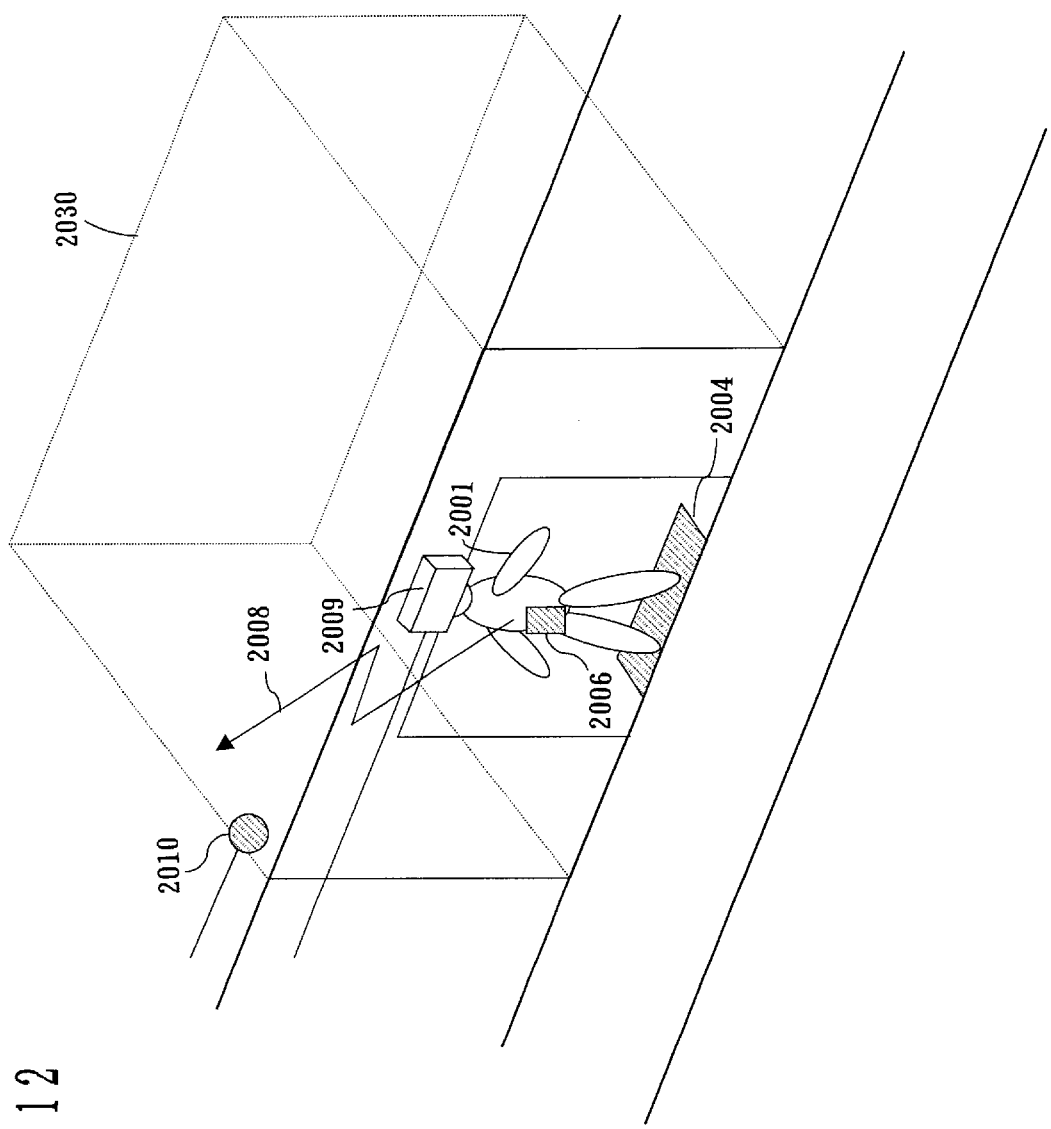
FIG. 12 is a schematic perspective view of the abnormal action detection system according to Embodiment 8 of the invention when the human body 2001 continues to enter the room.
Figure 13:
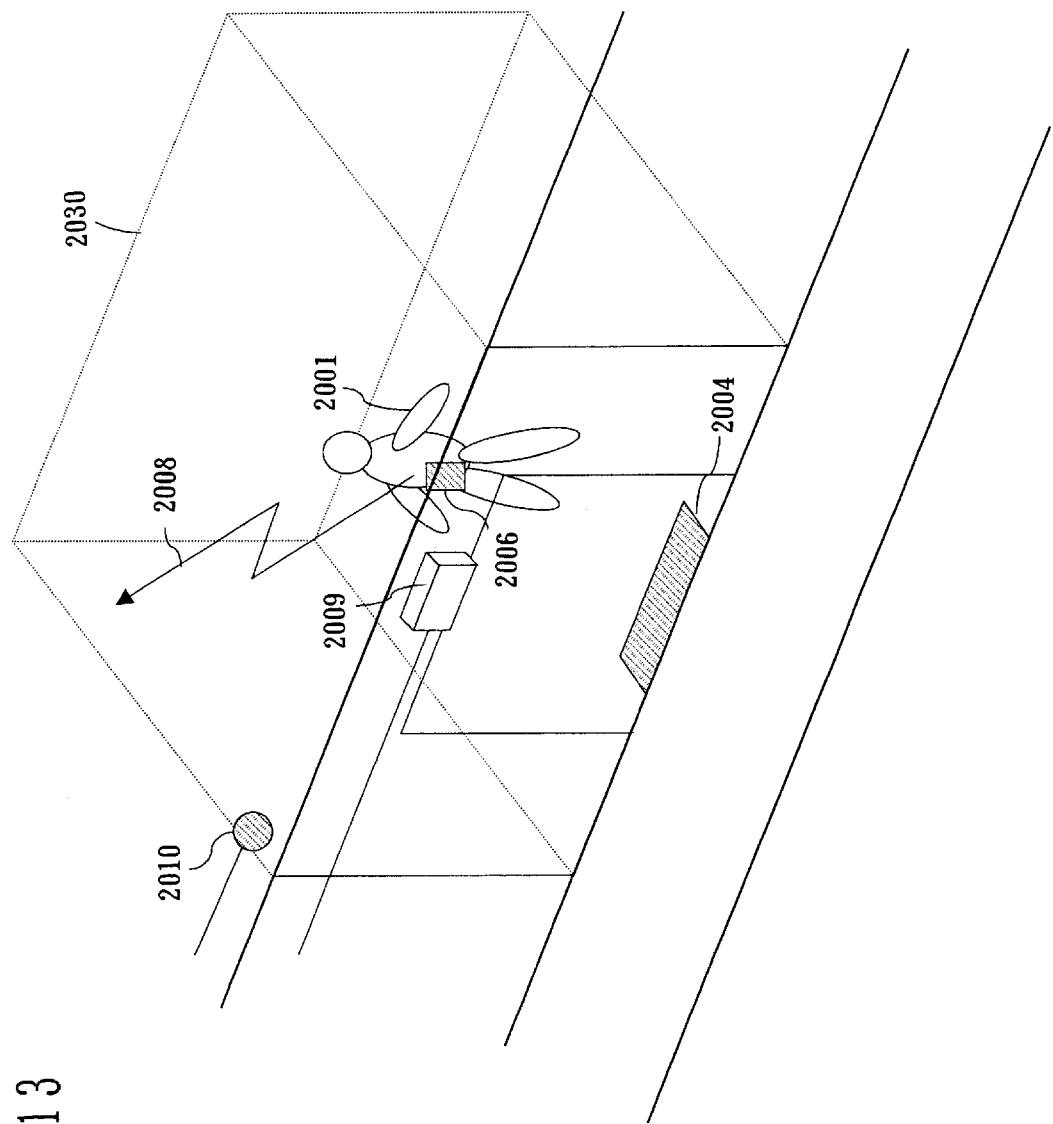
FIG. 13 is a schematic perspective view of the abnormal action detection system according to Embodiment 8 of the invention when the human body 2001 has entered the room.

As shown in FIGS. 11–13, RF-ID radio wave transmitting means 2004 and movement direction detecting means 2009 are located in the vicinity of an entrance of a room 2030. Position detecting means 2010 is located in the room 2030. The RF-ID radio wave transmitting means 2004 always transmits an ID radio wave of a frequency specific to the room 2030.

As shown in FIG. 11, when the human body 2001 carrying a personal information terminal 2006 approaches the entrance in order to enter the room 2030, the movement direction detecting means 2009 detects the human body 2001, and recognizes the start of the passage through the entrance. At that time, radio wave receiving means 2003 (see FIG. 7) in the personal information terminal 2006 begins to receive the specific frequency of the radio wave transmitting means 2004 located in the vicinity of the entrance.

As shown in FIG. 12, with the continuation of entering the room by the human body 2001, the personal information terminal 2006 goes into the reception region of the radio wave transmitted by the radio wave transmitting means 2004, whereby the radio wave receiving means 2003 (see FIG. 7) receives the ID radio wave. With reception of the ID radio wave, the sensor signal processing means 2005 transmits a radio wave specific to each terminal via the sensor signal transmitting and receiving means 2023. The signal processing means 2011 receives the radio wave via the master apparatus 2007 (see FIG. 7), thereby recognizing the personal information terminal 2006. This state is referred to as a preliminary identified state. The final identified state is the state in which the human body 2001 has continued to enter the room and the movement direction detecting means 2009 has confirmed the complete passage through the entrance, as shown in FIG. 13.

After that, until the exiting of the room 2030, the information form the sensors in the personal information terminal 2006 of the identified specific human body (also referred to as an ID) becomes ready to be received, and the information form the sensors of the identified ID is actually acquired. The position detecting means 2010 specifies the position of each identified ID such as human body 2001 in the room 2030.

The abnormal action detection system operates similarly, when the human body 2001 exits the room. That is, when the human body 2001 approaches the exit, the movement direction detecting means 2009 detects the human body 2001, and recognizes the start of the passage through the exit. At that time, radio wave receiving means 2003 (see FIG. 7) in the personal information terminal 2006 begins to receive the specific frequency of the radio wave transmitting means 2004. With the continuation of exiting the room by the human body 2001, the personal information terminal 2006 goes into the reception region of the radio wave transmitted by the radio wave transmitting means 2004, whereby the radio wave receiving means 2003 (see FIG. 7) receives the ID radio wave. This state is referred to as a preliminary identified state, similarly to the previous description. Further, the final identified state is the state in which the human body 2001 has continued to exit the room and the movement direction detecting means 2009 has confirmed the complete passage through the exit. Until the human body 2001 enters the room later, the information reception state for the sensors of the identified ID is released. Accordingly, the position detecting means 2010 does not continue the position identification because there is no identified ID.

The movement direction detecting means may be composed of: a pyroelectric one-dimensional array device having a plurality of light receiving sections; and a chopper provided in front of the array device. The field of view is divided by the timing of chopping, whereby a human body passing through can be detected. The temperature of the article of object of detection is easily measured on the basis of the reference of the chopper temperature. Accordingly, with setting an appropriate threshold in the sensor output, the time interval when a human body is present can be extracted. Further, the apparent size of the human body is determined on the basis of the distance from the sensor. Accordingly, the region of a temperature near the human body temperature and the region of the human body can be discriminated. This improves the accuracy in the human body extraction.

As such, in the movement direction detecting means using an infra-red sensor, the entering and exiting of the room is detected accurately, and the timing of reception by the RF-ID radio wave receiving means can be determined accurately. This improves the accuracy in the identification. Here, the description has been made for the case of an infra-red sensor. However, the invention is not restricted to this, and a distance sensor using light or ultrasonic wave may be used. In this case, the presence or absence of a human body is two-valued, whereby similar effect is obtained.

Further, the position detecting means may measure a visible-light image using a CCD camera, thereby extracting the human body. The CCD camera is installed in the upper part of the room so that the field of view covers the floor. Then, a visible-light image is measured. The extraction of a human body region is carried out by a technique such as the contour extraction of a moving body and the flesh color extraction of a face. Further, the apparent size of the human body is determined on the basis of the distance from the sensor. This improves the accuracy in the human body extraction. Further, the relation between the position in the field of view of the camera and the actual position on the floor can be previously measured or calculated. This gives the actual position of the extracted human body in the field of view of the camera.

Embodiment 9

Figure 16:
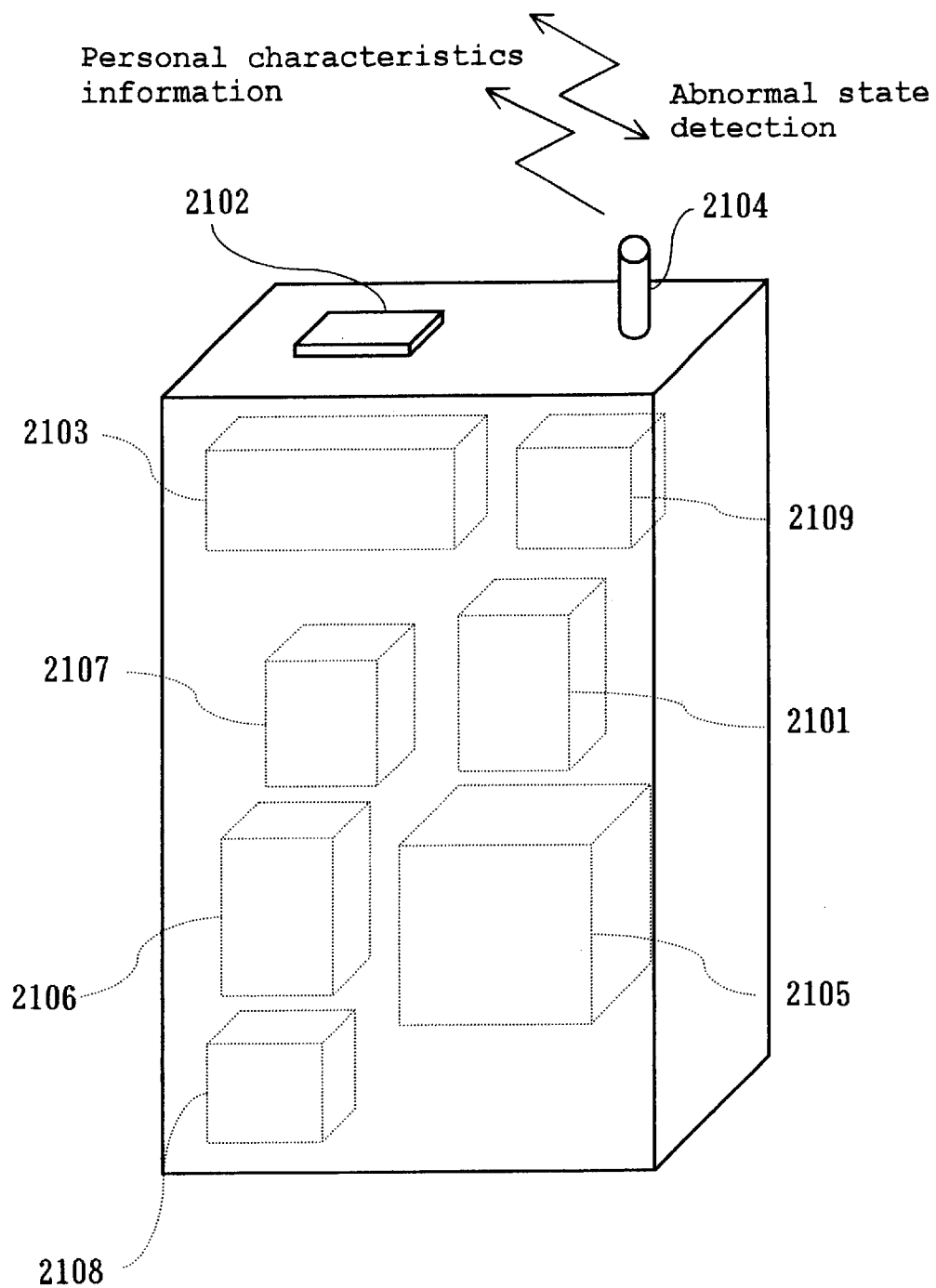
FIG. 16 is a schematic diagram of a personal information terminal according to Embodiment 9 of the invention.

The configuration and the operation of a personal information terminal according to Embodiment 9 are described below with reference to FIG. 16. The figure is a schematic configuration diagram of the personal information terminal according to the present embodiment.

The personal information terminal according to the present embodiment is attached to a part of a human body, for example, to the waist using a belt, thereby detecting the posture, the state of walking, the movement path, and the like using an acceleration sensor 2103, a gyrosensor 2101, and the like.

As for the posture, the inclination of the human body is obtained by measuring the force component of the gravity using the triaxial acceleration sensor 2103. For the state of walking, the gravity direction output from the gyrosensor 2101 is analyzed by a sensor signal processing circuit 2105, whereby it is determined that the state is static or walking, and that the state of walking is upstairs or downstairs.

Figure 8:
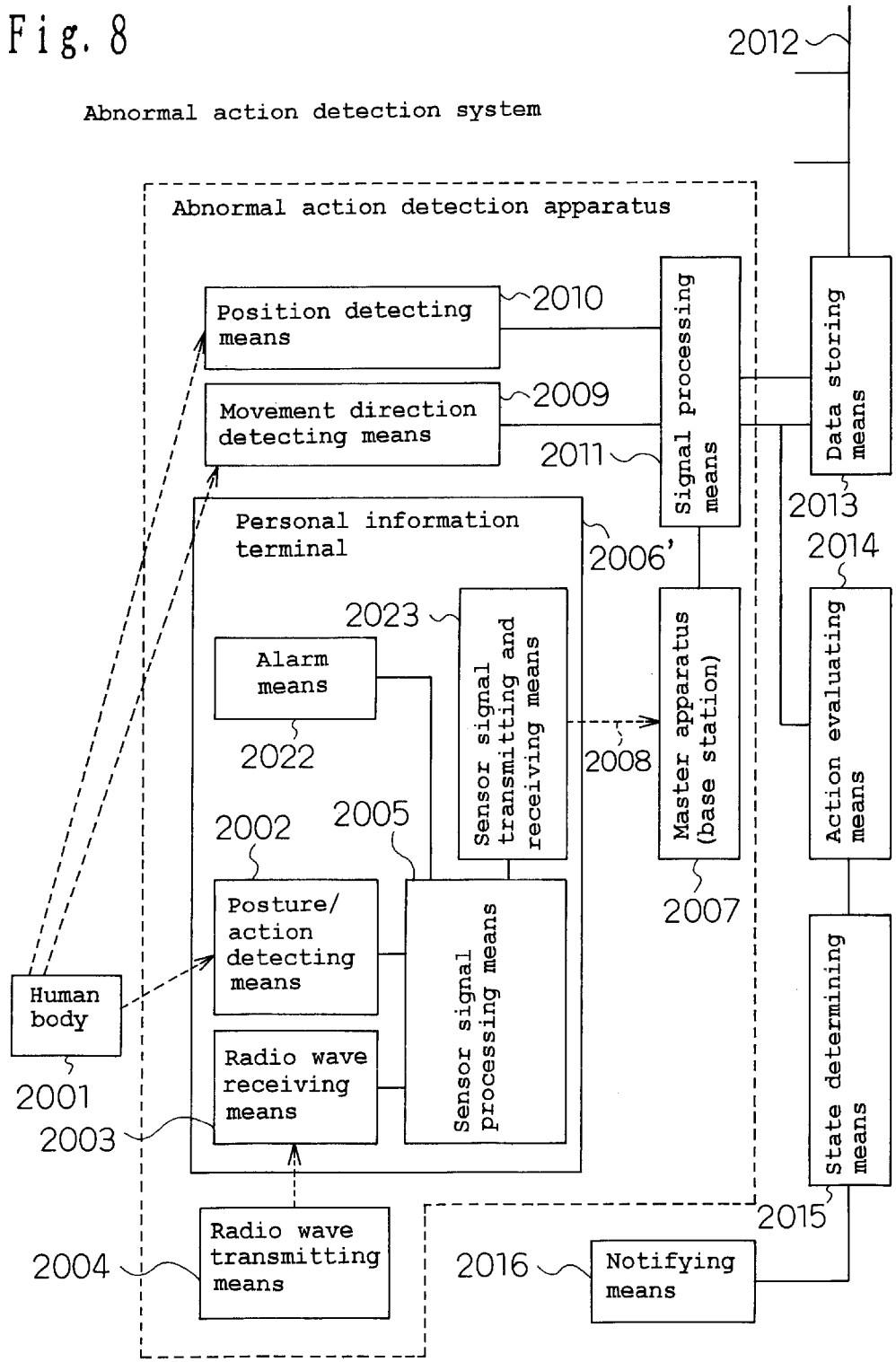
FIG. 8 is a schematic configuration diagram of an abnormal action detection system according to Embodiment 5 of the invention.

A coil 2108 receives the radio wave transmitted from the radio wave transmitting means 2004 (see FIG. 8). The signal is transformed into position information by the sensor signal processing circuit 105.

These signals are analyzed into various state information by the sensor signal processing circuit 2105. The results are transmitted as personal characteristics information through a transmitting and receiving section 2109, through an antenna 2104, and to the base station 2007 (see FIG. 8).

When there has been no human body movement for a long time, or when an abnormal state is detected, determined, or predicted, an alarm buzzer 2107 calls the person carrying this apparatus. This alarm buzzer is invoked by a signal input through the antenna 2104 and the transmitting and receiving section 2109 by wireless. When there is no response, for example, by pushing a switch 2102, to this call, an abnormal state signal is transmitted through the antenna 2104. When the abnormal state signal is transmitted, a helper checks the situation of the person, and/or the situation is notified to the outside.

All the above-mentioned means are powered by an internal battery 2106.

The present embodiment has been described for the case of an acceleration sensor and a gyrosensor. However, the invention is not restricted to this, and the posture information may be obtained by an inclination angle sensor.

As described above, the present invention provides, for example, an abnormal action detection method comprising: position detecting means which is located at least at one position in a room and detects the position of a human body by means of image processing; movement direction detecting means which is located in an entrance of said room and detects the movement direction of said human body; transmitting means which is located at least at one position in said room and transmits a radio wave of specific frequency; receiving means of receiving when the distance from said transmitting means is a predetermined value or less; posture/action detecting means of detecting the posture, action, and motion state of said human body; a wearable personal information terminal having said receiving means, said posture/action detecting means, and signal processing means of obtaining the action information of said human body; and the steps of: successively transmitting and receiving a plurality of sensor signals obtained from a plurality of human bodies carrying said wearable personal information terminals, to and from a master apparatus by wireless; integrally processing said sensor signals from said master apparatus and the signals obtained from said position detecting means and said movement direction detecting means and thereby obtaining the action information of said human body; storing the action information of said human body obtained from said signal processing means, as structured data; evaluating said action information of said human body obtained from said signal processing means by comparing it with said structured data stored in said storing means; determining and predicting an abnormality in the action state of said human body obtained from said action evaluating means, by sending means.

Further, the present invention provides, for example, an abnormal action detection apparatus comprising: position detecting means which is located at least at one position in a room and detects the position of a human body by means of image processing; movement direction detecting means which is located in an entrance of said room and detects the movement direction of said human body; transmitting means which is located at least at one position in said room and transmits a radio wave of specific frequency; receiving means of receiving when the distance from said transmitting means is a predetermined value or less; posture/action detecting means of detecting the posture, action, and motion state of said human body; a wearable personal information terminal having said receiving means, said posture/action detecting means, and signal processing means of obtaining the action information of said human body; a master apparatus for successively transmitting and receiving the sensor signals from a plurality of said wearable personal information terminals by wireless; signal processing means of integrally processing said sensor signals from said master apparatus and the signals obtained from said position detecting means and said movement direction detecting means and thereby obtaining the action information of said human body; storing means of storing the action information of said human body obtained from said signal processing means, as structured data; action evaluating means of evaluating said action information of said human body obtained from said signal processing means by comparing it with said structured data stored in said storing means; state determining means of determining and predicting an abnormality in the action state of said human body obtained from said action evaluating means; and notifying means of notifying said determined abnormality in said action state of said human body to the person or another person.

Furthermore, the present invention provides, for example, an abnormal action detection system comprising: position detecting means which is located at least at one position in a room and detects the position of a human body by means of image processing; movement direction detecting means which is located in an entrance of said room and detects the movement direction of said human body; transmitting means which is located at least at one position in said room and transmits a radio wave of specific frequency; receiving means of receiving when the distance from said transmitting means is a predetermined value or less; posture/action detecting means of detecting the posture, action, and motion state of said human body; a wearable personal information terminal having said receiving means, said posture/action detecting means, and signal processing means of obtaining the action information of said human body; a master apparatus for successively transmitting and receiving the sensor signals from a plurality of said wearable personal information terminals by wireless; signal processing means of integrally processing said sensor signals from said master apparatus and the signals obtained from said position detecting means and said movement direction detecting means and thereby obtaining the action information of said human body; storing means of storing the action information of said human body obtained from said signal processing means, in an integrated form of structured data by means of a network; action evaluating means of evaluating said action information of said human body obtained from said signal processing means by comparing it with said structured data stored in said storing means connected to said network; state determining means of determining and predicting an abnormality in the action state of said human body obtained from said action evaluating means; and notifying means of notifying said determined abnormality in said action state of said human body to said personal information terminal and other terminals connected to said network.

Further, the present invention may be an abnormal action detection system further comprising: human body state detecting means of detecting an abnormal state of a human body in a lavatory; and signal processing means of integrally processing said sensor signals from said master apparatus and the signals obtained from said position detecting means, said movement direction detecting means, and said human body state detecting means and thereby obtaining the action information of said human body.

Further, the present invention may be an abnormal action detection system further comprising: on-bed state detecting means of detecting the on-bed state of a human body on a bed; and signal processing means of integrally processing said sensor signals from said master apparatus and the signals obtained from said position detecting means, said movement direction detecting means, and said on-bed state detecting means and thereby obtaining the action information of said human body.

According to the abnormal action detection apparatus of the invention having the above-mentioned configuration, a human body entering a room can be identified. Further, the action and the action information of the human body, such as in-room position, posture, and action information, can be measured accurately. Further, state determining means attached to the human body communicates with the base station by wireless, and the base station is connected to the network. This permits integrated management of the personal characteristics information of human bodies in a plurality of rooms or specified areas. Accordingly, the action of the human bodies in the whole building can be understood in real time. This permits various applications such as abnormality detection, air conditioning/illumination control, and security.

In the present embodiment, the detection of position and the detection of posture and/or action state according to the invention have been applied to the human body 2001 (that is, a person). However, the invention is not restricted to this, and may be applied to an animal.

Further, in the present embodiment, the posture/action detecting means according to the invention has been built in the personal information terminal 2006. However, the invention is not restricted to this, and the posture/action detecting means according to the invention may be provided separately from the personal information terminal 2006.

Further, in the present embodiment, the transmission of the detection signals based on the detection of the posture and/or action state has been carried out on the basis of the fact that the radio wave transmitted by the radio wave transmitting means 2004 is received by the radio wave receiving means 2003 when the distance from the radio wave transmitting means 2004 is a predetermined value or less. However, the invention is not restricted to this, and the transmission of these detection signals maybe carried out always, or alternatively, periodically on the basis of predetermined rules. However, obviously, in case that the transmission and reception of the detection signals is carried out when the distance from the radio wave transmitting means 2004 is a predetermined value or less, as in the present embodiment, the state information of the human body 2001 during the stay in the room is acquired efficiently.

Further, in the present embodiment, the predetermined region in the invention has been a room in which the base station (also referred to as a master apparatus) 2007, the signal processing means 2011, and the like have been located. However, the invention is not restricted to this, and the predetermined region in the invention may be a region in a garden or an elevator. In this case, obviously, when the radio wave transmitting means 2004, the base station (also referred to as a master apparatus) 2007, the signal processing means 2011, and the like are located in each region, the state information is acquired more efficiently.

Further, in the present embodiment, the state information acquisition system according to the invention has comprised: data storing means 2013 of storing the structured data; action evaluating means 2014 of evaluating the obtained action information by comparing it with the structured data; state determining means 2015 of determining the normality or abnormality in the person on the basis of the result of the evaluation; and notifying means 2016 of notifying the abnormality, when so determined. However, the invention is not restricted to this, and the state information acquisition system according to the invention may be configured without these means. In this case, for example, the acquired state information may be displayed always on a monitor, and the notification of the abnormality may be processed by manual operation by a person watching the monitor.

Further, in the present embodiment, the storing means according to the invention has stored the structured data generated by accumulating the action information of the human body 2001. However, the invention is not restricted to this, and the storing means according to the invention may store the state information obtained from the result of processing and/or standard information having been prepared previously. Further, the storing means according to the invention may store more detailed structured data corresponding to each human body generated by correcting the previously input information of a standard human body with the state information continuously accumulated for each human body of object of detection. In this case, (1) when the accumulation of the state information is not yet sufficient, the data mainly based on the previously input information is used, while (2) when the accumulation of the state information is sufficient, the above-mentioned detailed and corrected structured data is used. Then, the state information is compared with the predetermined reference. This approach permits more appropriate determination of the normality or abnormality in the person or animal of object of detection.

Further, in the present embodiment, the state information acquisition system according to the invention has comprised three means of identifying means, position detecting means, and posture/action detecting means. However, the invention is not restricted to this, and the state information acquisition system according to the invention may comprise only any two of these three.

Further, in the present embodiment, the processing of detected signals according to the invention has been carried out by: the sensor signal processing means 2005 on the transmission side (that is, on the side of the terminal); and the signal processing means 2011 on the reception side (that is, on the side opposite to the terminal). However, the invention is not restricted to this, and the processing of detected signals according to the invention may be carried out, for example, (1) substantially only on the reception side, (2) substantially only on the transmission side when no position detection is carried out on the side opposite to the terminal, or (3) substantially by a dedicated information processing apparatus provided on the side of the data storing means according to the invention. In this case, the timing of the processing affects slightly the timing of obtaining the state information according to the present invention.

Further, in the present embodiment, the state information acquisition system according to the invention has comprised human body state detecting means 2017 and on-bed state detecting means 2018. However, the invention is not restricted to this, and the state information acquisition system according to the invention may comprise on-bed state detecting means alone.

Further, in the present embodiment, the state information acquisition system according to the invention has comprised movement direction detecting means 2009. However, the invention is not restricted to this, and the state information acquisition system according to the invention may be configured without movement direction detecting means.

Further, in the present embodiment, the identification of the person or animal according to the invention has been carried out by: the sensor signal transmitting and receiving means 2023 transmitting a radio wave of a frequency specific to the personal information terminal 2006 carried with the human body 2001; and the signal processing means 2011 receiving the radio wave and thereby recognizing the personal information terminal 2006. However, the invention is not restricted to this, and the identification of the person or animal according to the invention may be carried out by extracting characteristic quantities such as the face from a CCD image shot by a CCD camera.

Further, in the present embodiment, the identification of the person or animal according to the invention has been applied to a single human body 2001. Further, in the present embodiment, even in case of a plurality of persons or animals, the identification of the person or animal according to the invention (1) can be applied to the plurality of persons or animals by performing the above-mentioned identification process to each person or animal, or (2) is unnecessary when each attachable terminal apparatus according to the invention is carried with a single person or animal.

Furthermore, the present invention provides an abnormal action detection apparatus comprising: position detecting means; movement direction detecting means; transmitting means of transmitting a radio wave of specific frequency; receiving means; posture/action detecting means; a wearable personal information terminal having said receiving means, said posture/action detecting means, and sensor signal processing means of obtaining the action information of the human body; a master apparatus for successively transmitting and receiving the sensor signals from a plurality of said wearable personal information terminals by wireless; signal processing means of integrally processing said sensor signals from said master apparatus and the signals obtained from said position detecting means and said movement direction detecting means and thereby obtaining the action information of said human body; storing means of storing the action information of said human body obtained from said signal processing means, as structured data; action evaluating means of evaluating said action information of said human body obtained from said signal processing means by comparing it with said structured data stored in said storing means; state determining means of determining and predicting an abnormality in the action state of said human body obtained from said action evaluating means; and notifying means of notifying said determined abnormality in said action state of said human body to the person or another person. According to this configuration, a human body entering a room can be identified. Further, the action of the human body, such as in-room position, posture, and action information, can be measured accurately. The personal characteristics information is accumulated, and the stored data is used for the comparison and evaluation of the action information of the human body. As such, an abnormality in the action is determined, and the abnormality is notified to the person or another person. Further, state determining means attached to the human body communicates with the base station by wireless, and the base station is connected to the network. This permits integrated management of the action information of human bodies in a plurality of rooms or specified areas. Accordingly, the action of the human bodies in the whole building can be understood in real time. This permits various applications such as abnormality detection, air conditioning/illumination control, and security.

As such, the human body is identified, and the position of the human body is specified. Further, the posture, action, and motion state of the human body are specified. Furthermore, the action information of a plurality of human bodies can be integrated and stored as a data base. Then, daily action state is compared and evaluated with the normal action state, whereby an abnormality in the action is determined and notified. Accordingly, an abnormal action detection method according to the invention, and an apparatus and a system using the same permit easy, accurate, reliable, and inexpensive abnormal action detection and prediction, thereby substantially contributing to the expansion of home information infrastructure business.

Embodiment 10

Figure 18:
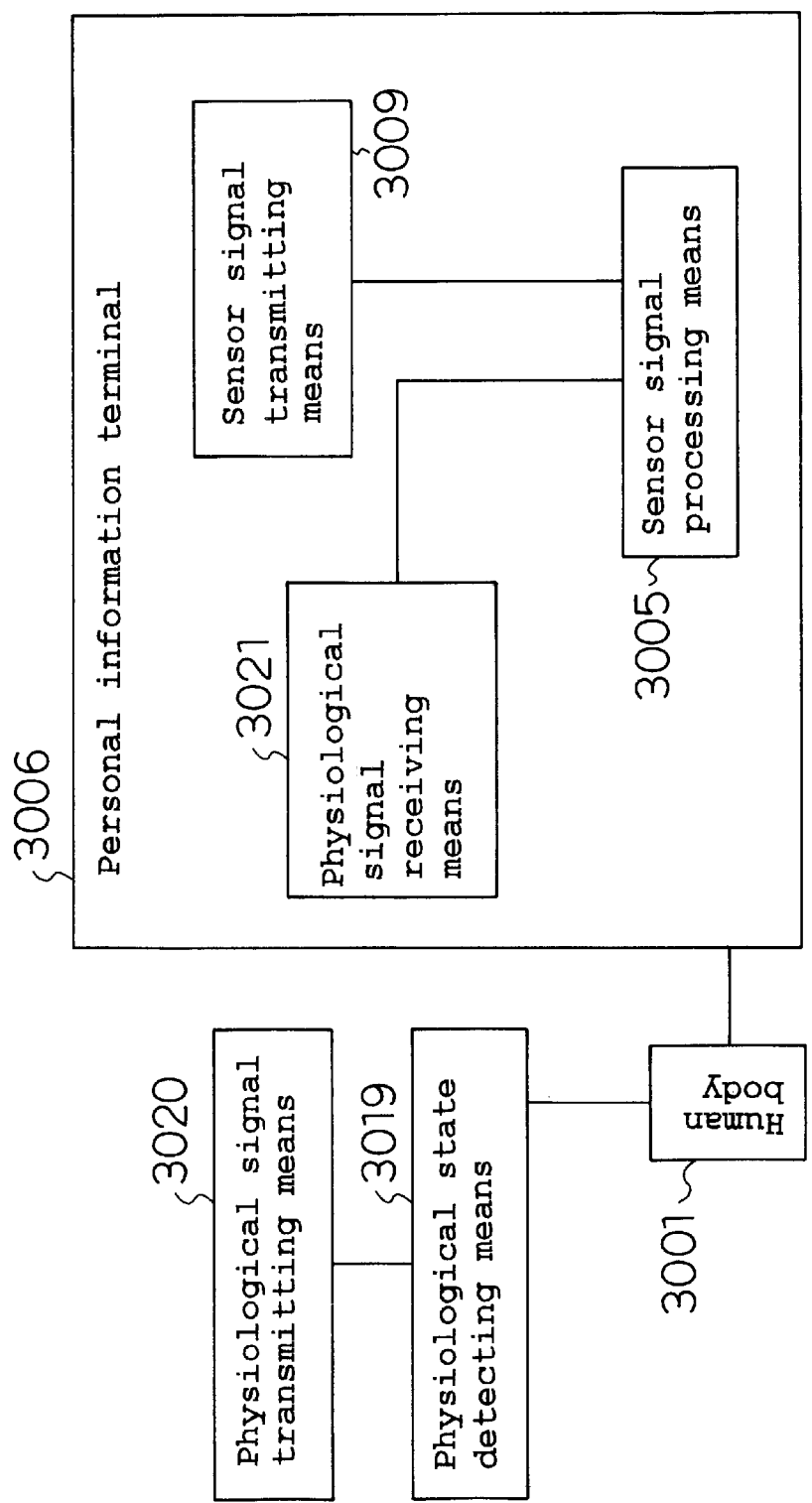
FIG. 18 is a schematic configuration diagram of a state information detection and transmission apparatus according to Embodiment 10 of the invention.

A state information detection and transmission apparatus according to Embodiment 10 is described below with reference to the drawings. FIG. 18 is a schematic configuration diagram of the state information detection and transmission apparatus according to Embodiment 10 of the invention. Described below is the configuration in the present embodiment. The present embodiment comprises a group of sensors composed of a personal information terminal 3006 and physiological state detecting means 3019.

The personal information terminal 3006 is attached to a human body 3001 and comprises: physiological signal receiving means 3021 of receiving a sensor signal transmitted from physiological signal transmitting means 3020 attached to the physiological state detecting means 3019 attached to the human body 3001; sensor signal processing means 3005 of processing the received sensor signal; and sensor signal transmitting means 3009 of transmitting the processed sensor signals to a base station by wireless.

The physiological state detecting means 3019 detects the physiological information such as pulse and heartbeat of the human body. The analogue signal obtained from the physiological state detecting means 3019 is transmitted from the physiological signal transmitting means 3020. The analogue signal transmitted from the physiological signal transmitting means 3020 is received by the physiological signal receiving means 3021 in every 1 sec. The received analogue signal is converted into a digital signal by signal processing by the sensor signal processing means 3005. The digital signal obtained from the sensor signal processing means 3005 is transmitted to the base station by the sensor signal transmitting means 3009.

Figure 19:
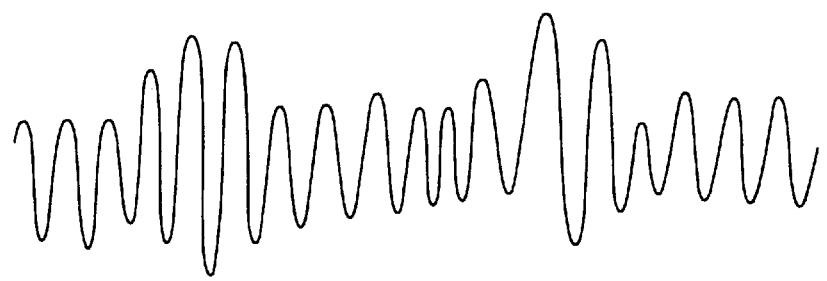
FIG. 19 is a schematic diagram of a sensor signal in a personal characteristics information acquisition method according to Embodiment 10 of the invention.
Figure 19:
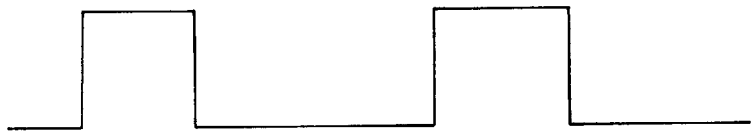

FIG. 19 is a schematic diagram of a sensor signal in the personal characteristics information acquisition method of the state information detection and transmission apparatus according to Embodiment 10 of the invention. FIG. 19(*a*) shows an analogue signal before signal processing, while FIG. 19(*b*) shows a digital signal after signal processing. As such, the physiological signal is received in every predetermined time interval, whereby the physiological signal having a high noise level and a large amount of data can be converted into a digital signal efficiently.

In the present embodiment, the analogue signal transmitted from the physiological signal transmitting means 3020 has been received by the physiological signal receiving means 3021 in every 1 sec. However, the physiological signal transmitting means 3020 may transmit the physiological information to the personal information terminal 3006 in every predetermined time interval. Alternatively, the physiological signal receiving means 3021 may receive the physiological information in every predetermined time interval. Further, the sensor signal transmitting means 3009 may transmit the physiological information to the base station in every predetermined time interval. In each case, the amount of data transmitted by the physiological signal transmitting means 3020 and the amount of data transmitted by the sensor signal transmitting means 3009 are reduced.

The state information detection and transmission apparatus according to the present embodiment may comprise first uncarry detecting means of detecting that the physiological state detecting means 3019 becomes uncarried with the human body 3001. In this case, when the first uncarry detecting means detects that the physiological state detecting means 3019 becomes uncarried with the human body, the physiological signal transmitting means 3020 may transmit uncarry information indicating the situation to the personal information terminal 3006. This permits easy understanding of the reason in the case that there is no change in the data transmitted from the sensor signal transmitting means 3009 to the base station.

The state information detection and transmission apparatus according to the present embodiment may comprise second uncarry detecting means of detecting that the personal information terminal 3006 having the physiological signal receiving means 3021 becomes uncarried with the human body 3001. In this case, when the second uncarry detecting means detects that the personal information terminal 3006 becomes uncarried with the human body 3001, the sensor signal transmitting means 3009 may transmit uncarry information indicating the situation to the base station. In this case, it is easily understood that the personal information terminal 3006 becomes uncarried with the human body 3001, from the uncarry information received by the base station.

In the present embodiment, the physiological information has been considered. Having been described are: the case of reducing the amount of data of the physiological information transmitted from the physiological signal transmitting means 3020 to the physiological signal receiving means 3021; and the case of reducing the amount of data of the physiological information transmitted from the sensor signal transmitting means 3009 to the base station. Similarly, it is possible to reduce the amount of data of the state information on all or part of the posture, action, and motion state of the human body, transmitted from the sensor signal transmitting means 3009 to the base station.

That is, when the state detecting means of detecting the state information on all or part of the posture, action, and motion state of the human body is built in the personal information terminal 3006, the sensor signal transmitting means 3009 transmits the state information on all or part of the posture, action, and motion state, to the base station in every predetermined time interval. This reduces the amount of data transmitted from the sensor signal transmitting means 3009, similarly to the case of the physiological information.

Embodiment 11

Figure 20:
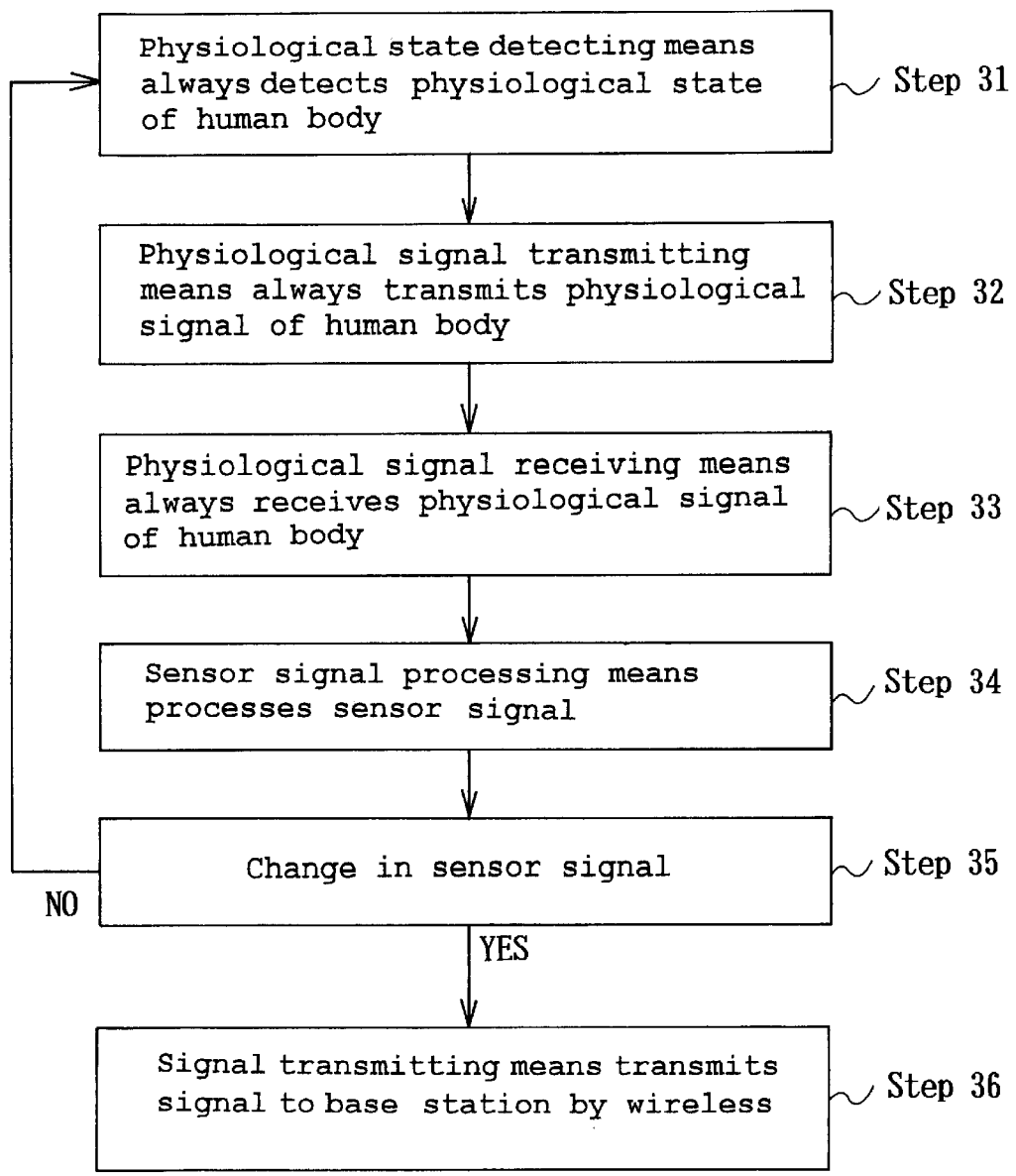
FIG. 20 is an operation diagram of a state information detection and transmission apparatus according to Embodiment 11 of the invention.

A state information detection and transmission apparatus according to Embodiment 11 is described below with reference to the drawings. FIG. 20 is a schematic operation diagram of the state information detection and transmission apparatus according to Embodiment 11 of the invention. Described below is the operation in the present embodiment. The state information detection and transmission apparatus according to the present embodiment has the same configuration as that of the state information detection and transmission apparatus according to Embodiment 10 shown in FIG. 18.

The physiological state detecting means always detects the physiological state such as pulse and heartbeat of a human body (step 31). The analogue signal obtained from the physiological state detecting means is always transmitted from the physiological signal transmitting means (step 32). The analogue signal transmitted from the physiological signal transmitting means is always received by the physiological signal receiving means (step 33). The received analogue signal is converted into a digital signal by signal processing by the sensor signal processing means (step 34). Only when a change occurs in the digital signal obtained from the sensor signal processing means (step 35),the signal-processed physiological information is transmitted to the base station by the sensor signal transmitting means by wireless (step 36). When there is no change (step 35), no sensor signal is transmitted.

As such, only when a change occurs in the digital signal obtained by the signal processing by the sensor signal processing means, the digital signal is transmitted to the base station by wireless. By virtue of this, the physiological signal having a high noise level and a large amount of data can be efficiently transmitted to the base station.

In the present embodiment, the digital signal has been transmitted to the base station, only when a change occurs in the digital signal obtained by the signal processing by the sensor signal processing means. However, the physiological signal transmitting means may transmit the physiological information to the personal information terminal 3006, only when a substantial change occurs in the signal detected by the physiological state detecting means. This reduces similarly the amount of data transmitted by the physiological signal transmitting means and the amount of data transmitted by the sensor signal transmitting means.

"A change in the signal" in the present embodiment indicates a change exceeding, for example, 10% of the value of the physiological information such as pulse averaged over the past 1 minute. These specific examples of "1 minute" and "10%" are used only for the purpose of simplicity of description. The time interval for the average may be a value other than 1 minute, and the amount of change may be a value other than the value exceeding 10%.

The state information detection and transmission apparatus according to the present embodiment may comprise first uncarry detecting means of detecting that the physiological state detecting means becomes uncarried with the human body. In this case, when the first uncarry detecting means detects that the physiological state detecting means becomes uncarried with the human body, the physiological signal transmitting means may transmit uncarry information indicating the situation to the personal information terminal. This permits easy understanding of the reason in the case that a change occurs in the signal obtained by the physiological state detecting means.

The state information detection and transmission apparatus according to the present embodiment may comprise second uncarry detecting means of detecting that the personal information terminal having the physiological signal receiving means becomes uncarried with the human body. In this case, when the second uncarry detecting means detects that the personal information terminal becomes uncarried with the human body, the sensor signal transmitting means may transmit uncarry information indicating the situation to the base station. In this case, it is easily understood that the personal information terminal becomes uncarried with the human body, from the uncarry information received by the base station.

In the present embodiment, the physiological information has been considered. Having been described are: the case of reducing the amount of data of the physiological information transmitted from the physiological signal transmitting means 3020 to the physiological signal receiving means 3021; and the case of reducing the amount of data of the physiological information transmitted from the sensor signal transmitting means 3009 to the base station. Similarly, it is possible to reduce the amount of data of the state information on all or part of the posture, action, and motion state of the human body, transmitted from the sensor signal transmitting means 3009 to the base station.

That is, when the state detecting means of detecting the state information on all or part of the posture, action, and motion state of the human body is built in the personal information terminal 3006, the sensor signal transmitting means 3009 transmits all or part of the state information to the base station only when a substantial change occurs in at least a part of the state information on all or part of the posture, action, and motion state. This reduces the amount of data transmitted from the sensor signal transmitting means 3009, similarly to the case of the physiological information.

Further, the state information detection and transmission apparatus according to the present embodiment may comprise uncarry detecting means of detecting that the personal information terminal having the state detecting means becomes uncarried with the human body. In this case, when the second uncarry detecting means detects that the personal information terminal becomes uncarried with the human body, the sensor signal transmitting means 3009 may transmit uncarry information indicating the situation to the base station. In this case, it is easily understood that the personal information terminal becomes uncarried with the human body, from the uncarry information received by the base station.

Embodiment 12

Figure 21:
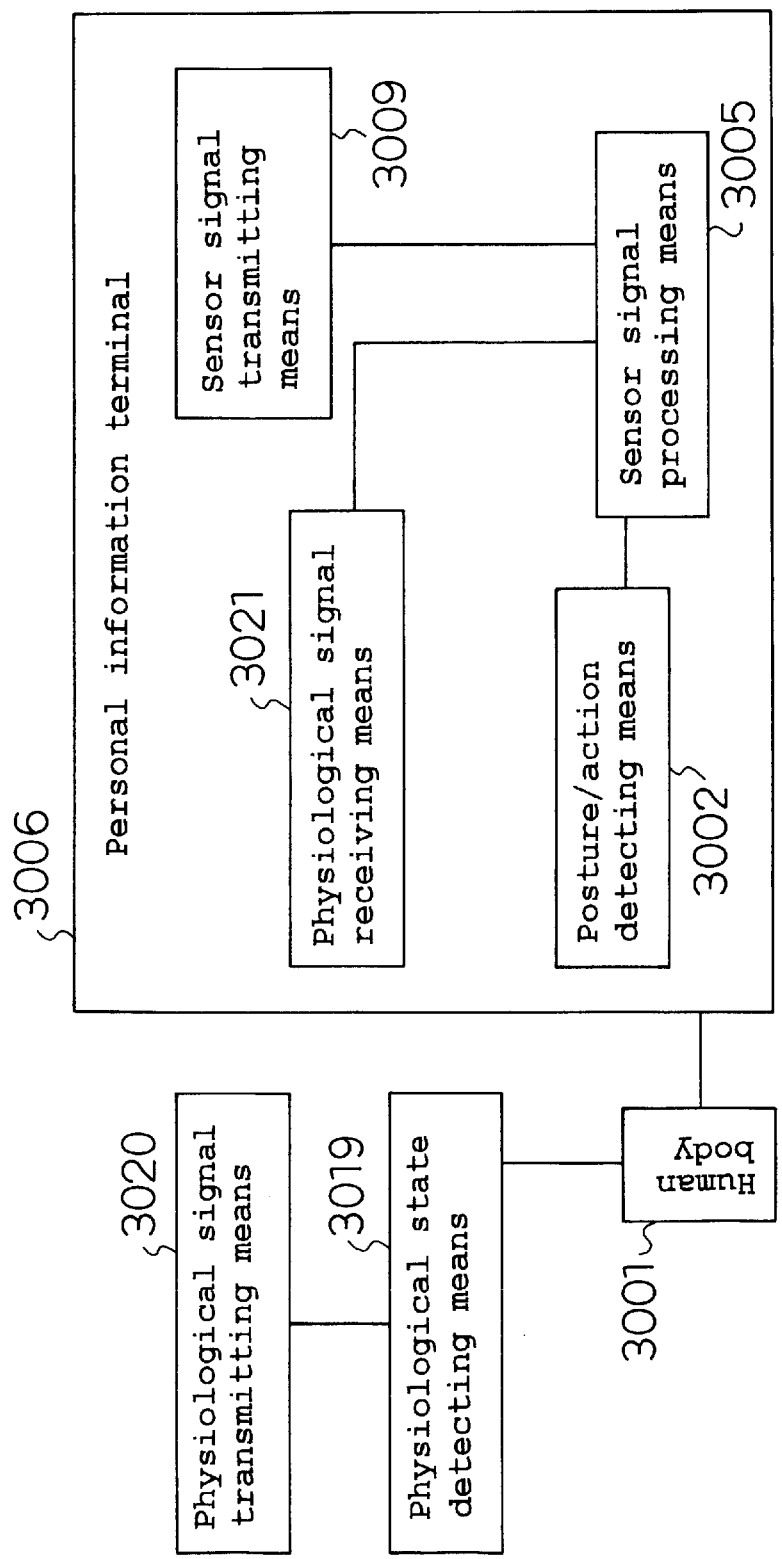
FIG. 21 is a schematic configuration diagram of a state information detection and transmission apparatus according to Embodiment 12 of the invention.

A state information detection and transmission apparatus according to Embodiment 12 is described below with reference to the drawings. FIG. 21 is a schematic configuration diagram of the state information detection and transmission apparatus according to Embodiment 12 of the invention. Described below is the configuration in the present embodiment. The present embodiment comprises a group of sensors composed of a personal information terminal 3006 and physiological state detecting means 3019.

The personal information terminal 3006 is attached to a human body 3001 and comprises: posture/action detecting means 3002 of detecting the posture, body motion, action, and action state of the human body by means of an acceleration sensor, a gyrosensor, or the like; physiological signal receiving means 3021 of receiving a sensor signal transmitted from the physiological signal transmitting means 3020 attached to the physiological state detecting means 3019 attached to the human body 3001; sensor signal processing means 3005 of processing the sensor signals obtained from these sensors; and sensor signal transmitting means 3009 of transmitting these sensor signals to the base station by wireless.

The physiological state detecting means 3019 detects the physiological information such as pulse and heartbeat of the human body. The analogue signal obtained from the physiological state detecting means 3019 is transmitted from the physiological signal transmitting means 3020. The analogue signal transmitted from the physiological signal transmitting means 3020 is received by the physiological signal receiving means 3021. The received analogue signal is converted into a digital signal by signal processing by the sensor signal processing means 3005.

On the other hand, the signal obtained from the posture/action detecting means 3002 composed of an acceleration sensor, a gyrosensor, or the like undergoes signal processing by the sensor signal processing means 3005, whereby the posture, body motion, action, and motion state of the human body 3001 are detected. Only when a change occurs in at least one of the digital signals obtained from the sensor signal processing means 3005, the information signal-processed by the sensor signal processing means 3005 is transmitted to the base station by sensor signal transmitting means 3009.

Figure 22:
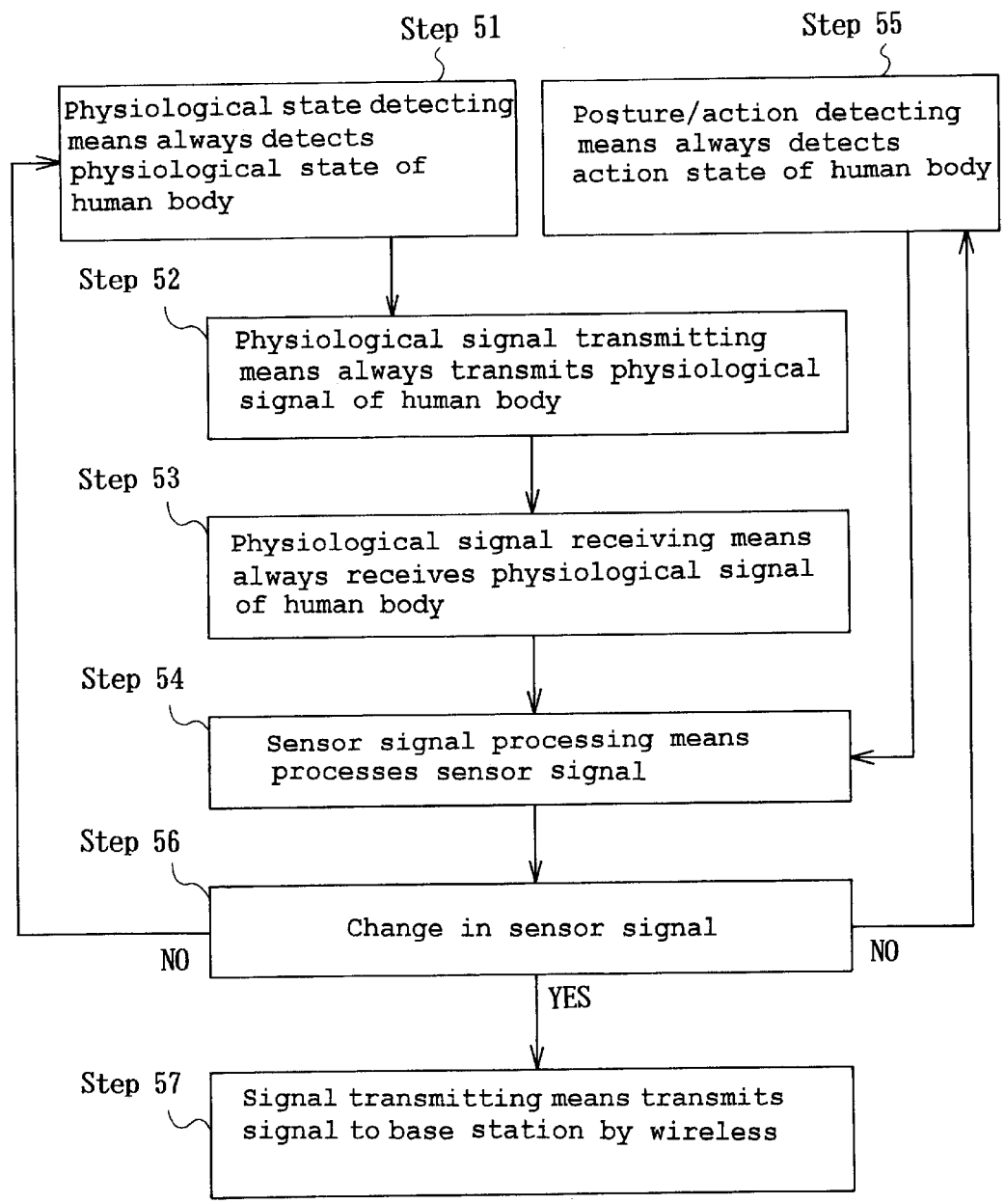
FIG. 22 is an operation diagram of a state information detection and transmission apparatus according to Embodiment 12 of the invention.

The operation of a state information detection and transmission apparatus according to Embodiment 12 is described below with reference to FIG. 22. FIG. 22 is an operation diagram of the state information detection and transmission apparatus according to Embodiment 12 of the invention. Described below is the operation in the present embodiment.

The physiological state detecting means always detects the physiological state such as pulse and heartbeat of a human body (step 51). The analogue signal obtained from the physiological state detecting means is always transmitted from the physiological signal transmitting means (step 52). The analogue signal transmitted from the physiological signal transmitting means is always received by the physiological signal receiving means (step 53). The received analogue signal is converted into a digital signal by signal processing by the sensor signal processing means (step 54).

On the other hand, the posture/action detecting means composed of an acceleration sensor, a gyrosensor, or the like always detects the motion state of the human body (step 55). The signal obtained from the posture/action detecting means undergoes signal processing by the sensor signal processing means, whereby the posture, body motion, action, and motion state of the human body are detected (step 54).

Only when a change occurs in at least one of the sensor signals obtained from the signal processing (step 56), the processed signal is transmitted from the sensor signal transmitting means to the base station by wireless (step 57). When there is no change in the digital signals (step 56), no sensor signal is transmitted.

As such, only when a change occurs in the digital signal obtained by the signal processing by the sensor signal processing means, the digital signal is transmitted to the base station by wireless. By virtue of this, the sensor signal having a high noise level and a large amount of data can be efficiently transmitted to the base station.

In the present embodiment, the processed signal has been transmitted from the sensor signal transmitting means to the base station (step 57), only when a change occurs in at least one of the sensor signals obtained from the signal processing (step 56). However, the data to be transmitted may be all or part of the sensor signals obtained from the signal processing.

"A change in the signal" in the present embodiment is identical to that in Embodiment 11.

Embodiment 13

Figure 23:
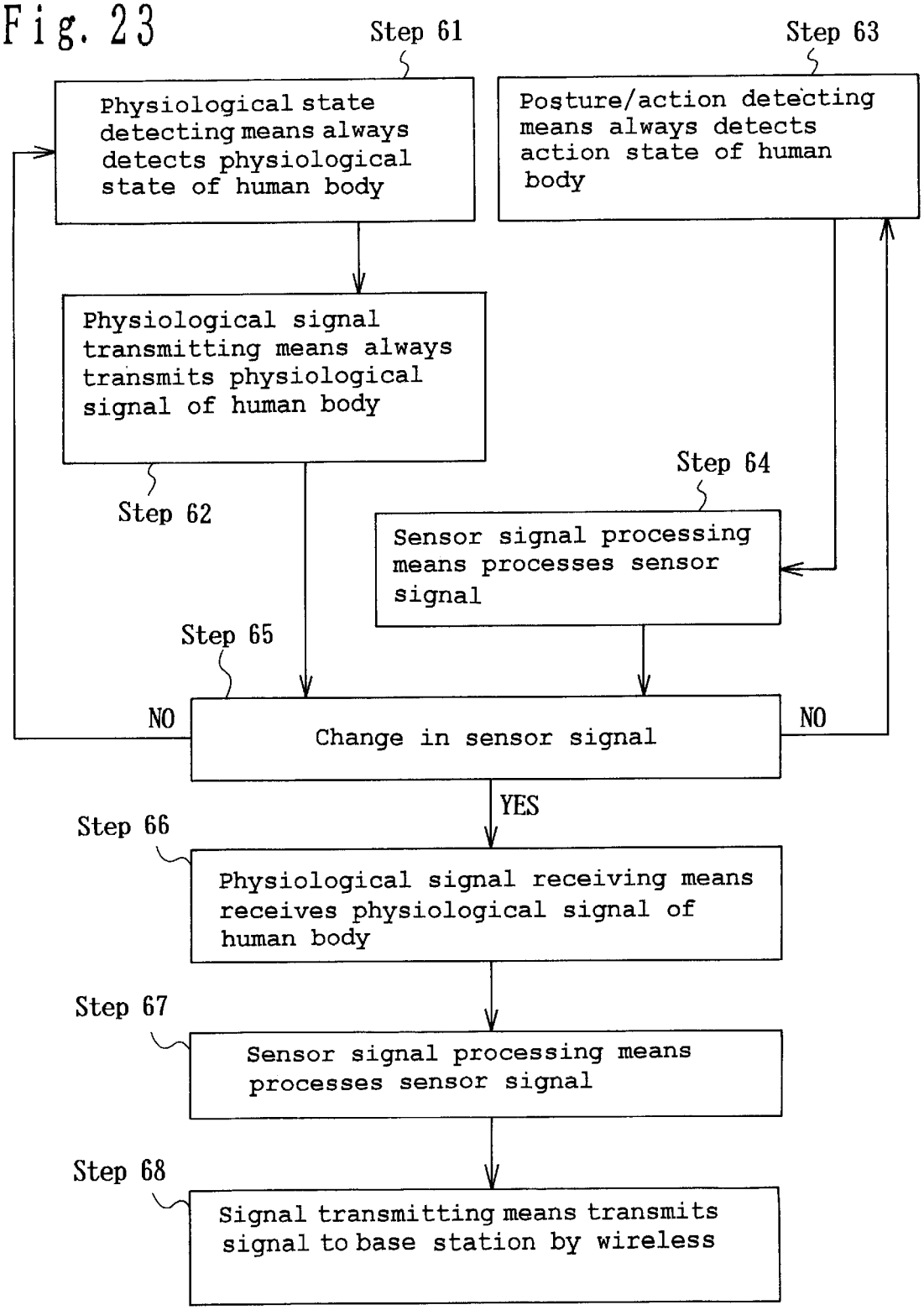
FIG. 23 is an operation diagram of a state information detection and transmission apparatus according to Embodiment 13 of the invention.

A state information detection and transmission apparatus according to Embodiment 13 is described below with reference to the drawings. FIG. 23 is an operation diagram of the state information detection and transmission apparatus according to Embodiment 13 of the invention. Described below are the configuration and the operation in the present embodiment.

The physiological state detecting means composed of an acceleration sensor, a gyrosensor, or the like always detects the physiological state such as pulse and heartbeat of a human body (step 61). The analogue signal obtained from the physiological state detecting means is always transmitted from the physiological signal transmitting means (step 62).

On the other hand, the posture/action detecting means composed of an acceleration sensor, a gyrosensor, or the like always detects the motion state of the human body (step 63). The signal obtained from the posture/action detecting means undergoes signal processing by the sensor signal processing means, whereby the posture, body motion, action, and motion state of the human body are detected (step 64). Only when a substantial change occurs in the sensor signal of the motion state of the human body (step 65), the analogue signal obtained from the physiological signal transmitting means is received by the physiological signal receiving means (step 66).

When there is no change in the sensor signal of the motion state of the human body, the analogue signal obtained from the physiological signal transmitting means is not received by the physiological signal receiving means. Further, the analogue signal received by the physiological signal receiving means is converted into a digital signal by signal processing by the sensor signal processing means (step 67). Then, all or part of the signal-processed data is transmitted from the sensor signal transmitting means to the base station by wireless (step 68).

As such, only when a change occurs in the sensor signal of the posture, body motion, action, and motion state of the human body obtained from the posture/action detecting means, the analogue signal obtained from the physiological signal transmitting means is received by the physiological signal receiving means. By virtue of this, the sensor signal having a high noise level and a large amount of data can be efficiently transmitted to the base station.

"A change in the signal" in the present embodiment is identical to that in Embodiment 11.

Embodiment 14

Figure 24:
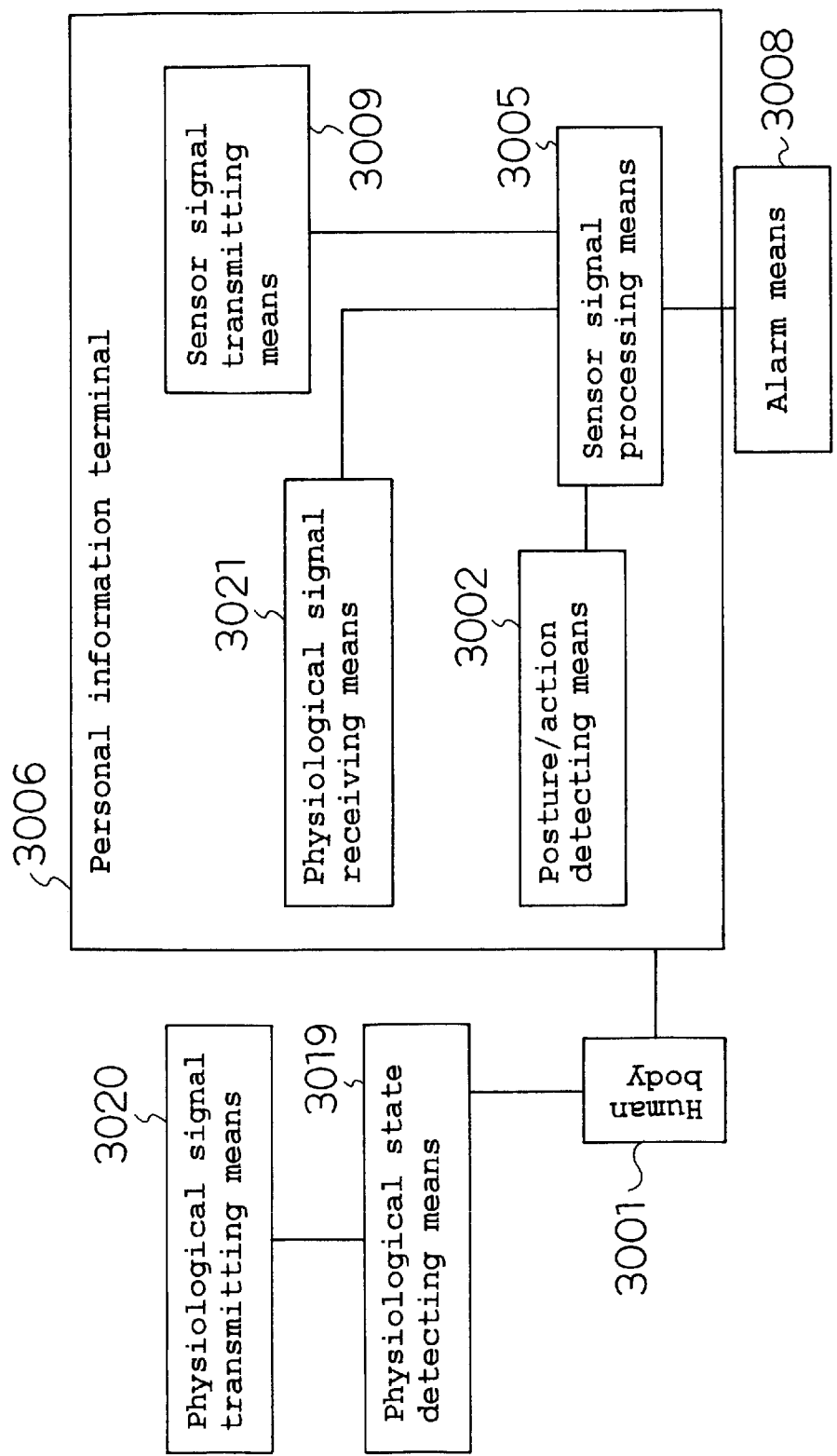
FIG. 24 is a schematic configuration diagram of a state information detection and transmission apparatus according to Embodiment 14 of the invention.

A state information detection and transmission apparatus according to Embodiment 14 is described below with reference to the drawings. FIG. 24 is a schematic configuration diagram of the state information detection and transmission apparatus according to Embodiment 14 of the invention. Described below is the configuration in the present embodiment. The present embodiment comprises a group of sensors composed of a personal information terminal 3006 and physiological state detecting means 3019.

The personal information terminal 3006 is attached to a human body 3001 and comprises: posture/action detecting means 3002 of detecting the posture, body motion, action, and motion state of the human body 3001 by means of an acceleration sensor, a gyrosensor, or the like; physiological signal receiving means 3021 of receiving a sensor signal transmitted from the physiological signal transmitting means 3020 attached to the physiological state detecting means 3019 attached to the human body 3001; sensor signal processing means 3005 of processing the sensor signals obtained from these sensors; sensor signal transmitting means 3009 of transmitting the sensor signals to the base station by wireless; and alarm means 3008 of generating an alarm from an alarm section when an abnormal value is detected in the physiological signal among the signals obtained from the sensor signal processing means 3005.

The physiological state detecting means 3019 detects the physiological information such as pulse and heartbeat of the human body 3001. The analogue signal obtained from the physiological state detecting means 3019 is transmitted from the physiological signal transmitting means 3020. The analogue signal transmitted from the physiological signal transmitting means 3020 is received by the physiological signal receiving means 3021. The received analogue signal is converted into a digital signal by signal processing by the sensor signal processing means 3005.

On the other hand, the signal obtained from the posture/action detecting means 3002 composed of an acceleration sensor, a gyrosensor, or the like undergoes signal processing by the sensor signal processing means 3005, whereby the posture, body motion, action, and motion state of the human body 3001 are detected.

Only when a change occurs in at least one of the digital signals obtained from the sensor signal processing means 3005, all or part of the signal-processed data is transmitted to the base station by the sensor signal transmitting means 3009.

When an abnormal value is detected in the physiological signal among the signals obtained from the sensor signal processing means 3005, the alarm means 3008 generates an alarm from the alarm section. Here, the abnormal value indicates a predetermined value. The alarm means 3008 may generate an alarm from the alarm section, also when an abnormal value is detected in a signal other than the physiological signal among the signals obtained from the sensor signal processing means 3005. Furthermore, the alarm may be generated by means of a sound, as described above, or a color such as red.

Figure 25:
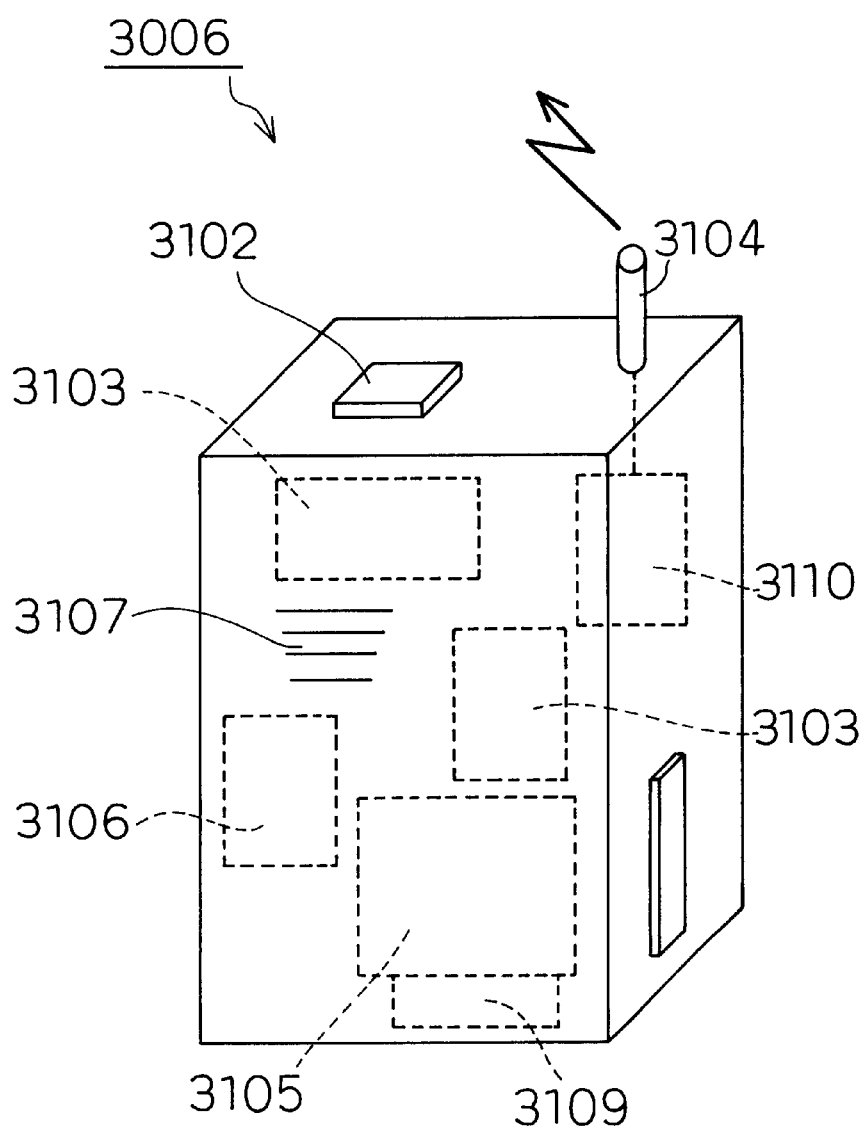
FIG. 25 is a schematic configuration diagram of a personal information terminal 3006 according to Embodiment 14 of the invention.

The personal information terminal 3006 according to Embodiment 14 is described below with reference to the drawings. FIG. 25 is a schematic configuration diagram of the personal information terminal 3006 according to Embodiment 14.

The personal information terminal 3006 is attached to a part of a human body, for example, to the waist using a belt, thereby detecting the posture, the state of walking, the movement path, and the like using an acceleration sensor 3103. As for the posture, the inclination of the human body is obtained by measuring the force component of the gravity using the triaxial acceleration sensor. For the state of walking, the gravity direction output from the acceleration sensor is analyzed by a sensor signal processing circuit 3105, whereby it is determined that the state is static or walking, and that the state of walking is upstairs or downstairs.

The physiological signal receiving means 3109 receives the physiological signal transmitted from the sensor signal transmitting means attached to the physiological state detecting means. The signal is transformed into heartbeat rate and the like by the sensor signal processing circuit 3105. These signals from the internal sensors are analyzed into various state information by the sensor signal processing circuit 3105. The results are transmitted as personal characteristics information through a transmitting and receiving section 3110, through an antenna 3104, and to the base station.

When an abnormal value is detected in the physiological signal among the signals obtained from the sensor signal processing means 3005, the alarm buzzer 3107 generates an alarm. That is, in case of abnormality, this buzzer calls the person carrying personal information terminal 3006, and an abnormal state signal is transmitted through the antenna 3104. When the abnormal state signal is transmitted, a helper checks the situation of the person, and/or the situation is notified to the outside. All the above-mentioned means are powered by an internal battery 3106.

Embodiment 15

A state information detection and transmission apparatus according to Embodiment 15 is described below. Described below is the configuration in the present embodiment.

The physiological state detecting means always detects the physiological information such as pulse and heartbeat of the human body. The analogue signal obtained from the physiological state detecting means is always transmitted from the physiological signal transmitting means.

On the other hand, the posture/action detecting means composed of an acceleration sensor, a gyrosensor, or the like always detects the motion state of the human body. The signal obtained from the posture/action detecting means undergoes signal processing by the sensor signal processing means, whereby the posture, body motion, action, and motion state of the human body are detected. Only when a change occurs in the sensor signal of the motion state of the human body, the analogue signal obtained from the physiological signal transmitting means is received by the physiological signal receiving means.

When there is no change in the sensor signal of the motion state of the human body, the analogue signal obtained from the physiological signal transmitting means is not received by the physiological signal receiving means.

The received analogue signal is converted into a digital signal by signal processing by the sensor signal processing means. Then, all or part of the signal-processed data is transmitted from the sensor signal transmitting means to the base station by wireless.

Further, the personal information terminal may provided with an alarm button for notifying an abnormality in the human body. The alarm may be generated by pushing the alarm button, as color or sound from the alarm section.

The alarm is generated when the human body arbitrarily pushes the alarm button in order to notify the abnormality. That is, the apparatus is used in order to call another person when the person carrying this apparatus detects an abnormality. Further, the abnormal state signal may be transmitted from the antenna of the personal information terminal when the alarm button is pushed. When the abnormal state signal is transmitted, a helper checks the situation of the person, and/or the situation is notified to the outside.

Embodiment 16

Figure 26:
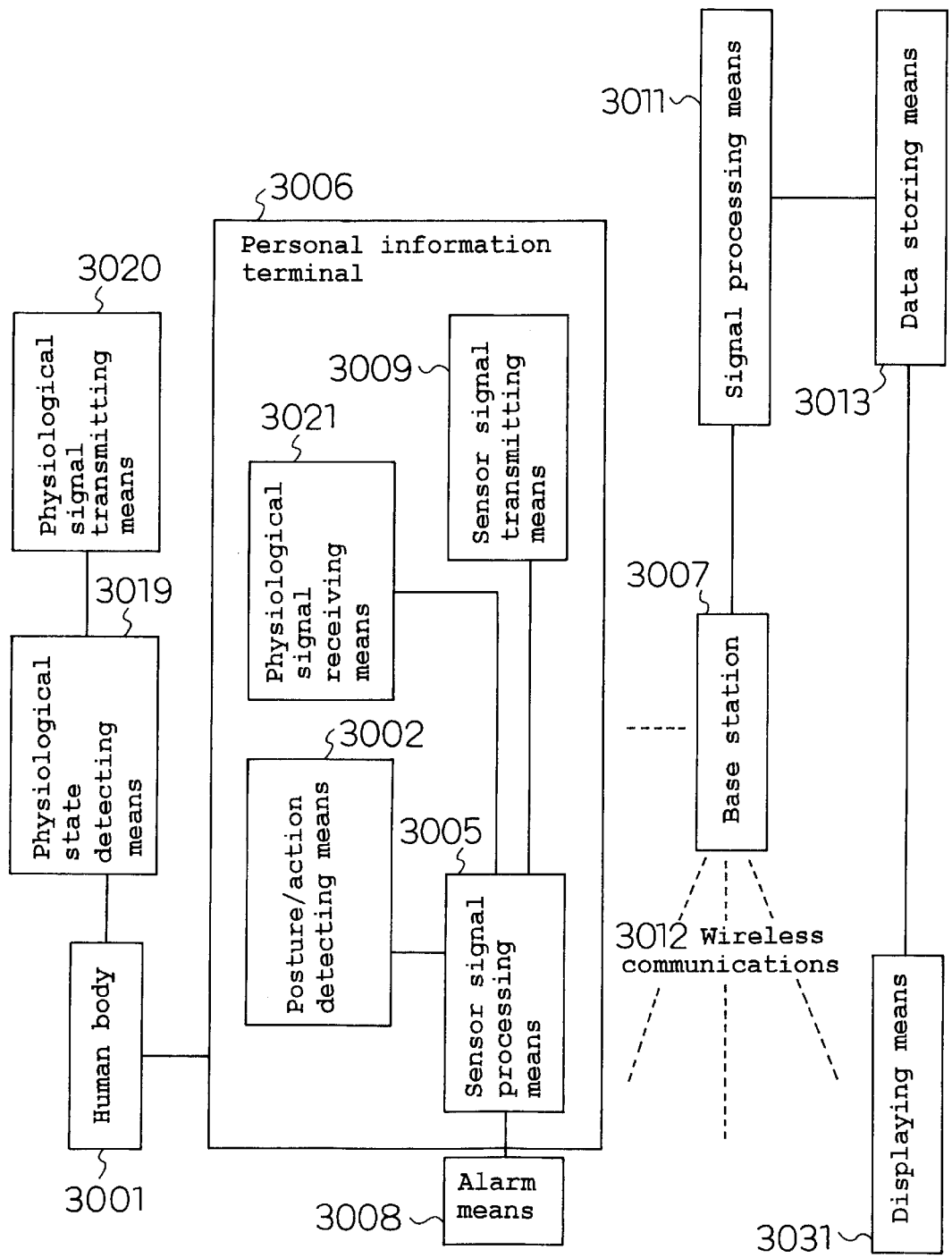
FIG. 26 is a schematic diagram of a personal characteristics information acquisition system according to Embodiment 16 of the invention.

A personal characteristics information acquisition system according to Embodiment 16 is described below with reference to the drawings. FIG. 26 is a schematic configuration diagram of the personal characteristics information acquisition system according to Embodiment 16 of the invention. Described below is the configuration in the present embodiment. The present embodiment comprises a group of sensors composed of a personal information terminal 3006 and physiological state detecting means 3019.

The personal information terminal 3006 is attached to a human body 3001 and comprises: posture/action detecting means 3002 of detecting the posture, body motion, action, and motion state of the human body 3001 by means of an acceleration sensor, a gyrosensor, or the like; physiological signal receiving means 3021 of receiving a sensor signal transmitted from the physiological signal transmitting means 3020 attached to the physiological state detecting means 3019 attached to the human body 3001; sensor signal processing means 3005 of processing the sensor signals obtained from these sensors; sensor signal transmitting means 3009 of transmitting the sensor signals to the base station 3007 by wireless communications 3012; and alarm means 3008 of generating an alarm from an alarm section when an abnormal value is detected in the physiological signal among the signals obtained from the sensor signal processing means 3005.

The sensor information of the personal information terminal 3006 transmitted to the base station 3007 by wireless communications 3012 is sent to the sensor signal processing means 3011. The action information of the human body 3001 received by the signal processing means 3011 is transferred via a network to the data storing means 3013, and temporarily stored as structured data in the data storing means 3013. When a displaying apparatus 3031 such as monitor is provided in the data storing means 3013 storing the data, the action state of the person in every room can be viewed at one time.

The signal processing means 3011, together with other signal processing means, is connected to the network. By virtue of this network connection, the information in every room can be used in common, whereby the action state of the person in every room can be understood. This reduces substantially the load on helpers in an ordinary home as well as in an institution for the nursing care of elderlies. In the present embodiment, the kind of the network is not restricted, and the network may be arbitrary one.

Embodiment 17

Figure 27:
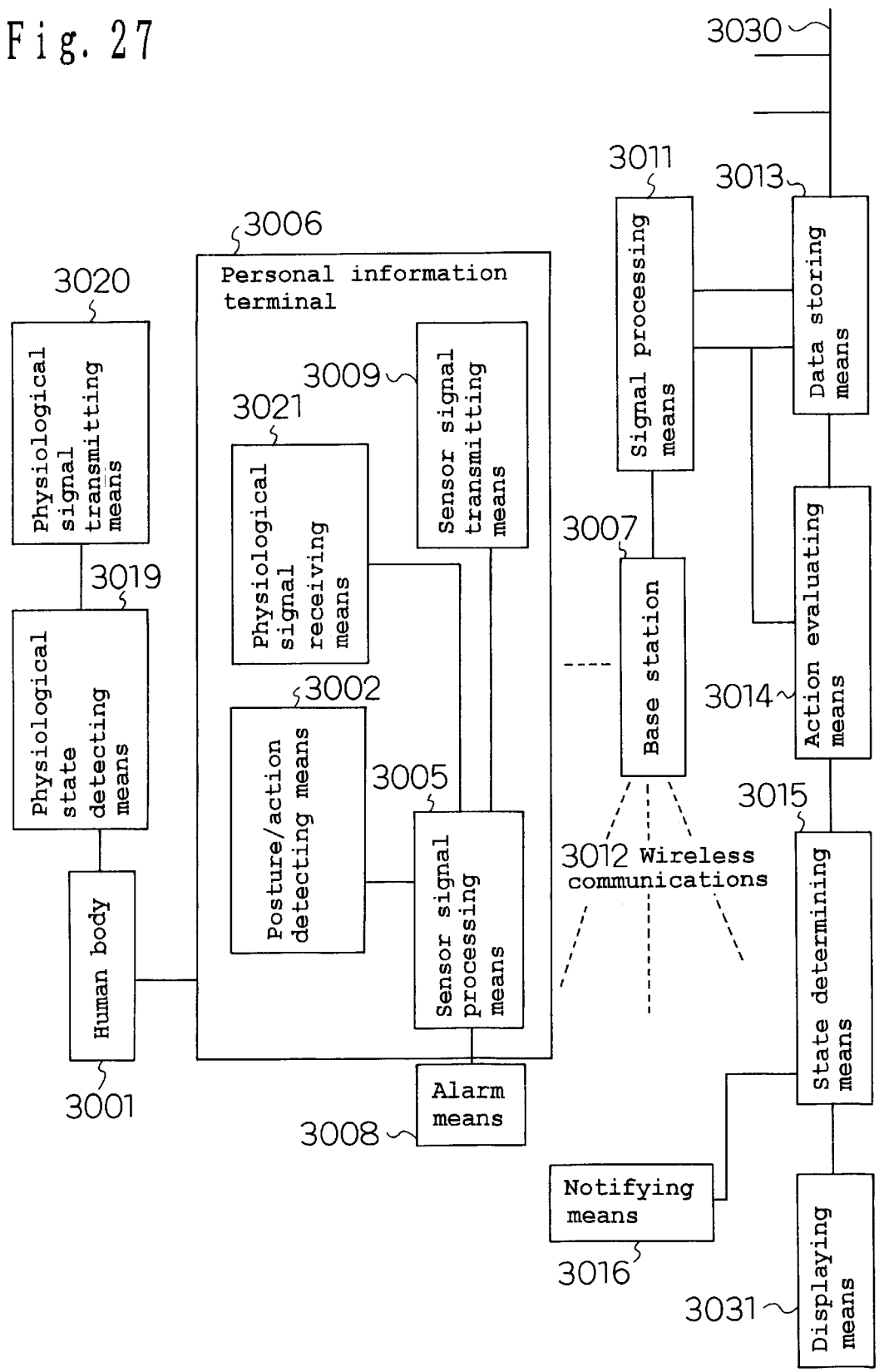
FIG. 27 is a schematic diagram of a personal characteristics information acquisition system according to Embodiment 17 of the invention.

A personal characteristics information acquisition system according to Embodiment 17 is described below with reference to the drawings. FIG. 27 is a schematic configuration diagram of the personal characteristics information acquisition system according to Embodiment 17 of the invention. Described below is the configuration in the present embodiment. The present embodiment comprises a group of sensors composed of a personal information terminal 3006 and physiological state detecting means 3019.

The personal information terminal 3006 is attached to a human body 3001 and comprises: posture/action detecting means 3002 of detecting the posture, body motion, action, and motion state of the human body 3001 by means of an acceleration sensor, a gyrosensor, or the like; physiological signal receiving means 3021 of receiving a sensor signal transmitted from the physiological signal transmitting means 3020 attached to the physiological state detecting means 3019 attached to the human body 3001; sensor signal processing means 3005 of processing the sensor signals obtained from these sensors; sensor signal transmitting means 3009 of transmitting the sensor signals to the base station 3007 by wireless communications 3012; and alarm means 3008 of generating an alarm from an alarm section when the human body 3001 arbitrarily pushes it in order to notify the abnormality.

The sensor information of the personal information terminal 3006 transmitted to the base station 3007 by wireless communications 3012 is sent to the signal processing means 3011. The action information of the human body 3001 received by the signal processing means 3011 is transferred via a network 3030 to the data storing means 3013, and temporarily stored as structured data in the data storing means 3013. The action information of human body 3001 obtained from the signal processing means 3011 undergoes comparison and evaluation in the action evaluating means 3014 on the basis of the structured data having been accumulated in the data storing means 3013.

When the action state of human body obtained from the action evaluating means 3014 is determined to be abnormal or predicted to become abnormal as a possibility in the future by the state determining means 3015, the notifying means 3016 notifies it to the person. Further, when a displaying apparatus 3031 such as monitor is provided, the action state of the person in every room can be viewed at one time.

The signal processing means 3011, together with other signal processing means, is connected to the network. By virtue of this network connection, the information in every room can be used in common, whereby the action state of the person in every room can be understood. This reduces substantially the load on helpers in an ordinary home as well as in an institution for the nursing care of elderlies. In the present embodiment, the kind of the network is not restricted, and the network may be arbitrary one.

Embodiment 18

Figure 28:
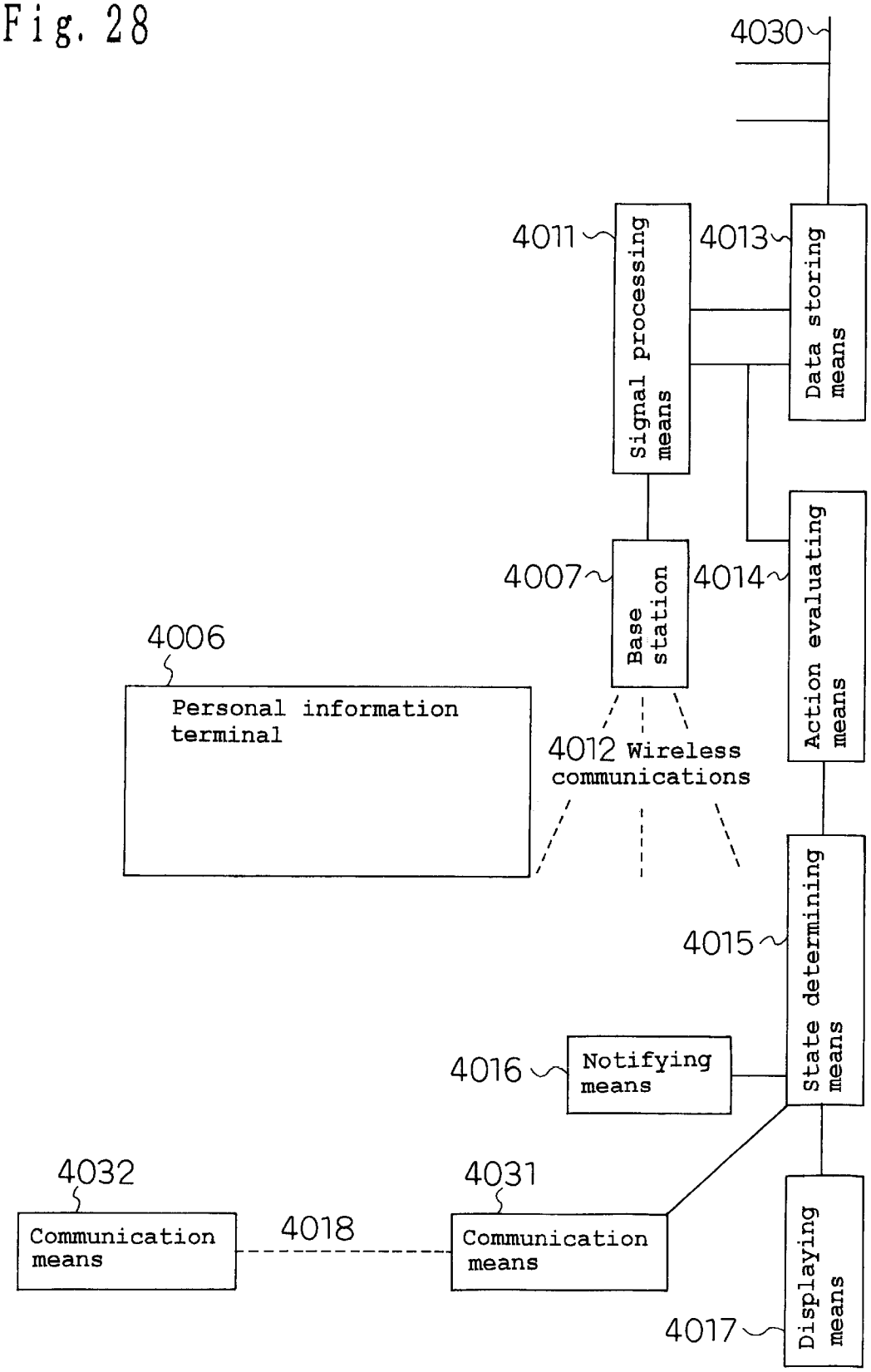
FIG. 28 is a schematic configuration diagram of an action detection system according to Embodiment 18 of the invention.

An action detection system according to Embodiment 18 is described below with reference to the drawings. FIG. 28 is a schematic configuration diagram of the action detection system according to Embodiment 18 of the invention. Described below is the configuration in the present embodiment.

The wearable personal information terminal 4006 is attached to a human body and detects the posture, body motion, action, and motion state of the human body as well as a physiological signal. These detected and acquired sensor signals are transmitted to a base station 4007 by wireless communications 4012.

The sensor information of the personal information terminal 4006 transmitted to the base station 4007 by wireless communications 4012 is sent to the signal processing means 4011 connected to other sensors, whereby the information is integrated. The action information of the human body integrated by the signal processing means 4011 is transferred via a network 4030 to the data storing means 4013, and temporarily stored as structured data in the data storing means 4013.

The action information of human body obtained from the signal processing means 4011 undergoes comparison and evaluation in the action evaluating means 4014 on the basis of the structured data having been accumulated in the data storing means 4013. When the action state of human body obtained from the action evaluating means 4014 is determined to be abnormal or predicted to become abnormal as a possibility in the future by the state determining means 4015, the notifying means 4016 capable of notifying it to the personal information terminal 4006 and other personal information terminals connected to the network or the Internet notifies it to the person or another person. Here, the state determining means 4015 performs the above-mentioned determination and prediction by comparing the action information obtained from the action evaluating means 4014 with predetermined reference information.

When the state determining means 4015 determines an abnormality, the information indicating the situation is transmitted from communication means (first Internet terminal) 4031 to another communication means (second Internet terminal) 4032 via the Internet 4018. Then, when the user of the communication means (second Internet terminal) 4032 is a doctor, the doctor can give an appropriate advice to the person having the abnormality or the person's helper by the interactive communications via the Internet 4018. Further, when the information transmitted from the communication means (first Internet terminal) 4031 to the communication means (second Internet terminal) 4032 via the Internet 4018 includes the action information obtained from the action evaluating means 4014, the doctor can give a more appropriate advice based on the action information.

When a displaying apparatus 4017 such as monitor is connected to the state determining means 4015, the action state of the person in every room can be viewed at one time.

The signal processing means 4011, together with other signal processing means, is connected to the network. By virtue of this network connection, the information in every room can be used in common, whereby the action state of the person in every room can be understood. This reduces substantially the load on helpers in an ordinary home as well as in an institution for the nursing care of elderlies. In the present embodiment, the kind of the network is not restricted, and the network may be arbitrary one.

In the present embodiment, the information indicating abnormality has been transmitted from the communication means 4031 to the communication means 4032 via the Internet 4018 when the state determining means 4015 has determined an abnormality. However, even in case of non-abnormality, the information indicating the situation, or alternatively this information and the action state information, maybe transmitted. In this case, for example, the doctor can understand the state such as presence or absence of an abnormality in the person of object of detection.

In order for the communication means (first Internet terminal) 4031 and the communication means (second Internet terminal) 4032 to be interconnected via the Internet 4018 automatically when the state determining means 4015 determines an abnormality, the communication means 4031 preferably has the address of the communication means 4032 or the information necessary to specify the address, in advance.

Further, the communication means (first Internet terminal) 4031 may comprise a button used for interconnecting the communication means 4031 and the communication means (second Internet terminal) 4032 via the Internet 4018 using the above-mentioned address or the information necessary to specify the address. In this case, when the button is pushed, the communication means 4031 and the communication means 4032 are interconnected via the Internet 4018.

Embodiment 19

Figure 29:
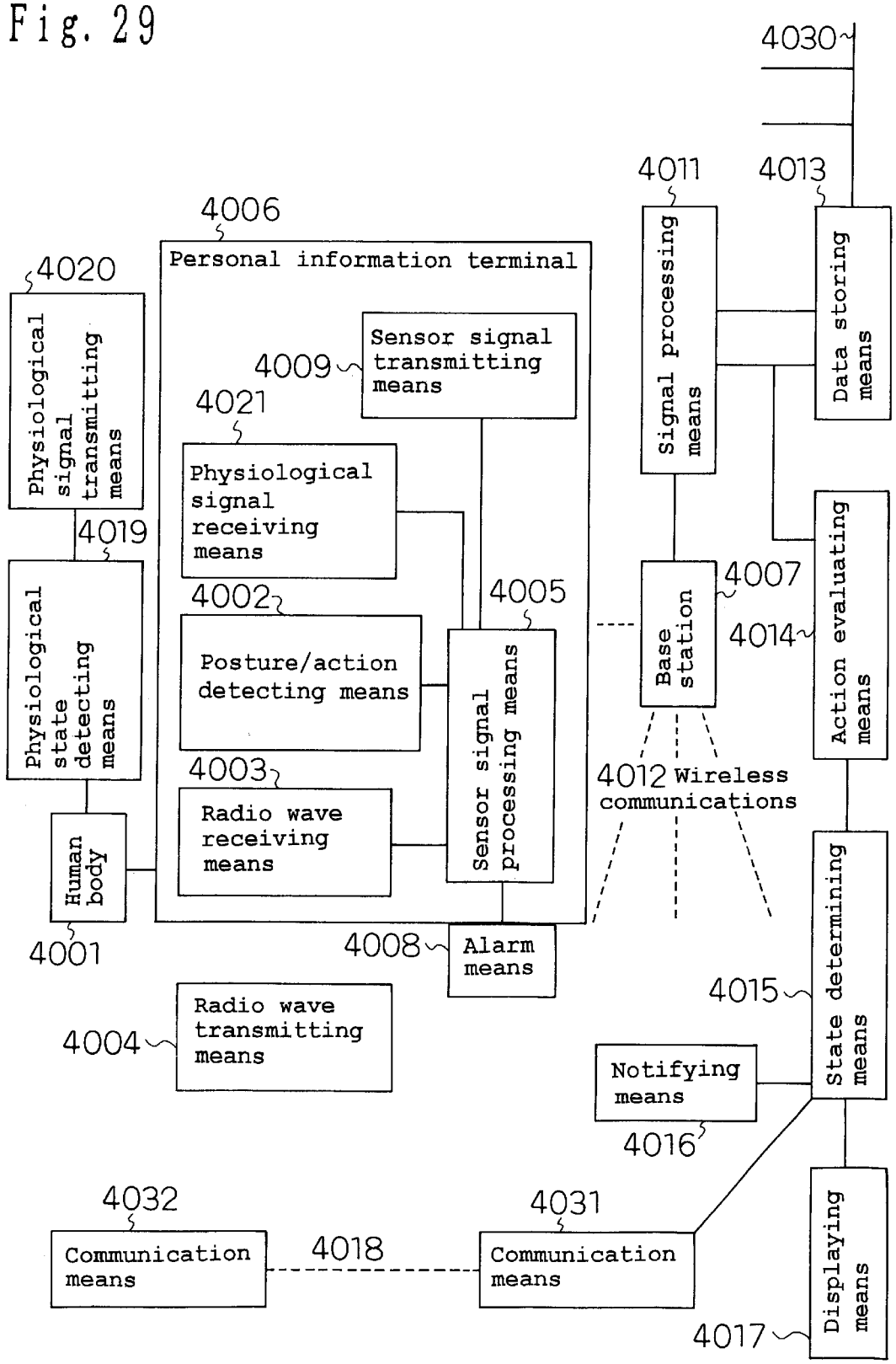
FIG. 29 is a schematic configuration diagram of an action detection system according to Embodiment 19 of the invention.

An action detection system according to Embodiment 19 is described below with reference to the drawings. FIG. 29 is a schematic configuration diagram of the action detection system according to Embodiment 19 of the invention. Described below is the configuration in the present embodiment.

The personal information terminal 4006 is attached to a human body 4001 and comprises: posture/action detecting means 4002 of detecting the posture, body motion, action, and motion state of the human body 4001 by means of an acceleration sensor, a gyrosensor, or the like; radio wave receiving means 4003 of receiving a radio wave of specific frequency transmitted from radio wave transmitting means 4004 when the distance from the radio wave transmitting means 4004 is a predetermined value or less; physiological signal receiving means 4021 of receiving a sensor signal transmitted from the physiological signal transmitting means 4020 attached to the physiological state detecting means 4019 attached to the human body 4001; sensor signal processing means 4005 of processing the signals obtained from the sensors; and sensor signal transmitting means 4009 of transmitting these sensor signals to a base station 4007 by wireless communications 4012.

The sensor information of the personal information terminal 4006 transmitted to the base station 4007 by wireless communications 4012 is sent to the signal processing means 4011 connected to other sensors, whereby the information is integrated. The action information of the human body integrated by the signal processing means 4011 is transferred via a network 4030 to the data storing means 4013, and temporarily stored as structured data in the data storing means 4013.

The action information of human body obtained from the signal processing means 4011 undergoes comparison and evaluation in the action evaluating means 4014 on the basis of the structured data having been accumulated in the data storing means 4013. When the action state of human body obtained from the action evaluating means 4014 is determined to be abnormal or predicted to become abnormal as a possibility in the future by the state determining means 4015, the notifying means 4016 capable of notifying it to the alarm means 4008 of the personal information terminal 4006 and other personal information terminals connected to the network or the Internet notifies it to the person or another person. Here, the state determining means 4015 performs the above-mentioned determination and prediction by comparing the action information obtained from the action evaluating means 4014 with predetermined reference information.

When the state determining means 4015 determines an abnormality, the information indicating the situation is transmitted from the communication means (first Internet terminal) 4031 to the communication means (second Internet terminal) 4032 via the Internet 4018. Then, when the user of the communication means (second Internet terminal) 4032 is a doctor, the doctor can give an appropriate advice to the person having the abnormality or the person's helper by the interactive communications via the Internet 4018. Further, when the information transmitted from the communication means (first Internet terminal) 4031 to the communication means (second Internet terminal) 4032 via the Internet 4018 includes the action information obtained from the action evaluating means 4014, the doctor can give a more appropriate advice based on the action information.

When a displaying apparatus 4017 such as monitor is connected to the state determining means 4015, the action state of the person in every room can be viewed at one time.

The signal processing means 4011, together with other signal processing means, is connected to the network. By virtue of this network connection, the information in every room can be used in common, whereby the action state of the person in every room can be understood. This reduces substantially the load on helpers in an ordinary home as well as in an institution for the nursing care of elderlies. In the present embodiment, the kind of the network is not restricted, and the network may be arbitrary one.

Figure 30:
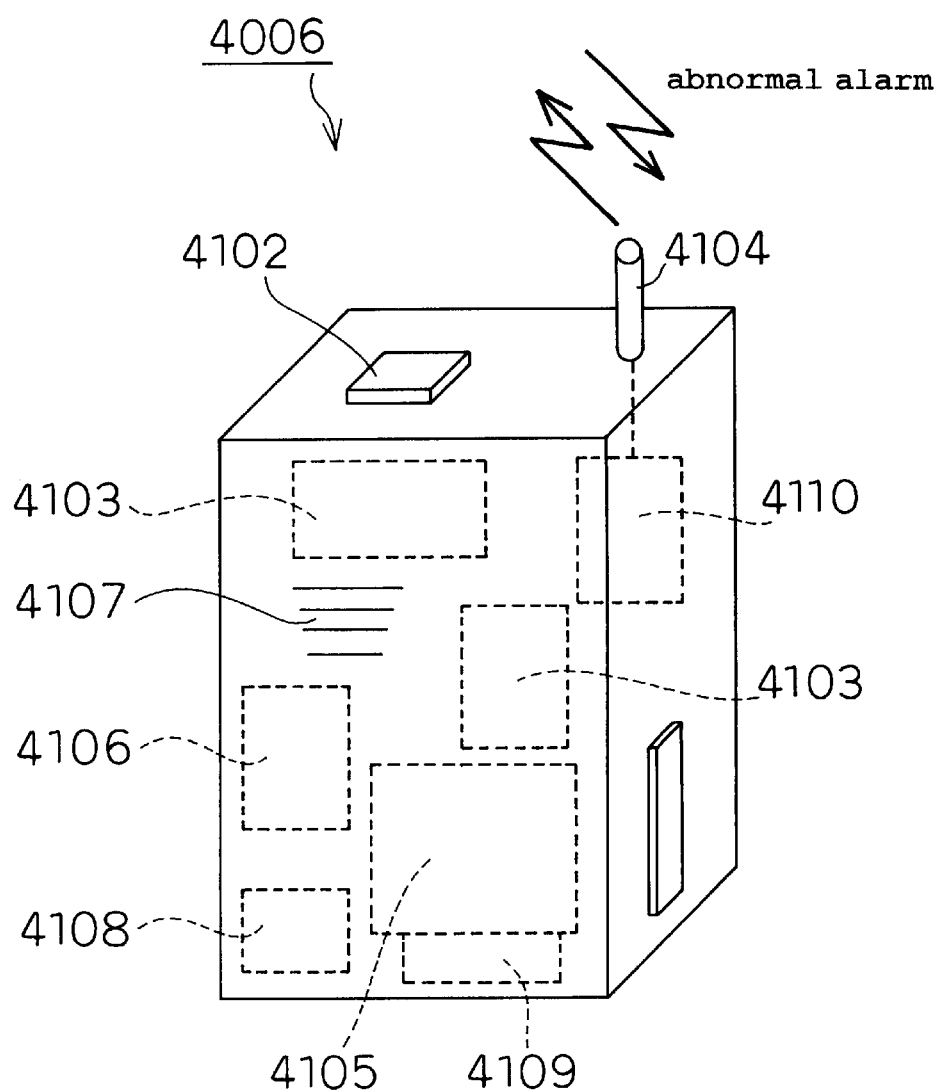
FIG. 30 is a schematic diagram of a personal information terminal 4006 according to Embodiment 19 of the invention.

The personal information terminal 4006 according to Embodiment 19 is described below with reference to the drawings. FIG. 30 is a schematic configuration diagram of the personal information terminal 4006 according to Embodiment 19.

The personal information terminal 4006 is attached to a part of a human body, for example, to the waist using a belt, thereby detecting the posture, the state of walking, the movement path, and the like using an acceleration sensor 4103 or a gyrosensor. As for the posture, the inclination of the human body is obtained by measuring the force component of the gravity using the triaxial acceleration sensor. For the state of walking, the gravity direction output from the acceleration sensor is analyzed by a sensor signal processing circuit 4105, whereby it is determined that the state is static or walking, and that the state of walking is upstairs or downstairs.

A coil 4108 receives the radio wave transmitted from the radio wave transmitting means 4004 (see FIG. 29). The signal is transformed into position information by the sensor signal processing circuit 4105. A sensor signal receiving means 4109 receives the physiological signal transmitted from the sensor signal transmitting means 4020 (see FIG. 29) attached to physiological state detecting means 4019 (see FIG. 29). The signal is transformed into heartbeat rate and the like by the sensor signal processing circuit 4105. These signals are analyzed into various state information by the sensor signal processing circuit 4105. The results are transmitted as personal characteristics information through a transmitting and receiving section 4110, through an antenna 4104, and to the base station 4007 (see FIG. 29).

When there has been no human body movement for a long time, or when an abnormal state is detected, determined, or predicted, an alarm buzzer 4107 calls the person carrying this personal information terminal 4006. When there is no response, for example, by pushing a switch 4102, to this call, an abnormal state signal is transmitted through the antenna 4104. When the abnormal state signal is transmitted, a helper checks the situation of the person, and/or the situation is notified to the outside. All the above-mentioned means are powered by an internal battery 4106.

The present embodiment has been described for the case of an acceleration sensor or a gyrosensor. However, the invention is not restricted to this, and the posture information may be obtained by an inclination angle sensor.

Figure 31:
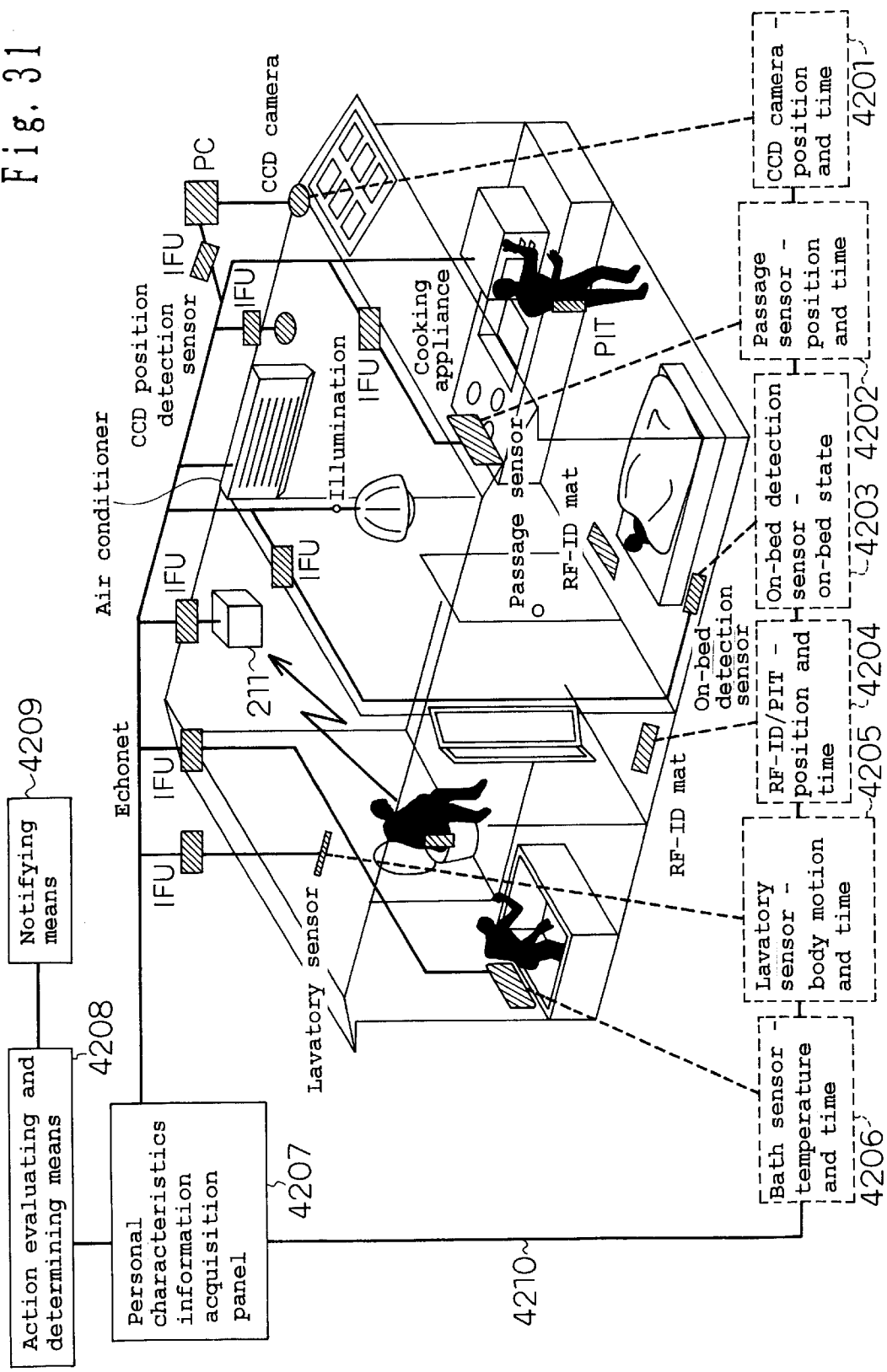
FIG. 31 is a schematic diagram of a house provided with action detection system according to Embodiment 19 of the invention.

The action detection system according to Embodiment 19 is further described with reference to the drawings. FIG. 31 is a schematic configuration diagram of a house provided with the action detection system according to Embodiment 19 of the invention. Described below is the configuration in the present embodiment.

The position detecting means 4201 is either means of detecting and specifying the position of the human body by means of image processing using a CCD camera, an infrared sensor, or an infra-red camera, the latter two being capable of measuring the two-dimensional temperature distribution, or means of specifying the position of the human body or article by means of: a radio wave source attached to the human body or article; and one or more antennas which are located in the room and detect the intensity or the direction of the radio wave. The signal processing means or IFU processes the signal obtained from the CCD camera, the infra-red sensor, or the antennas, thereby calculating the two-dimensional coordinates on the floor of the room.

A passage sensor 4202 provides a sensor output corresponding to the movement direction of the human body or article by means of an infra-red sensor, a distance sensor, or the like. The sensor signal output from the passage sensor is processed by signal processing means, thereby permitting the determination of the movement direction of entering or exiting the room by the human body or article.

The on-bed state detecting means 4203 detects an abnormal state of a human body on a bed, and provides a sensor output corresponding to the posture of the human body by means of an infra-red sensor, a pressure sensor, or the like. The sensor signal output from the on-bed state detecting means is processed by signal processing means, and then used in the determination of the presence or absence, the posture, and an abnormal state of the human body.

The personal information terminal 4204 is attached to a human body and comprises: posture/action detecting means of detecting the posture, body motion, action, and motion state of the human body by means of an acceleration sensor, a gyrosensor, or the like; radio wave receiving means of receiving a radio wave of specific frequency transmitted from radio wave transmitting means when the distance from an RF-ID mat of the radio wave transmitting means is a predetermined value or less; physiological signal receiving means of receiving a sensor signal transmitted from the physiological signal transmitting means attached to the physiological state detecting means attached to the human body; sensor signal processing means of processing the signals obtained from the sensors; and sensor signal transmitting and receiving means of transmitting these sensor signals to a base station 4211 by wireless.

The human body state detecting means 4205 detects an abnormal state of a human body in a lavatory, and provides a sensor output corresponding to the posture of the human body by means of an infra-red sensor, a distance sensor, or the like. The sensor signal output from the human body state detecting means is processed by signal processing means, and then used in the determination of the state of entering or exiting the room, the posture, and an abnormal state of the human body.

The bath sensor 4206 detects an abnormal state of a human body in a bath, and provides a sensor output corresponding to the posture of the human body by means of an infra-red sensor, a distance sensor, or the like. The sensor signal output from the bath sensor is processed by signal processing means, and then used in the determination of the state of entering or exiting the room, the posture, and an abnormal state of the human body.

The sensor information of the personal information terminal 4204 transmitted to the base station 4211 by wireless is sent to a personal characteristics information acquisition panel 4207 connected to other sensors of the CCD position detection sensor 4201, the passage sensor 4202, the on-bed state detection sensor 4203, the lavatory sensor 4205, and the bath sensor 4206 via the network 4210, whereby the information is integrated. The action information of the human body integrated by the personal characteristics information acquisition panel 4207 is transferred to the data storing means, and temporarily stored as structured data in the data storing means.

The action information of human body obtained from the personal characteristics information acquisition panel 4207 undergoes comparison and evaluation in the action evaluating means 4208 on the basis of the structured data having been accumulated in the data storing means. When the action state of human body obtained from the action evaluating means 4208 is determined to be abnormal or predicted to become abnormal as a possibility in the future by the state determining means 4208, the notifying means 4209 capable of notifying it to the alarm means of the personal information terminal and other personal information terminals connected to the network or the Internet notifies it to the person or another person.

Further, the system is configured such that in case of abnormality, the interactive communications can be carried out between the human body having an abnormality and the person received the notification. Furthermore, when a displaying apparatus such as monitor is provided in the state determining means, the action state of the person in every room can be viewed at one time.

Embodiment 20

An action detection system according to Embodiment 20 is described below with reference to the drawings. Described below is the configuration in the present embodiment.

The personal information terminal is attached to a human body and comprises: posture/action detecting means of detecting the posture, body motion, action, and motion state of the human body by means of an acceleration sensor, a gyrosensor, or the like; radio wave receiving means of receiving a radio wave of specific frequency transmitted from radio wave transmitting means when the distance from the radio wave transmitting means is a predetermined value or less; physiological signal receiving means of receiving a sensor signal transmitted from the physiological signal transmitting means attached to the physiological state detecting means attached to the human body; sensor signal processing means of processing the signals obtained from the sensors; and sensor signal transmitting and receiving means of transmitting these sensor signals to the base station by wireless.

The sensor information of the personal information terminal transmitted to the base station by wireless is sent to the sensor signal processing means connected to other sensors, whereby the information is integrated. The action information of the human body integrated by the sensor signal processing means is transferred to the data storing means, and temporarily stored as structured data in the data storing means.

The action information of human body obtained from the sensor signal processing means undergoes comparison and evaluation in the action evaluating means on the basis of the structured data having been accumulated in the data storing means. When the action state of human body obtained from the action evaluating means is determined to be abnormal or predicted to become abnormal as a possibility in the future by the state determining means, the notifying means capable of notifying it to the alarm means of the personal information terminal and other personal information terminals connected to the network or the Internet notifies it to the person or another person.

Further, the system is configured such that in case of abnormality, a person is sent to the human body having an abnormality. Furthermore, when a displaying apparatus such as monitor is provided in the state determining means, the action state of the person in every room can be viewed at one time.

The sensor signal processing means, together with other sensor signal processing means, is connected to the network. By virtue of this network connection, the information in every room can be used in common, whereby the action state of the person in every room can be understood. This reduces substantially the load on helpers in an ordinary home as well as in an institution for the nursing care of elderlies. In the present embodiment, the kind of the network is not restricted, and the network may be arbitrary one.

Embodiment 21

An action detection system according to Embodiment 21 is described below with reference to the drawings. Described below is the configuration in the present embodiment.

The personal information terminal is attached to a human body and comprises: posture/action detecting means of detecting the posture, body motion, action, and motion state of the human body by means of an acceleration sensor, a gyrosensor, or the like; radio wave receiving means of receiving a radio wave of specific frequency transmitted from radio wave transmitting means when the distance from the radio wave transmitting means is a predetermined value or less; physiological signal receiving means of receiving a sensor signal transmitted from the physiological signal transmitting means attached to the physiological state detecting means attached to the human body; sensor signal processing means of processing the signals obtained from the sensors; and sensor signal transmitting and receiving means of transmitting these sensor signals to the base station by wireless.

The sensor information of the personal information terminal transmitted to the base station by wireless is sent to the sensor signal processing means connected to other sensors, whereby the information is integrated. The action information of the human body integrated by the sensor signal processing means is transferred to the data storing means, and temporarily stored as structured data in the data storing means.

The action information of human body obtained from the sensor signal processing means undergoes comparison and evaluation in the action evaluating means on the basis of the structured data having been accumulated in the data storing means. When the action state of human body obtained from the action evaluating means is determined to be abnormal or predicted to become abnormal as a possibility in the future by the state determining means, the notifying means capable of notifying it to the alarm means of the personal information terminal and other personal information terminals connected to the network or the Internet notifies it to the person or another person.

The action detection system according to Embodiment 21 further comprises equipment such as air conditioner, illumination means, and the like which is connected to a network or an Internet terminal, and is arbitrarily adjusted in order to create a comfortable environment in response to the obtained personal action information, for example, by the control commands sent from another Internet terminal to the above-mentioned Internet terminal. Furthermore, when a displaying apparatus such as monitor is provided in the state determining means, the action state of the person in every room can be viewed at one time.

The sensor signal processing means, together with other sensor signal processing means, is connected to the network. By virtue of this network connection, the information in every room can be used in common, whereby the action state of the person in every room can be understood. This reduces substantially the load on helpers in an ordinary home as well as in an institution for the nursing care of elderlies. In the present embodiment, the kind of the network is not restricted, and the network may be arbitrary one.

In the above, Embodiments 1–21 of the invention have been described in detail.

Further, the invention is a program which causes a computer to execute all or part of the steps (or processes, operations, effects, and the like) in the above-mentioned state information acquisition method, state information detection and transmission method, and action detection method according to the invention and works in cooperation with the computer.

The computer according to the invention is not restricted to genuine hardware such as CPU, but may include firmware, OS, and peripheral devices.

Part of the steps (or processes, operations, effects, and the like) in the invention indicates a step or steps in the plurality of steps, or alternatively a part of function or operation in a step.

A computer readable recording medium containing a program according to the invention is also included in the scope of the invention. A mode of use of a program according to the invention may be the mode in which the program is recorded in a computer readable recording medium and works in cooperation with a computer. Further, a mode of use of a program according to the invention may be the mode in which the program is transferred in a transferring medium and read by a computer thereby to work in cooperation with a computer. The recording media include a ROM, while the transferring media include: a transferring medium such as the Internet; light; radio wave; and sound wave.

The configuration according to the invention may be implemented by software or hardware.

Further, the invention is a medium which carries a program causing a computer to execute all or part of the steps (or processes, operations, effects, and the like) in the above-mentioned state information acquisition method, state information detection and transmission method, and action detection method according to the invention and is readable by a computer, wherein the read-out program executes the operation in cooperation with the computer.

The entire disclosure of the above-mentioned references is incorporated herein by reference in its entirety.

(A) As described above, the present invention advantageously provides a state information acquisition system, a state information acquisition apparatus, an attachable terminal apparatus, a state information acquisition method, a personal characteristics information acquisition system, a program, and a medium for directly obtaining the physiological state of a person.

Further, the present invention advantageously provides a state information acquisition system, a state information acquisition apparatus, an attachable terminal apparatus, a state information acquisition method, a personal characteristics information acquisition system, a program, and a medium for obtaining more detailed information on the state of a person.

(B) Further, the present invention advantageously provides a state information acquisition system, a state information acquisition apparatus, a state information acquisition method, an abnormal action detection system, a program, and a medium for integrally obtaining state information indicating the state of a person or an animal.

(C) Further, the present invention advantageously provides a state information detection and transmission apparatus and the like capable of reducing the amount of data of: physiological information transmitted from transmitting means to a personal information terminal; physiological information transmitted from the personal information terminal to a base station; and information on all or part of posture, action, and motion state of a human body, transmitted from the personal information terminal to the base station.

Accordingly, a personal information terminal according to the invention can reduce efficiently the amount of data of the physiological signal having a high noise level and a large amount of data, by setting the timing of receiving the physiological signal to be in every predetermined time interval or setting the timing of transmitting the physiological signal to be at a time only when a change occurs in the physiological signal. This avoids advantageously the transmission of unnecessary data signals to the base station.

A personal information terminal according to the invention can immediately notify an abnormality to the person or another person, by setting the timing of alarm to be a time when an abnormal value is detected in the physiological signal obtained from the physiological state detecting means or a time when the person carrying the personal information terminal arbitrarily pushes an alarm button.

The invention comprises: physiological state detecting means; transmitting means of transmitting a sensor signal detected by said physiological state detecting means; receiving means of receiving a sensor signal from said sensor signal transmitting means; a wearable personal information terminal having at least sending means of sending the physiological signal to abase station; abase station for receiving the sensor signals from a plurality of said wearable personal information terminals by wireless; and personal characteristics information calculating means of integrally processing, by means of a network, the signals obtained from said sensor signals from said base station and thereby obtaining the personal characteristics information of said human body; thereby permitting accurate, easy, and simple measurement of the action and the personal characteristics information of person such as the position, the posture, the action information, and the physiological information of a person of object of detection in a room.

In particular, when the action and the physiological information of a human body are integrated, the personal characteristics information can be obtained more efficiently. Further, state determining means attached to the human body communicates with the base station by wireless, and the base station is connected to the network. This permits integrated management of the personal characteristics information of human bodies in a plurality of rooms or specified areas. Accordingly, the action of the human bodies in the whole building can be understood in real time. This permits various applications such as abnormality detection, air conditioning/illumination control, and security.

As such, the posture, action, motion state, and physiological state of the human body are specified. Further, the personal characteristics information of a plurality of human bodies can be efficiently integrated by a network. Thus, the invention permits easy, accurate, reliable, and inexpensive personal characteristics information acquisition, thereby substantially contributing to the expansion of home information infrastructure business.

(D) Further, the present invention advantageously provides an action detection system in which information on the action state of a person of object of detection is automatically transmitted via the Internet to a first Internet terminal of a predetermined manager (such as a doctor), and a second Internet terminal is used for performing interactive communications with the first Internet terminal via the Internet, whereby information exchange can be carried out between the person of object of detection or the person's helper and the manager.

According to an action detection system according to the invention, a human body entering a room can be identified.

Further, the action of the human body, such as in-room position, posture, and action information, can be measured accurately. The personal characteristics information can be compared and evaluated with the action and the physiological information of the person, whereby an abnormality is determined. The abnormality is notified to the person or another person. Further, the communications with the person having the abnormality or the person's helper can be carried out by the Internet or another network.

Further, the system is configured such that in case of abnormality, a person is sent to the human body having an abnormality. This creates more safe and relaxed environment.

Further, with equipment such as air conditioner, illumination means, and the like which is connected to a network and arbitrarily adjusted in order to create comfortable environment in response to the obtained personal action information, more comfortable environment is obtained.

Further, state determining means attached to the human body communicates with the base station by wireless, and the base station is connected to the network. This permits integrated management of the personal characteristics information of human bodies in a plurality of rooms or specified areas. Accordingly, the action of the human bodies in the whole building can be understood in real time. This permits various applications such as abnormality detection, air conditioning/illumination control, and security.

As such, the human body is identified, and the position of the human body is specified. Further, the posture, action, and motion state of the human body are specified. Furthermore, the action information and the physiological information of a person is integrated. Then, daily action and physiological state are compared and evaluated, whereby an abnormality in the action is determined and notified. Then, the abnormality is resolved, whereby more safe, relaxed, and comfortable environment is obtained. Accordingly, an abnormal action detection system according to the invention permits easy, highly accurate, reliable, and inexpensive abnormal action detection and prediction, thereby substantially contributing to the expansion of home information infrastructure business.

What is claimed is:

1. A state information acquisition system comprising:
a terminal which has physiological state detecting means of detecting a physiological state of a person or animal, posture/action detecting means of detecting a posture and/or action state of said person or animal, and detection signal transmitting means of transmitting detection signals based on the detection of (1) said physiological state and (2) said posture and/or action state, and is attached to said person or animal;
movement direction detecting means of detecting a movement direction of the person or animal upon entering or exiting a room, the movement direction detecting means detached from the person or animal;
position detecting means of detecting two-dimensional coordinates of the person or animal in the room; and
signal receiving and processing means which receives and processes a signal transmitted from said terminal and the movement direction detecting means and the position detecting means, and is located in a predetermined region;
thereby obtaining state information indicating the state of said person or animal on the basis of said detection signal.

2. A state information acquisition system according to claim 1 comprising:
storing means of storing, as structured data, said state information obtained on the basis of said detection signal and/or standard information previously prepared;
comparing and determining means of comparing said obtained state information with said stored structured data on the basis of a predetermined reference and thereby determining whether the state of said person or animal of object of detection is normal or abnormal;
notifying means of notifying abnormality when said state of said person or animal is determined to be abnormal;
means accumulating said structure data by correcting previously input information of a standard person or animal using said obtained state information and continuously accumulating said state information for each of said person or animal;
wherein (1) when the accumulation of said state information is not yet sufficient, the data mainly based on said previously input information of a standard person or animal is used, while (2) when the accumulation of said state information is sufficient, said structured data generated by correcting previously input information of a standard person or animal is used.

3. A state information acquisition apparatus comprising signal receiving and processing means which receives and processes a detection signal of a physiological state of a person or animal and a detection signal of a posture and/or action state of a person or animal located in a predetermined region,
state information-storing means of storing state information of a predetermined physiological state of a standard person or animal,
updating means of updating the state information storing means using the processed detection signal of a physiological state of a real person or animal,
comparing means of comparing a processed detection signal of a physiological state of a real person or animal with the predetermined physiological state of the standard person or animal, when the state information storing means only includes the predetermined physiological state of the standard person or animal,
comparing means of comparing a processed detection signal of a physiological state of a real person or animal with the state information of the real person or animal, when the state information storing means includes the state information of the real person or animal, and
notifying means of notifying an abnormality in response to the comparing means.

4. A state information acquisition system comprising:
a terminal which has physiological state detecting means of detecting a physiological state of a person or animal and detection signal transmitting means of transmitting a detection signal based on said detection, and is attachable to said person or animal;
receiving means which receives a signal transmitted from said terminal and is located in a predetermined region;
signal processing and outputting means of processing said received signal and then outputting the result; thereby obtaining state information indicating the state of said person or animal on the basis of said detection signal;
means of inputting information of a standard person or animal for use as state information; and
means of accumulating said state information by correcting previously input information of the standard person or animal using said obtained state information and continuously accumulating said state information for each of said person or animal;

wherein (1) when the accumulation of said state information is not yet sufficient, the data mainly based on said previously input information of the standard person or animal is used, while (2) when the accumulation of said state information is sufficient, said state information generated by correcting previously input information of the standard person or animal is used.

5. A state information acquisition system according to claim 4 comprising position detecting means of detecting the position of said person or animal, wherein when said state information is obtained, the result of detection carried out by said position detecting means is considered.

6. A state information acquisition system comprising:

position detecting means of detecting a position of a person or animal and thereby transmitting a position detection signal;

a terminal which has posture/action detecting means of detecting the posture and/or action state of said person or animal and detection signal transmitting means of transmitting a state detection signal based on the detection of said posture and/or action state, and is attachable to said person or animal;

signal receiving and processing means which receives and processes said position detection signal and said state detection signal, and is located in a predetermined region;

thereby obtaining state information indicating the state of said person or animal on the basis of the result of said processing;

means of Inputting information of a standard person or animal for use as state information; and means of accumulating said state information by correcting previously input information of the standard person or animal using said obtained state information and continuously accumulating said state information for each of said person or animal;

wherein (1) when the accumulation of said state information is not yet sufficient, the data mainly based on said previously input information of the standard person or animal is used, while (2) when the accumulation of said state information is sufficient, said state information generated by correcting previously input information of the standard person or animal is used.

7. A state information acquisition system according to claim 6 wherein:

the object of said detection is a person;

said state information acquisition system comprises lavatory state detecting means of detecting the state of said person in a lavatory; and when said state information is obtained, the result of detection carried out by said lavatory state detecting means is considered.

8. A state information acquisition system according to claim 6 wherein:

the object of said detection is a person;

said state information acquisition system comprises on-bed state detecting means of detecting the state of said person on a bed; and when said state information is obtained, the result of detection carried out by said on-bed state detecting means is considered.

9. A state information acquisition system according to claim 6 comprising:

storing means of storing, as structured data, said state information obtained on the basis of the result of said processing and/or standard information previously prepared;

comparing and determining means of comparing said obtained state information with said stored structured data on the basis of a predetermined reference and thereby determining whether the state of said person or animal of object of detection is normal or abnormal; and notifying means of notifying abnormality when said state of said person or animal is determined to be abnormal.

10. A state information acquisition apparatus comprising signal receiving and processing means which receives and processes a position detection signal based on detection of a position of a person or animal and a state detection signal based on detection of a posture and/or action state of said person or animal and is located in a predetermined region, wherein (1) the output from said signal receiving and processing means contains state information which is based on the result of said processing and indicates the state of said person or animal, or (2) said processed signal is output for the preparation of state information;

means of inputting information of a standard person or animal for use as state information; and means of accumulating said state Information by correcting previously input information of the standard person or animal using said obtained state information and continuously accumulating said state information for each of said person or animal;

wherein (1) when the accumulation of said state information is not yet sufficient, the data mainly based on said previously input information of the standard person or animal is used, while (2) when the accumulation of said state information is sufficient, said state information generated by correcting previously input information of the standard person or animal is used.

11. A state information acquisition system comprising:

a terminal which has physiological state detecting means of detecting physiological state of a person or animal, posture/action detecting means of detecting a posture and/or action state of said person or animal, and detection signal transmitting means of transmitting detection signals based on the detection of (1) said physiological state and (2) said posture and/or action state, and is attached to said person or animal;

signal receiving and processing means which receives and processes a to signal transmitted from said terminal and is located in a predetermined region, thereby obtaining state information indicating the state of said person or animal;

storing means of storing, as structured data, said state information obtained on the basis of said detection signal and/or standard information previously prepared;

comparing and determining means of comparing said obtained state information with said stored structured data on the basis of a predetermined reference and thereby determining whether the state of said person or animal of object of detection is normal or abnormal;

notifying means of notifying abnormality when said state of said person or animal is determined to be abnormal;

means of accumulating said state Information by correcting previously input information of the standard person or animal using said obtained state information and continuously accumulating said state information for each of said person or animal;
wherein (1) when the accumulation of said state information is not yet sufficient, the data mainly based on said previously input information of the standard person or animal is used, while (2) when the accumulation of said state information is sufficient, said state information generated by correcting previously input information of the standard person or animal is used.

* * * * *

UNITED STATES PATENT AND TRADEMARK OFFICE
CERTIFICATE OF CORRECTION

PATENT NO.     : 6,616,607 B2
DATED          : September 2, 2003
INVENTOR(S)    : Hashimoto et al.

It is certified that error appears in the above-identified patent and that said Letters Patent is hereby corrected as shown below:

<u>Title page,</u>
Item [56], References Cited, insert

--       FOREIGN PATENT DOCUMENTS

JP    11-88518    3/30/1999
        JP    10-113343    5/6/1998
        EP    0 816 986    1/7/1998 --.

Signed and Sealed this

Fourth Day of May, 2004

JON W. DUDAS
*Acting Director of the United States Patent and Trademark Office*